US012163951B2

(12) United States Patent
Capila et al.

(10) Patent No.: US 12,163,951 B2
(45) Date of Patent: *Dec. 10, 2024

(54) METHODS FOR PREDICTING RESPONSE TO TREATMENT

(71) Applicant: Momenta Pharmaceuticals, Inc., Titusville, NJ (US)

(72) Inventors: Ishan Capila, Ashland, MA (US); Victor Farutin, Watertown, MA (US); Thomas Prod'homme, Somerville, MA (US); Kevin McConnell, Branford, CT (US); Leona Ling, Winchester, MA (US)

(73) Assignee: Momenta Pharmaceuticals, Inc., Titusville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/187,421

(22) Filed: Mar. 21, 2023

(65) Prior Publication Data
US 2023/0221302 A1 Jul. 13, 2023

Related U.S. Application Data

(63) Continuation of application No. 16/648,955, filed as application No. PCT/US2018/051606 on Sep. 18, 2018, now Pat. No. 11,639,923.

(60) Provisional application No. 62/560,628, filed on Sep. 19, 2017.

(51) Int. Cl.
*G01N 33/50* (2006.01)
*C07K 16/24* (2006.01)

(52) U.S. Cl.
CPC ....... *G01N 33/5047* (2013.01); *C07K 16/241* (2013.01); *G01N 2800/102* (2013.01); *G01N 2800/52* (2013.01)

(58) Field of Classification Search
CPC ......... G01N 33/5047; G01N 2800/102; G01N 2800/52; C07K 16/241
See application file for complete search history.

(56) References Cited

U.S. PATENT DOCUMENTS

| | | |
|---|---|---|
| 7,390,630 B1 | 6/2008 | Brennan et al. |
| 11,639,923 B2 | 5/2023 | Capila et al. |
| 2003/0154032 A1 | 8/2003 | Pittman et al. |
| 2010/0196402 A1 | 8/2010 | Ehrenstein et al. |
| 2015/0299252 A1 | 10/2015 | Eggink et al. |

FOREIGN PATENT DOCUMENTS

WO 2010034864 A1 4/2010

OTHER PUBLICATIONS

Koiwa (J. Nippon Med Sch 2016 83:118-124). (Year: 2016).*
Abbas et al., "Immune Response in Silico (IRIS): Immune-Specific Genes Identified from a Compendium of Microarray Expression Data," Genes and Immunity (2005) vol. 6, pp. 319-331.
Allantaz et al., "Expression Profiling of Human Immune Cell Subsets Identifies miRNA-mRNA Regulatory Relationships Correlated with Cell Type Specific Expression," PLoS ONE (2012) 7(1):e29979, pp. 1-12.
Bienkowska et al., "Convergent Random Forest Predictor: Methodology for Predicting Drug Response from Genome-Scale Data Applied to Anti-TNF Response," Genomics (2009) 94(6), pp. 423-432.
Catrina et al., "Evidence that Anti-Tumor Necrosis Factor Therapy with Both Etanercept and Infliximab Induces Apoptosis in Macrophages, but not Lymphocytes, in Rheumatoid Arthritis Joints," Arthritis & Rheumatism (Jan. 2005) 52(1), pp. 61-72.
Chandrashekara et al., "Neutrophil-Lymphocyte Ratio, Pain Perception, and Disease Activity Score May Serve as Important Predictive Markers for Sustained Remission in Rheumatoid Arthritis," Reumatismo (2015) 67(3), pp. 109-115.
Farutin et al., "Molecular Profiling of RA Patients Suggests a Differential Involvement of Adaptive and Innate Cell Populations in Response to Anti-TNF Treatment," (18 Sept, 2017) Presented at the 2017 ACR/ARHP Annual Meeting, Abstract No. 1019, pp. 1-3.
Final Office Action for U.S. Appl. No. 16/648,955 dated May 13, 2022.
Hart et al., "Potential Anti-Inflammatory Effects of Interleukin 4: Suppression of Human Monocyte Tumor Necrosis Factor Alpha, Interleukin 1, and Prostaglandin E2," Proc. Natl. Acad. Sci. USA (May 1989) vol. 86, pp. 3803-3807.
International Preliminary Report on Patentability for International Application No. PCT/US2018/051606 dated Apr. 2, 2020.
International Search Report and Written Opinion for International Application No. PCT/US2018/051606 dated Dec. 3, 2018.
Julia et al., "An Eight-Gene Blood Expression Profile Predicts the Response to Infliximab in Rheumatoid Arthritis," PloS One (Oct. 2009) 4(10):e7556, pp. 1-8.
Junta et al., "Differential Gene Expression of Peripheral Blood Mononuclear Cells from Rheumatoid Arthritis Patients may Discriminate Immunogenetic, Pathogenic and Treatment Features," Immunology (2008) 127(3), pp. 365-372.
Koczan et al., "Molecular Discrimination of Responders and Nonresponders to Anti-TNFalpha Therapy in Rheumatoid Arthritis by Etanercept," Arthr. Res. Ther. (2008) 10(3):R50, pp. 1-10.
Koiwa et al., "Neutrophil/Lymphocyte Ratio in Patients with Rheumatoid Arthritis Treated with Biological Agents," J. Nippon Med. Sch. (2016) 83(3), pp. 118-124.
Lequerre et al., "Gene Profiling in White Blood Cells Predicts Infliximab Responsiveness in Rheumatoid Arthritis," Arth. Res. Ther., (2006) 8(4):R105, pp. 1-11.

(Continued)

*Primary Examiner* — Changhwa J Cheu
(74) *Attorney, Agent, or Firm* — Troutman Pepper Hamilton Sanders LLP; Mark R. Bell; Tate L. Tischner

(57) ABSTRACT

Described herein are methods for treating rheumatoid arthritis by determining whether a subject having rheumatoid arthritis will respond to an anti-TNF-alpha therapy based on the number of innate and adaptive immune cells in a sample from the subject prior to treatment.

10 Claims, 54 Drawing Sheets

(56) References Cited

OTHER PUBLICATIONS

Linsley et al., "Copy Number Loss of the Interferon Gene Cluster in Melanomas is Linked to Reduced T Cell Infiltrate and Poor Patient Prognosis," PloS ONE (2014) 9(10):e109760, pp. 1-9.
MacIsaac et al., "Pre-Treatment Whole Blood Gene Expression is Associated with 14-Week Response Assessed by Dynamic Contrast Enhanced Magnetic Resonance Imaging in Infliximab-Treated Rheumatoid Arthritis Patients," PloS One (2014) 9(12):e113937, pp. 1-18.
Manda et al., "Imbalance of Peripheral B Lymphocytes and NK Cells in Rheumatoid Arthritis," J. Cell Mol. Med. (2003) 7(1), pp. 79-88.
Mercan et al., "The Association Between Neutrophil/Lymphocyte Ratio and Disease Activity in Rheumatoid Arthritis and Ankylosing Spondylitis," J. Clin. Lab. Anal. (2016) vol. 30, pp. 597-601.
Mesko et al., "Peripheral Blood Derived Gene Panels Predict Response to Infliximab in Rheumatoid Arthritis and Crohn's Disease," Genome Medicine (2013) 5:59, pp. 1-10.
Meugnier et al., "Gene Expression Profiling in Peripheral Blood Cells of Patients with Rheumatoid Arthritis in Response to Anti-TNF-alpha Treatments," Physiol. Genomics (2011) vol. 43, pp. 365-371.
Nakamura et al., "Identification of Baseline Gene Expression Signatures Predicting Therapeutic Responses to Three Biologic Agents in Rheumatoid Arthritis: A Retrospective Observational Study," Arthr. Res. Ther. (2016) 18:159, pp. 1-12.
Non-Final Office Action for U.S. Appl. No. 16/648,955 dated Aug. 19, 2022.
Non-Final Office Action for U.S. Appl. No. 16/648,955 dated Sep. 9, 2021.
Notice of Allowance for U.S. Appl. No. 16/648,955 dated Dec. 21, 2022.
Oliveira et al., "Differential Gene Expression Profiles May Differentiate Responder and Nonresponder Patients with Rheumatoid Arthritis for Methotrexate (MDX) Monotherapy and MTX plus Tumor Necrosis Factor Inhibitor Combined Therapy," J. Rheum. (2012) 39(8), pp. 1524-1532.
Oswald et al., "Modular Analysis of Peripheral Blood Gene Expression in Rheumatoid Arthritis Captures Reproducible Gene Expression Changes in Tumor Necrosis Factor Responders," Arthr. Rheum. (Feb. 2015) 67(2), pp. 344-351.
Rossol et al., "The CD14brightCD16+ Monocyte Subset is Expanded in Rheumatoid Arthritis and Promotes Expansion of the Th17 Cell Population," Arthritis & Rheumatism (Mar. 2012) 64(3), pp. 671-677.
Sekiguchi et al., "Messenger Ribonucleic Acid Expression Profile in Peripheral Blood Cells from RA Patients Following Treatment with an Anti-TNF-alpha Monoclonal Antibody, Infliximab," Rheumatology (2008) 47(6), pp. 780-788.
Seymour et al., "Anti-TNF Agents for Rheumatoid Arthritis," Br. J. Pharmacol. (2001) vol. 51, pp. 201-208.
Stuhlmuller et al., "CD11c as a Transcriptional Biomarker to Predict Response to Anti-TNF Monotherapy with Adalimumab in Patients with Rheumatoid Arthritis," Clin. Pharm. Ther. (Mar. 2010) 87(3), pp. 311-321.
Tanino et al., "Prediction of Efficacy of Anti-TNF Biologic Agent, Infliximab, for Rheumatoid Arthritis Patients using a Comprehensive Transcriptome Analysis of White Blood Cells," Biochem. Biophys. Res. Commun. (2009) 387(2), pp. 261-265.
Thanapati et al., "Impaired NK Cell Functionality and Increased TNF-alpha Production as Biomarkers of Chronic Chikungunya Arthritis and Rheumatoid Arthritis," Human Immunology (2017) vol. 78, pp. 370-374.
Toonen et al., "Validation Study of Existing Gene Expression Signatures for Anti-TNF Treatment in Patients with Rheumatoid Arthritis," PLoS One (2012) 7(3):e33199, pp. 1-6.
Uslu et al., "Two New Inflammatory Markers Associated with Disease Activity Score-28 in Patients with Rheumatoid Arthritis: Neutrophil-Lymphocyte Ratio and Platelet-Lymphocyte Ratio," Intl. J. Rheumatic Diseases (2015) vol. 18, pp. 731-735.
Van Baarsen et al., "Pharmacogenomics of Infliximab Treatment using Peripheral Blood Cells of Patients with Rheumatoid Arthritis," Genes and Immunity (2010) 11(8), pp. 622-629.
Van Baarsen et al., "Regulation of IFN Response Gene Activity During Infliximab Treatment in Rheumatoid Arthritis is Associated with Clinical Response to Treatment," Arthritis Research & Therapy (2010) 12(1):R11, pp. 1-10.
Wright et al., "Interferon Gene Expression Signature in Rheumatoid Arthritis Neutrophils Correlates with a Good Response to TNFi Therapy," Rheumatology (2015) 54(1), pp. 188-193.

* cited by examiner

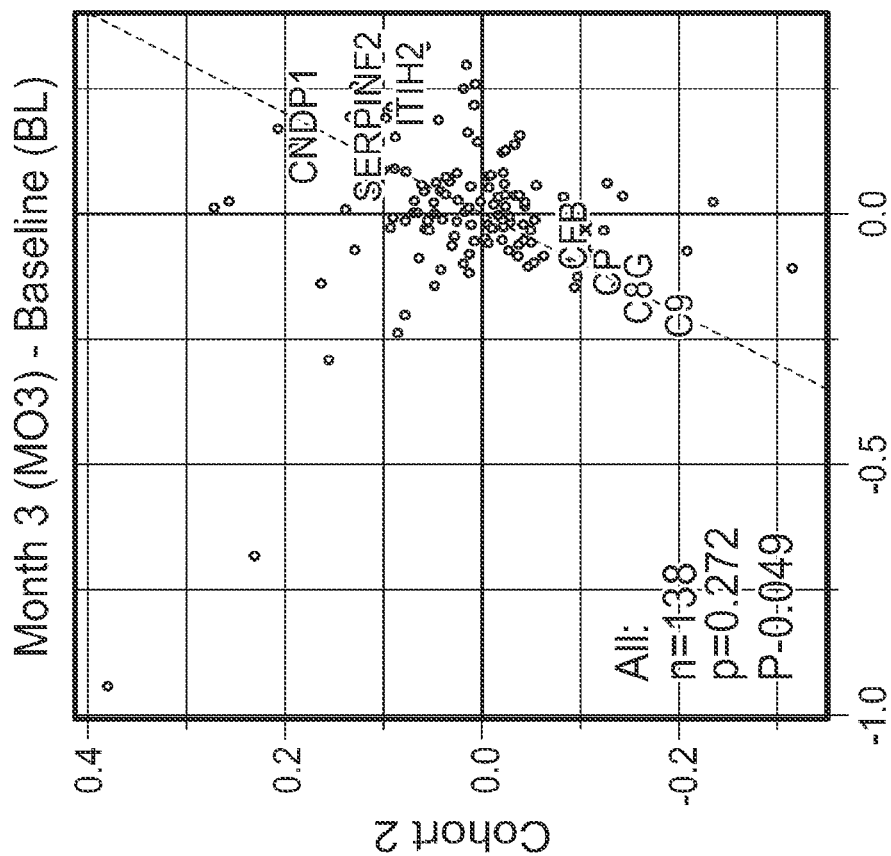
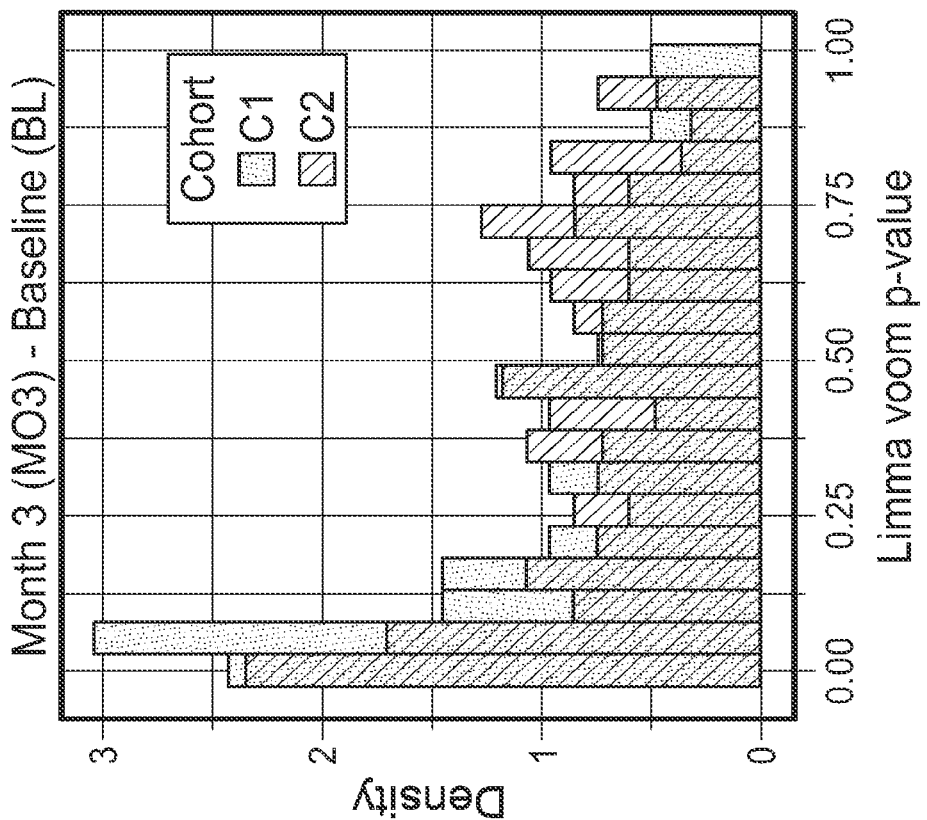
FIG. 1F
FIG. 1E

| Innate Immune Response Genes | Adaptive Immune Response Genes |
|---|---|
| ADIPOR1 | ABHD14A |
| AGO2 | ACTR6 |
| ALDH2 | ANXA2R |
| APOBEC3B | ARGLU1 |
| ARG1 | ATP5L |
| ARSB | ATP5O |
| ASGR1 | BCL7C |
| B4GALT5 | BDH2 |
| BATF2 | C11orf80 |
| BCL2L1 | C12orf57 |
| BMP2K | C19orf48 |
| BPGM | C19orf53 |
| BPI | C19orf70 |
| BTNL3 | C6orf48 |
| CA5BP1 | C7orf50 |
| CASP5 | CCDC107 |
| CCDC149 | CCDC65 |
| CD163 | CCDC82 |
| CD1D | CCDC85B |
| CD300C | CD2 |
| CD36 | CD22 |
| CDC42EP4 | CD320 |
| CDKN1C | CD3D |
| CES1 | CD48 |
| CHST2 | CD52 |
| CLEC12A | CD72 |
| CLMN | CD79A |
| CLTCL1 | CD79B |
| CRISPLD2 | CD8A |
| CTNNA1 | CD8B |
| CYP1B1 | CLEC2D |
| CYP4F3 | COA4 |
| DAPK1 | COL6A2 |
| DCAF12 | COMMD6 |
| DCUN1D1 | COX16 |
| DEFA1B | COX6C |
| DEFA3 | COX7C |
| DHRS9 | CRIP1 |

FIG. 6

| Innate Immune Response Genes | Adaptive Immune Response Genes |
|---|---|
| DIAPH2 | CRIP2 |
| DICER1 | EEF1A1 |
| DNAJC13 | EEF1B2 |
| E2F2 | EEF1D |
| EIF2AK2 | EEF1G |
| EPB41L3 | EIF3E |
| ERN1 | EMG1 |
| ETV7 | FAU |
| EXT1 | FBL |
| FAM126B | FCRLA |
| FAM129B | FGFBP2 |
| FAM198B | FKBP3 |
| FAM210B | GADD45GIP1 |
| FAXDC2 | GAS5 |
| FCAR | GIMAP7 |
| FCN1 | GNL3 |
| FGD4 | GPX7 |
| FKBP5 | GZMA |
| FOXO4 | GZMH |
| FRY | GZMM |
| FXYD6 | HINT1 |
| GBE1 | HAL-DPB1 |
| GLRX5 | HRAS |
| GMPR | HSP90AA1 |
| GRINA | HSPE1 |
| GRN | ITM2A |
| H1F0 | KLRB1 |
| HBA1 | KLRK1 |
| HBG2 | LCN10 |
| HIP1 | LIME1 |
| HSPA1A | LINC00926 |
| HSPA1B | LOC374443 |
| IDO1 | LRRC75A-AS1 |
| IFIT1B | LSM7 |
| IGF2BP2 | LTK |
| IQSEC2 | MATK |
| IRAK3 | MRPL11 |
| ITGA2B | MRPL15 |
| JUP | MRPS22 |
| KCNC3 | MRPS28 |
| KDM1B | MRPS33 |
| KIAA1324 | MS4A1 |
| KIF3C | MXRA7 |

FIG. 6 (Cont.)

| Innate Immune Response Genes | Adaptive Immune Response Genes |
|---|---|
| KLF1 | MYBL1 |
| KLF4 | MZT2A |
| KLHL8 | NCR3 |
| LCN2 | NDUFA4 |
| LDLR | NDUFB2 |
| LHFPL2 | NDUFS4 |
| LILRB4 | NDUFS5 |
| LINC01270 | NFU1 |
| LMTK2 | NME1-NME2 |
| LOC100506585 | NOSIP |
| LOXL3 | NSA2 |
| LRP1 | NSG1 |
| LRP3 | PCBP4 |
| LRRC75A | PDZD4 |
| LRRK1 | PFDN5 |
| LSM12 | PKIG |
| LTF | POLR2I |
| MAFB | POLR2K |
| MAP2K3 | PSMC6 |
| MED13L | PTPRCAP |
| MFN2 | PTRHD1 |
| MGST1 | RPL10A |
| MICAL2 | RPL11 |
| MKRN1 | RPL12 |
| MLC1 | RPL13 |
| MMP17 | RPL13A |
| MMP9 | RPL13AP5 |
| MPEG1 | RPL14 |
| MPP1 | RPL15 |
| MTMR11 | RPL17-C18orf32 |
| MYCL | RPL18 |
| MYOF | RPL18A |
| NCOA2 | RPL19 |
| NDST1 | RPL21 |
| NFIX | RPL21P28 |
| NLRC4 | RPL23 |
| NLRP3 | RPL23A |
| NR6A1 | RPL24 |
| NREP | RPL26 |
| NUDT16P1 | RPL27 |
| P2RX7 | RPL27A |
| PADI4 | RPL29 |
| PDZK1IP1 | RPL3 |

FIG. 6 (Cont.)

| Innate Immune Response Genes | Adaptive Immune Response Genes |
|---|---|
| PFKFB2 | RPL30 |
| PGAM1 | RPL31 |
| PGD | RPL32 |
| PLAGL1 | RPL34 |
| PPP4R2 | RPL35 |
| PRRG4 | RPL35A |
| PSAP | RPL36 |
| PSTPIP2 | RPL36A |
| PXK | RPL36AL |
| REL | RPL37 |
| RIOK3 | RPL37A |
| RNF10 | RPL38 |
| RNF24 | RPL39 |
| RP2 | RPL4 |
| RPS6KA2 | RPL41 |
| RTN1 | RPL5 |
| RUNDC3A | RPL6 |
| S1PR3 | RPL7 |
| SEC14L1 | RPL7A |
| SELENBP1 | RPL8 |
| SELL | RPL9 |
| SELP | RPLP0 |
| SERPINB8 | RPLP1 |
| SERPING1 | RPS10 |
| SESTD1 | RPS11 |
| SIAH2 | RPS12 |
| SIGLEC1 | RPS13 |
| SIGLEC14 | RPS14 |
| SIRPB1 | RPS15 |
| SLC1A5 | RPS15A |
| SLC22A15 | RPS16 |
| SLC24A4 | RPS18 |
| SLC26A8 | RPS19 |
| SLC31A1 | RPS2 |
| SLC37A2 | RPS20 |
| SLC6A8 | RPS21 |
| SLC8A1 | RPS23 |
| SMAP2 | RPS24 |
| SMOX | RPS25 |
| SNCA | RPS27 |
| SNX10 | RPS27A |
| SORT1 | RPS28 |
| SPECC1 | RPS29 |

FIG. 6 (Cont.)

| Innate Immune Response Genes | Adaptive Immune Response Genes |
|---|---|
| TAL1 | RPS3 |
| TBC1D8 | RPS3A |
| TCN1 | RPS4X |
| TCN2 | RPS5 |
| TCP11L2 | RPS6 |
| TESC | RPS7 |
| TFDP1 | RPS8 |
| TICAM2 | RPS9 |
| TIRAP | RPSA |
| TJP2 | RSL24D1 |
| TM6SF1 | SEC11C |
| TMEM150B | SIT1 |
| TMEM170B | SNRPD2 |
| TMEM63B | SRP14 |
| TNFRSF9 | STAP1 |
| TNS1 | STMN3 |
| TNS3 | SUB1 |
| TPST1 | SVIP |
| TRIM58 | TAF7 |
| TRIO | TMA7 |
| TSHZ3 | TMEM134 |
| VWCE | TMEM42 |
| WARS | TNFRSF25 |
| WLS | TOMM7 |
| XXYLT1 | TP53I13 |
| YBX3 | TP53TG1 |
| YOD1 | TPM2 |
| ZBTB47 | TPT1 |
|  | TRAT1 |
|  | TSTD1 |
|  | TTC16 |
|  | UQCRB |
|  | UQCRH |
|  | WNT10B |
|  | ZAP70 |
|  | ZNF14 |
|  | ZNF32 |

FIG. 6 (Cont.)

| Class | CellType | GeneSymbol | Description |
|---|---|---|---|
| Innate | Neutrophils | ALPL | alkaline phosphatase, liver/bone/kidney |
| Innate | Neutrophils | AQP9 | aquaporin 9 |
| Innate | Neutrophils | CSF3R | colony stimulating factor 3 receptor (granulocyte) |
| Innate | Neutrophils | CXCR1 | chemokine (C-X-C motif) receptor 1 |
| Innate | Neutrophils | CXCR2 | chemokine (C-X-C motif) receptor 2 |
| Innate | Neutrophils | CYP4F3 | cytochrome P450, family 4, subfamily F, polypeptide 3 |
| Innate | Neutrophils | FCGR3B | Fc fragment of IgG, low affinity IIIb, receptor (CD16b) |
| Innate | Neutrophils | G0S2 | G0/G1 switch 2 |
| Innate | Neutrophils | MME | membrane metallo-endopeptidase |
| Innate | Neutrophils | TNFRSF10C | tumor necrosis factor receptor superfamily, member 10c, decoy without an intracellular domain |
| Innate | Monocytes | CD300E | CD300e molecule |
| Innate | Monocytes | CD36 | CD36 molecule (thrombospondin receptor) |
| Innate | Monocytes | CPVL | carboxypeptidase, vitellogenic-like |
| Innate | Monocytes | FCN1 | ficolin (collagen/fibrinogen domain containing) 1 |
| Innate | Monocytes | IL1B | interleukin 1, beta |
| Innate | Monocytes | LYZ | lysozyme |
| Innate | Monocytes | MAFB | v-maf avian musculoaponeurotic fibrosarcoma oncogene homolog B |
| Innate | Monocytes | STAB1 | stabilin 1 |
| Innate | Monocytes | TGFBI | transforming growth factor, beta-induced, 68kDa |
| Innate | Monocytes | VCAN | versican |
| Adaptive | B-cells | BANK1 | B-cell scaffold protein with ankyrin repeats 1 |
| Adaptive | B-cells | CD19 | CD19 molecule |
| Adaptive | B-cells | CD22 | CD22 molecule |
| Adaptive | B-cells | CD79A | CD79a molecule, immunoglobulin-associated alpha |
| Adaptive | B-cells | FAM129C | family with sequence similarity 129, member C |
| Adaptive | B-cells | FCRL1 | Fc receptor-like 1 |
| Adaptive | B-cells | LINC00926 | long intergenic non-protein coding RNA 926 |
| Adaptive | B-cells | MS4A1 | membrane-spanning 4-domains, subfamily A, member 1 |
| Adaptive | B-cells | PAX5 | paired box 5 |
| Adaptive | B-cells | TCL1A | T-cell leukemia/lymphoma 1A |
| Adaptive | CD4 | CACNA1I | calcium channel, voltage-dependent, T type, alpha 1I subunit |
| Adaptive | CD4 | CD28 | CD28 molecule |
| Adaptive | CD4;CD8 | CD3E | CD3e molecule, epsilon (CD3-TCR complex) |
| Adaptive | CD4 | CHRM3-AS2 | CHRM3 antisense RNA 2 |
| Adaptive | CD4 | CTLA4 | cytotoxic T-lymphocyte-associated protein 4 |
| Adaptive | CD4 | ICOS | inducible T-cell co-stimulator |
| Adaptive | CD4;CD8 | IL7R | interleukin 7 receptor |
| Adaptive | CD4 | INPP4B | inositol polyphosphate-4-phosphatase, type II, 105kDa |
| Adaptive | CD4;CD8 | LEF1 | lymphoid enhancer-binding factor 1 |

FIG. 7

| Class | CellType | GeneSymbol | Description |
|---|---|---|---|
| Adaptive | CD4 | MAL | mal, T-cell differentiation protein |
| Adaptive | CD8 | BCL11B | B-cell CLL/lymphoma 11B (zinc finger protein) |
| Adaptive | CD8 | CD3D | CD3d molecule, delta (CD3-TCR complex) |
| Adaptive | CD8 | CD8A | CD8a molecule |
| Adaptive | CD8 | GZMK | granzyme K (granzyme 3; tryptase II) |
| Adaptive | CD8 | ITK | IL2-inducible T-cell kinase |
| Adaptive | CD8 | NELL2 | NEL-like 2 (chicken) |
| Adaptive | CD8 | THEMIS | thymocyte selection associated |
| Adaptive | NK | B3GNT7 | UDP-GlcNAc:betaGal beta-1,3-N-acetylglucosaminyltransferase 7 |
| Adaptive | NK | FGFBP2 | fibroblast growth factor binding protein 2 |
| Adaptive | NK | GNLY | granulysin |
| Adaptive | NK | GPR56 | G protein-coupled receptor 56 |
| Adaptive | NK | GZMB | granzyme B (granzyme 2, cytotoxic T-lymphocyte-associated serine esterase 1) |
| Adaptive | NK | IL2RB | interleukin 2 receptor, beta |
| Adaptive | NK | NCAM1 | neural cell adhesion molecule 1 |
| Adaptive | NK | PRF1 | perforin 1 (pore forming protein) |
| Adaptive | NK | S1PR5 | sphingosine-1-phosphate receptor 5 |
| Adaptive | NK | SH2D1B | SH2 domain containing 1B |

FIG. 7 (Cont.)

| Class | CellType | GeneSymbol | Description |
|---|---|---|---|
| Innate | Neutrophils | ADM | adrenomedullin |
| Innate | Neutrophils | ALPL | alkaline phosphatase, liver/bone/kidney |
| Innate | Neutrophils | ANXA3 | annexin A3 |
| Innate | Neutrophils | AQP9 | aquaporin 9 |
| Innate | Neutrophils | BASP1 | brain abundant, membrane attached signal protein 1 |
| Innate | Neutrophils | BTNL8 | butyrophilin-like 8 |
| Innate | Neutrophils | C5AR1 | complement component 5a receptor 1 |
| Innate | Neutrophils | CEACAM3 | carcinoembryonic antigen-related cell adhesion molecule 3 |
| Innate | Neutrophils | CHI3L1 | chitinase 3-like 1 (cartilage glycoprotein-39) |
| Innate | Neutrophils | CMTM2 | CKLF-like MARVEL transmembrane domain containing 2 |
| Innate | Neutrophils | CNTNAP3 | contactin associated protein-like 3 |
| Innate | Neutrophils | CSF3R | colony stimulating factor 3 receptor (granulocyte) |
| Innate | Monocytes;Neutrophils | CXCL8 | chemokine (C-X-C motif) ligand 8 |
| Innate | Neutrophils | CXCR1 | chemokine (C-X-C motif) receptor 1 |
| Innate | Neutrophils | CXCR2 | chemokine (C-X-C motif) receptor 2 |
| Innate | Neutrophils | CYP4F3 | cytochrome P450, family 4, subfamily F, polypeptide 3 |
| Innate | Neutrophils | DGAT2 | diacylglycerol O-acyltransferase 2 |
| Innate | Neutrophils | EMR3 | egf-like module containing, mucin-like, hormone receptor-like 3 |
| Innate | Neutrophils | EPHB1 | EPH receptor B1 |
| Innate | Neutrophils | FCGR3B | Fc fragment of IgG, low affinity IIIb, receptor (CD16b) |
| Innate | Neutrophils | FFAR2 | free fatty acid receptor 2 |
| Innate | Neutrophils | FPR1 | formyl peptide receptor 1 |
| Innate | Neutrophils | FPR2 | formyl peptide receptor 2 |
| Innate | Neutrophils | G0S2 | G0/G1 switch 2 |
| Innate | Neutrophils | GLT1D1 | glycosyltransferase 1 domain containing 1 |
| Innate | Neutrophils | GPR97 | G protein-coupled receptor 97 |
| Innate | Neutrophils | IL1R2 | interleukin 1 receptor, type II |
| Innate | Neutrophils | KCNJ15 | potassium inwardly-rectifying channel, subfamily J, member 15 |
| Innate | Neutrophils | KCNJ2 | potassium inwardly-rectifying channel, subfamily J, member 2 |
| Innate | Neutrophils | KRT23 | keratin 23 (histone deacetylase inducible) |
| Innate | Neutrophils | LRG1 | leucine-rich alpha-2-glycoprotein 1 |
| Innate | Neutrophils | MEFV | Mediterranean fever |
| Innate | Neutrophils | MGAM | maltase-glucoamylase (alpha-glucosidase) |
| Innate | Neutrophils | MME | membrane metallo-endopeptidase |
| Innate | Neutrophils | MNDA | myeloid cell nuclear differentiation antigen |
| Innate | Neutrophils | P2RY13 | purinergic receptor P2Y, G-protein coupled, 13 |

FIG. 8

| Class | CellType | GeneSymbol | Description |
|---|---|---|---|
| Innate | Neutrophils | PADI2 | peptidyl arginine deiminase, type II |
| Innate | Neutrophils | PGLYRP1 | peptidoglycan recognition protein 1 |
| Innate | Neutrophils | PI3 | peptidase inhibitor 3, skin-derived |
| Innate | Monocytes;Neutrophils | PTGS2 | prostaglandin-endoperoxide synthase 2 (prostaglandin G/H synthase ad cyclooxygenase |
| Innate | Neutrophils | PYGL | phosphorylase, glycogen, liver |
| Innate | Monocytes;Neutrophils | S100A8 | S100 calcium binding protein A8 |
| Innate | Monocytes;Neutrophils | S100A9 | S100 calcium binding protein A9 |
| Innate | Monocytes;Neutrophils | S100P | S100 calcium binding protein P |
| Innate | Neutrophils | SERPINA1 | serpin peptidase inhibitor, clade A (alpha-1 antiproteinase, antitrypsin), member 1 |
| Innate | Neutrophils | STEAP4 | STEAP family member 4 |
| Innate | Neutrophils | TLR8 | toll-like receptor 8 |
| Innate | Monocytes;Neutrophils | TNFAIP2 | tumor necrosis factor, alpha-induced protein 2 |
| Innate | Neutrophils | TNFRSF10C | tumor necrosis factor receptor superfamily, member 10c, decoy without an intracellular domain |
| Innate | Neutrophils | TREM1 | triggering receptor expressed on myeloid cells 1 |
| Innate | Monocytes | ARHGEF10L | Rho guanine nucleotide exchange factor (GEF) 10-like |
| Innate | Monocytes | ASGR2 | asialoglycoprotein receptor 2 |
| Innate | Monocytes | CD14 | CD14 molecule |
| Innate | Monocytes | CD163 | CD163 molecule |
| Innate | Monocytes | CD300E | CD300e molecule |
| Innate | Monocytes | CD36 | CD36 molecule (thrombospondin receptor) |
| Innate | Monocytes | CD68 | CD68 molecule |
| Innate | Monocytes | CD86 | CD68 molecule |
| Innate | Monocytes | CPVL | carboxypeptidase, vitellogenic-like |
| Innate | Monocytes | CSF1R | colony stimulating factor 1 receptor |
| Innate | Monocytes | CST3 | cystatin C |
| Innate | Monocytes | CXCL2 | chemokine (C-X-C motif) ligand 2 |
| Innate | Monocytes | CYBB | cytochrome b-245, beta polypeptide |
| Innate | Monocytes | CYP1B1 | cytochrome P450, family 1, subfamily B, polypeptide 1 |
| Innate | Monocytes | EGR1 | early growth response 1 |
| Innate | Monocytes | EGR2 | early growth response 2 |
| Innate | Monocytes | EPB41L3 | erythrocyte membrane protein band 4.1-like 3 |
| Innate | Monocytes | EREG | epiregulin |
| Innate | Monocytes | FAM198B | family with sequence similarity 198, member B |
| Innate | Monocytes | FCAR | Fc fragment of IgA, receptor for |
| Innate | Monocytes | FCN1 | ficolin (collagen/fibrinogen domain containing) 1 |
| Innate | Monocytes | HBEGF | heparin-binding EGF-like growth factor |
| Innate | Monocytes | IL1B | interleukin 1, beta |

FIG. 8 (Cont.)

| Class | CellType | GeneSymbol | Description |
|---|---|---|---|
| Innate | Monocytes | KIAA1598 | KIAA1598 |
| Innate | Monocytes | LGALS2 | lectin, galactoside-binding, soluble, 2 |
| Innate | Monocytes | LILRB2 | leukocyte immunoglobulin-like receptor, subfamily B (with TM and ITIM domains), member 2 |
| Innate | Monocytes | LILRB4 | leukocyte immunoglobulin-like receptor, subfamily B (with TM and ITIM domains), member 4 |
| Innate | Monocytes | LRP1 | low density lipoprotein receptor-related protein 1 |
| Innate | Monocytes | LYZ | lysozyme |
| Innate | Monocytes | MAFB | v-maf avian musculoaponeurotic fibrosarcoma oncogene homolog |
| Innate | Monocytes | MPEG1 | macrophage expressed 1 |
| Innate | Monocytes | MS4A6A | membrane-spanning 4-domains, subfamily A, member 6A |
| Innate | Monocytes | MYOF | myoferlin |
| Innate | Monocytes | NID1 | nidogen 1 |
| Innate | Monocytes | PLAUR | plasminogen activator, urokinase receptor |
| Innate | Monocytes | PLBD1 | phospholipase B domain containing 1 |
| Innate | Monocytes | PLXNB2 | plexin B2 |
| Innate | Monocytes | SIGLEC1 | sialic acid binding Ig-like lectin 1, sialoadhesin |
| Innate | Monocytes | STAB1 | stabilin 1 |
| Innate | Monocytes | TGFBI | transforming growth factor, beta-induced, 68kDa |
| Innate | Monocytes | TMEM176A | transmembrane protein 176A |
| Innate | Monocytes | TMEM176B | transmembrane protein 176B |
| Innate | Monocytes | TRIB1 | tribbles pseudokinase 1 |
| Innate | Monocytes | VCAN | versican |
| Adaptive | B-cells | AFF3 | AF4/FMR2 family, member 3 |
| Adaptive | B-cells | BANK1 | B-cell scaffold protein with ankyrin repeats 1 |
| Adaptive | B-cells | BCL11A | B-cell CLL/lymphoma 11A (zinc finger protein) |
| Adaptive | B-cells | BCL7A | B-cell CLL/lymphoma 7A |
| Adaptive | B-cells | BLK | BLK proto-oncogene, Src family tyrosine kinase |
| Adaptive | B-cells | BLNK | B-cell linker |
| Adaptive | B-cells | CD19 | CD19 molecule |
| Adaptive | B-cells | CD22 | CD22 molecule |
| Adaptive | B-cells | CD79A | CD79a molecule, immunoglobulin-associated alpha |
| Adaptive | B-cells | CLEC17A | C-type lectin domain family 17, member A |
| Adaptive | B-cells | CNTNAP2 | contactin associated protein-like 2 |
| Adaptive | B-cells | COBLL1 | cordon-bleu WH2 repeat protein-like 1 |
| Adaptive | B-cells | COL19A1 | collagen, type XIX, alpha 1 |
| Adaptive | B-cells | COL4A3 | collagen, type IV, alpha 3 (Goodpasture antigen) |
| Adaptive | B-cells | CPNE5 | copine V |
| Adaptive | B-cells | DENND5B | DENN/MADD domain containing 5B |

FIG. 8 (Cont.)

| Class | CellType | GeneSymbol | Description |
|---|---|---|---|
| Adaptive | B-cells | EBF1 | early B-cell factor 1 |
| Adaptive | B-cells | FAM129C | family with sequence similarity 129, member C |
| Adaptive | B-cells | FCER2 | Fc fragment of IgE, low affinity II, receptor for (CD23) |
| Adaptive | B-cells | FCRL1 | Fc receptor-like 1 |
| Adaptive | B-cells | FCRL2 | Fc receptor-like 2 |
| Adaptive | B-cells | FCRL5 | Fc receptor-like 5 |
| Adaptive | B-cells | FCRLA | Fc receptor-like A |
| Adaptive | B-cells | HLA-DOA | major histocompatibility complex, class II, DO alpha |
| Adaptive | B-cells | IGJ | immunoglobulin J polypeptide, linker protein for immunoglobulin alpha and mu polypeptides |
| Adaptive | B-cells | IL6 | interleukin 6 |
| Adaptive | B-cells | KCNH8 | potassium voltage-gated channel, subfamily H (eag-related), member 8 |
| Adaptive | B-cells | KLHL14 | kelch-like family member 14 |
| Adaptive | B-cells | LINC00494 | long intergenic non-protein coding RNA 494 |
| Adaptive | B-cells | LINC00926 | long intergenic non-protein coding RNA 926 |
| Adaptive | B-cells | LOC100507616 | uncharacterized LOC100507616 |
| Adaptive | B-cells | MACROD2 | MACRO domain containing 2 |
| Adaptive | B-cells | MS4A1 | membrane-spanning 4-domains, subfamily A, member 1 |
| Adaptive | B-cells | MZB1 | marginal zone B and B1 cell-specific protein |
| Adaptive | B-cells | OSBPL10 | oxysterol binding protein-like 10 |
| Adaptive | B-cells | PAX5 | paired box 5 |
| Adaptive | B-cells | PCDH9 | protocadherin 9 |
| Adaptive | B-cells | PEG10 | paternally expressed 10 |
| Adaptive | B-cells | PLEKHG1 | pleckstrin homology domain containing, family G (with RhoGef domain) member 1 |
| Adaptive | B-cells | SCN3A | sodium channel, voltage-gated, type III, alpha subunit |
| Adaptive | B-cells | SLC38A11 | solute carrier family 38, member 11 |
| Adaptive | B-cells | SYNPO | synaptopodin |
| Adaptive | B-cells | TBC1D9 | TBC1 domain family, member 9 (with GRAM domain) |
| Adaptive | B-cells | TCL1A | T-cell leukemia/lymphoma 1A |
| Adaptive | B-cells | TCL6 | T-cell leukemia/lymphoma 6 (non-protein coding) |
| Adaptive | B-cells | TNFRSF13B | tumor necrosis factor receptor superfamily, member 13B |
| Adaptive | B-cells | TNFRSF13C | tumor necrosis factor receptor superfamily, member 13C |
| Adaptive | B-cells | TSPAN13 | tetraspanin 13 |
| Adaptive | B-cells | VPREB3 | pre-B lymphocyte 3 |
| Adaptive | B-cells | WDFY4 | WDFY family member 4 |
| Adaptive | CD4 | ADTRP | androgen-dependent TFPI-regulating protein |
| Adaptive | CD4 | ALS2CL | ALS2 C-terminal like |
| Adaptive | CD4 | AQP3 | aquaporin 3 (Gill blood group) |

FIG. 8 (Cont.)

| Class | CellType | GeneSymbol | Description |
|---|---|---|---|
| Adaptive | CD4;CD8 | BCL11B | B-cell CLL/lymphoma 11B (zinc finger protein) |
| Adaptive | CD4 | C14orf64 | chromosome 14 open reading frame 64 |
| Adaptive | CD4 | CACNA1I | calcium channel, voltage-dependent, T type, alpha 1I subunit |
| Adaptive | CD4;CD8 | CAMK4 | calcium/calmodulin-dependent protein kinase IV |
| Adaptive | CD4 | CCR4 | chemokine (C-C motif) receptor 4 |
| Adaptive | CD4 | CCR7 | chemokine (C-C motif) receptor 7 |
| Adaptive | CD4;CD8 | CD2 | CD2 molecule |
| Adaptive | CD4;CD8 | CD28 | CD28 molecule |
| Adaptive | CD4;CD8 | CD3D | CD3d molecule, delta (CD3-TCR complex) |
| Adaptive | CD4;CD8 | CD3E | CD3e molecule, epsilon (CD3-TCR complex) |
| Adaptive | CD4 | CD4 | CD4 molecule |
| Adaptive | CD4 | CD40LG | CD40 ligand |
| Adaptive | CD4;CD8 | CD5 | CD5 molecule |
| Adaptive | CD4;CD8 | CD6 | CD6 molecule |
| Adaptive | CD4;CD8 | CHRM3-AS2 | CHRM3 antisense RNA 2 |
| Adaptive | CD4 | CTLA4 | cytotoxic T-lymphocyte-associated protein 4 |
| Adaptive | CD4;CD8 | DPP4 | dipeptidyl-peptidase 4 |
| Adaptive | CD4 | EDAR | ectodysplasin A receptor |
| Adaptive | CD4 | EPHX2 | epoxide hydrolase 2, cytoplasmic |
| Adaptive | CD4 | FAM153A | family with sequence similarity 153, member A |
| Adaptive | CD4 | FHIT | fragile histidine triad |
| Adaptive | CD4 | FOXP3 | forkhead box P3 |
| Adaptive | CD4;CD8 | GATA3 | GATA binding protein 3 |
| Adaptive | CD4 | ICOS | inducible T-cell co-stimulator |
| Adaptive | CD4;CD8 | IL7R | interleukin 7 receptor |
| Adaptive | CD4;CD8 | INPP4B | inositol polyphosphate-4-phosphatase, type II, 105kDa |
| Adaptive | CD4;CD8 | ITK | IL2-inducible T-cell kinase |
| Adaptive | CD4;CD8 | LEF1 | lymphoid enhancer-binding factor 1 |
| Adaptive | CD4;CD8 | LINC00861 | long intergenic non-protein coding RNA 861 |
| Adaptive | CD4;CD8 | MAL | mal, T-cell differentiation protein |
| Adaptive | CD4;CD8 | NELL2 | NEL-like 2 (chicken) |
| Adaptive | CD4 | PRKCQ-AS1 | PRKCQ antisense RNA 1 |
| Adaptive | CD4;CD8 | RASGRF2 | Ras protein-specific guanine nucleotide-releasing factor 2 |
| Adaptive | CD4 | RCAN3 | RCAN family member 3 |
| Adaptive | CD4;CD8 | RNF157 | ring finger protein 157 |
| Adaptive | CD4 | RTKN2 | rhotekin 2 |
| Adaptive | CD4;CD8 | SIRPG | signal-regulatory protein gamma |
| Adaptive | CD4 | TBC1D4 | TBC1 domain family, member 4 |
| Adaptive | CD4;CD8 | TC2N | tandem C2 domains, nuclear |
| Adaptive | CD4;CD8 | TCF7 | transcription factor 7 (T-cell specific, HMG-box) |

FIG. 8 (Cont.)

| Class | CellType | GeneSymbol | Description |
|---|---|---|---|
| Adaptive | CD4;CD8 | THEMIS | thymocyte selection associated |
| Adaptive | CD4;CD8 | TNFRSF25 | tumor necrosis factor receptor superfamily, member 25 |
| Adaptive | CD4;CD8 | TRABD2A | TraB domain containing 2A |
| Adaptive | CD4 | TRAT1 | T cell receptor associated transmembrane adaptor 1 |
| Adaptive | CD4 | TSHZ2 | teashirt zinc finger homeobox 2 |
| Adaptive | CD4 | TSPAN18 | tetraspanin 18 |
| Adaptive | CD4;CD8 | UBASH3A | ubiquitin associated and SH3 domain containing A |
| Adaptive | CD8 | APBA2 | amyloid beta (A4) precursor protein-binding, family A, member 2 |
| Adaptive | CD8;NK | CCL5 | chemokine (C-C motif) ligand 5 |
| Adaptive | CD8 | CD3G | CD3g molecule, gamma (CD3-TCR complex) |
| Adaptive | CD8 | CD8A | CD8a molecule |
| Adaptive | CD8 | COL6A2 | collagen, type VI, alpha 2 |
| Adaptive | CD8;NK | CTSW | cathepsin W |
| Adaptive | CD8;NK | FCRL6 | Fc receptor-like 6 |
| Adaptive | CD8 | FLT4 | fms-related tyrosine kinase 4 |
| Adaptive | CD8;NK | GNLY | granulysin |
| Adaptive | CD8;NK | GZMA | granzyme A (granzyme 1, cytotoxic T-lymphocyte-associated serine esterase 3) |
| Adaptive | CD8;NK | GZMH | granzyme H (cathepsin G-like 2, protein h-CCPX) |
| Adaptive | CD8 | GZMK | granzyme K (granzyme 3; tryptase II) |
| Adaptive | CD8;NK | IL2RB | interleukin 2 receptor, beta |
| Adaptive | CD8 | LAG3 | lymphocyte-activation gene 3 |
| Adaptive | CD8 | NPDC1 | neural proliferation, differentiation and control, 1 |
| Adaptive | CD8 | PLXDC1 | plexin domain containing 1 |
| Adaptive | CD8;NK | PRF1 | perforin 1 (pore forming protein) |
| Adaptive | CD8 | RORA | RAR-related orphan receptor A |
| Adaptive | CD8 | SLC4A10 | solute carrier family 4, sodium bicarbonate transporter, member 10 |
| Adaptive | CD8;NK | TGFBR3 | transforming growth factor, beta receptor III |
| Adaptive | CD8 | TTC16 | tetratricopeptide repeat domain 16 |
| Adaptive | CD8;NK | ZAP70 | zeta-chain (TCR) associated protein kinase 70kDa |
| Adaptive | CD8 | ZNF683 | zinc finger protein 683 |
| Adaptive | NK | ADAMTS10 | ADAM metallopeptidase with thrombospondin type 1 motif, 10 |
| Adaptive | NK | B3GAT1 | beta-1,3-glucuronyltransferase 1 |
| Adaptive | NK | B3GNT7 | UDP-GlcNAc:betaGal beta-1,3-N-acetylglucosaminyltransferase 7 |
| Adaptive | NK | BNC2 | basonuclin 2 |

FIG. 8 (Cont.)

| Class | CellType | GeneSymbol | Description |
|---|---|---|---|
| Adaptive | NK | C1orf21 | chromosome 1 open reading frame 21 |
| Adaptive | NK | CD160 | CD160 molecule |
| Adaptive | NK | CD247 | CD247 molecule |
| Adaptive | NK | CLIC3 | chloride intracellular channel 3 |
| Adaptive | NK | DTHD1 | death domain containing 1 |
| Adaptive | NK | FAT4 | FAT atypical cadherin 4 |
| Adaptive | NK | FGFBP2 | fibroblast growth factor binding protein 2 |
| Adaptive | NK | GPR56 | G protein-coupled receptor 56 |
| Adaptive | NK | GZMB | granzyme B (granzyme 2, cytotoxic T-lymphocyte-associated serine esterase 1) |
| Adaptive | NK | HDC | histidine decarboxylase |
| Adaptive | NK | HOPX | HOP homeobox |
| Adaptive | NK | KIR3DX1 | killer cell immunoglobulin-like receptor, three domains, X1 |
| Adaptive | NK | KLRB1 | killer cell lectin-like receptor subfamily B, member 1 |
| Adaptive | NK | KLRC1 | killer cell lectin-like receptor subfamily C, member 1 |
| Adaptive | NK | KLRD1 | killer cell lectin-like receptor subfamily D, member 1 |
| Adaptive | NK | KLRF1 | killer cell lectin-like receptor subfamily F, member 1 |
| Adaptive | NK | LGR6 | leucine-rich repeat containing G protein-coupled receptor 6 |
| Adaptive | NK | LINC00299 | long intergenic non-protein coding RNA 299 |
| Adaptive | NK | MATK | megakaryocyte-associated tyrosine kinase |
| Adaptive | NK | MLC1 | megalencephalic leukoencephalopathy with subcortical cysts 1 |
| Adaptive | NK | MMP23B | matrix metallopeptidase 23B |
| Adaptive | NK | NCAM1 | neural cell adhesion molecule 1 |
| Adaptive | NK | NCR1 | natural cytotoxicity triggering receptor 1 |
| Adaptive | NK | NKG7 | natural killer cell granule protein 7 |
| Adaptive | NK | NMUR1 | neuromedin U receptor 1 |
| Adaptive | NK | PDGFD | platelet derived growth factor D |
| Adaptive | NK | PDGFRB | platelet-derived growth factor receptor, beta polypeptide |
| Adaptive | NK | PDZD4 | PDZ domain containing 4 2 |
| Adaptive | NK | PRSS23 | protease, serine, 23 |
| Adaptive | NK | PTGDR | prostaglandin D2 receptor (DP) |
| Adaptive | NK | PTGDS | prostaglandin D2 synthase 21kDa (brain) |
| Adaptive | NK | RNF165 | ring finger protein 165 |
| Adaptive | NK | S1PR5 | sphingosine-1-phosphate receptor 5 |
| Adaptive | NK | SH2D1B | SH2 domain containing 1B |
| Adaptive | NK | SH2D2A | SH2 domain containing 2A |
| Adaptive | NK | TBX21 | T-box 21 |

FIG. 8 (Cont.)

| Class | CellType | GeneSymbol | Description |
|---|---|---|---|
| Innate | Neutrophils | AATK | apoptosis-associated tyrosine kinase |
| Innate | Neutrophils | ACSL1 | acyl-CoA synthetase long-chain family member 1 |
| Innate | Neutrophils | ADM | adrenomedullin |
| Innate | Neutrophils | ALPL | alkaline phosphatase, liver/bone/kidney |
| Innate | Monocytes;Neutrophils | ANPEP | alanyl (membrane) aminopeptidase |
| Innate | Neutrophils | ANXA3 | annexin A3 |
| Innate | Neutrophils | AOC2 | amine oxidase, copper containing 2 (retina-specific) |
| Innate | Neutrophils | AOC3 | amine oxidase, copper containing 3 |
| Innate | Neutrophils | AQP9 | aquaporin 9 |
| Innate | Monocytes;Neutrophils | ARHGEF40 | Rho guanine nucleotide exchange factor (GEF) 40 |
| Innate | Neutrophils | B3GNT5 | UDP-GlcNAc:betaGal beta-1,3-N-acetylglucosaminyltransferase 5 |
| Innate | Neutrophils | B3GNT8 | UDP-GlcNAc:betaGal beta-1,3-N-acetylglucosaminyltransferase 8 |
| Innate | Neutrophils | BASP1 | brain abundant, membrane attached signal protein 1 |
| Innate | Neutrophils | BEND7 | BEN domain containing 7 |
| Innate | Neutrophils | BMX | BMX non-receptor tyrosine kinase |
| Innate | Monocytes;Neutrophils | BST1 | bone marrow stromal cell antigen 1 |
| Innate | Neutrophils | BTNL8 | butyrophilin-like 8 |
| Innate | Monocytes;Neutrophils | C5AR1 | complement component 5a receptor 1 |
| Innate | Neutrophils | C5AR2 | complement component 5a receptor 2 |
| Innate | Neutrophils | CA4 | carbonic anhydrase IV |
| Innate | Neutrophils | CACNA1E | calcium channel, voltage-dependent, R type, alpha 1E subunit |
| Innate | Neutrophils | CAMP | cathelicidin antimicrobial peptide |
| Innate | Neutrophils | CASP5 | caspase 5, apoptosis-related cysteine peptidase |
| Innate | Neutrophils | CBS | cystathionine-beta-synthase |
| Innate | Neutrophils | CCDC147-AS1 | CCDC147 antisense RNA 1 (head to head) |
| Innate | Neutrophils | CCNJL | cyclin J-like |
| Innate | Neutrophils | CCR3 | chemokine (C-C motif) receptor 3 |
| Innate | Neutrophils | CD177 | CD177 molecule |
| Innate | Neutrophils | CDA | cytidine deaminase |
| Innate | Neutrophils | CEACAM1 | carcinoembryonic antigen-related cell adhesion molecule 1 (biliary glycoprotein) |
| Innate | Neutrophils | CEACAM3 | carcinoembryonic antigen-related cell adhesion molecule 3 |

FIG. 9

| Class | CellType | GeneSymbol | Description |
|---|---|---|---|
| Innate | Neutrophils | CEACAM4 | carcinoembryonic antigen-related cell adhesion molecule 4 |
| Innate | Neutrophils | CEP19 | centrosomal protein 19kDa |
| Innate | Neutrophils | CHI3L1 | chitinase 3-like 1 (cartilage glycoprotein-39) |
| Innate | Neutrophils | CHST15 | carbohydrate (N-acetylgalactosamine 4-sulfate 6-O) sulfotransferase 15 |
| Innate | Neutrophils | CLEC4D | C-type lectin domain family 4, member D |
| Innate | Neutrophils | CLEC4E | C-type lectin domain family 4, member E |
| Innate | Monocytes;Neutrophils | CLEC7A | C-type lectin domain family 7, member A |
| Innate | Neutrophils | CMTM2 | CKLF-like MARVEL transmembrane domain containing 2 |
| Innate | Neutrophils | CNTNAP3 | contactin associated protein-like 3 |
| Innate | Neutrophils | CRISPLD2 | cysteine-rich secretory protein LCCL domain containing 2 |
| Innate | Neutrophils | CSF2RA | colony stimulating factor 2 receptor, alpha, low-affinity (granulocyte-macrophage) |
| Innate | Neutrophils | CSF2RB | colony stimulating factor 2 receptor, beta, low-affinity (granulocyte-macrophage) |
| Innate | Monocytes;Neutrophils | CSF3R | colony stimulating factor 3 receptor (granulocyte) |
| Innate | Neutrophils | CXCL1 | chemokine (C-X-C motif) ligand 1 (melanoma growth stimulating activity, alpha) |
| Innate | Monocytes;Neutrophils | CXCL8 | chemokine (C-X-C motif) ligand 8 |
| Innate | Neutrophils | CXCR1 | chemokine (C-X-C motif) receptor 1 |
| Innate | Neutrophils | CXCR2 | chemokine (C-X-C motif) receptor 2 |
| Innate | Neutrophils | CYP4F3 | cytochrome P450, family 4, subfamily F, polypeptide 3 |
| Innate | Neutrophils | DAAM2 | dishevelled associated activator of morphogenesis 2 |
| Innate | Neutrophils | DGAT2 | diacylglycerol O-acyltransferase 2 |
| Innate | Neutrophils | DHRS9 | dehydrogenase/reductase (SDR family) member 9 |
| Innate | Neutrophils | DOCK4 | dedicator of cytokinesis 4 |
| Innate | Neutrophils | DOCK5 | dedicator of cytokinesis 5 |
| Innate | Neutrophils | DSC2 | desmocollin 2 |
| Innate | Neutrophils | DYSF | dysferlin |
| Innate | Neutrophils | EMR3 | egf-like module containing, mucin-like, hormone receptor-like 3 |
| Innate | Neutrophils | EPHB1 | EPH receptor B1 |
| Innate | Neutrophils | F2RL1 | coagulation factor II (thrombin) receptor-like 1 |
| Innate | Neutrophils | FBXL13 | F-box and leucine-rich repeat protein 13 |
| Innate | Monocytes;Neutrophils | FCAR | Fc fragment of IgA, receptor for |
| Innate | Neutrophils | FCGR2A | Fc fragment of IgG, low affinity IIa, receptor (CD32) |
| Innate | Neutrophils | FCGR3B | Fc fragment of IgG, low affinity IIIb, receptor (CD16b) |

FIG. 9 (Cont.)

| Class | CellType | GeneSymbol | Description |
|---|---|---|---|
| Innate | Neutrophils | FFAR2 | free fatty acid receptor 2 |
| Innate | Neutrophils | FPR1 | formyl peptide receptor 1 |
| Innate | Neutrophils | FPR2 | formyl peptide receptor 2 |
| Innate | Monocytes;Neutrophils | G0S2 | G0/G1 switch 2 |
| Innate | Neutrophils | GALNT14 | polypeptide N-acetylgalactosaminyltransferase 14 |
| Innate | Neutrophils | GCA | grancalcin, EF-hand calcium binding protein |
| Innate | Monocytes;Neutrophils | GLT1D1 | glycosyltransferase 1 domain containing 1 |
| Innate | Neutrophils | GPR27 | G protein-coupled receptor 27 |
| Innate | Neutrophils | GPR97 | G protein-coupled receptor 97 |
| Innate | Neutrophils | HAL | histidine ammonia-lyase |
| Innate | Neutrophils | HCAR2 | hydroxycarboxylic acid receptor 2 |
| Innate | Neutrophils | HCAR3 | hydroxycarboxylic acid receptor 3 |
| Innate | Monocytes;Neutrophils | HCK | HCK proto-oncogene, Src family tyrosine kinase |
| Innate | Neutrophils | HECW2 | HECT, C2 and WW domain containing E3 ubiquitin protein ligase 2 |
| Innate | Neutrophils | HIST2H2BF | histone cluster 2, H2bf |
| Innate | Neutrophils | HSPA6 | heat shock 70kDa protein 6 (HSP70B') |
| Innate | Neutrophils | IFIT1 | interferon-induced protein with tetratricopeptide repeats 1 |
| Innate | Neutrophils | IFIT2 | interferon-induced protein with tetratricopeptide repeats 2 |
| Innate | Neutrophils | IFIT3 | interferon-induced protein with tetratricopeptide repeats 3 |
| Innate | Neutrophils | IGSF6 | immunoglobulin superfamily, member 6 |
| Innate | Neutrophils | IL13RA1 | interleukin 13 receptor, alpha 1 |
| Innate | Neutrophils | IL1R1 | interleukin 1 receptor, type I |
| Innate | Neutrophils | IL1R2 | interleukin 1 receptor, type II |
| Innate | Neutrophils | IL1RN | interleukin 1 receptor antagonist |
| Innate | Neutrophils | KAZN | kazrin, periplakin interacting protein |
| Innate | Neutrophils | KCNJ15 | potassium inwardly-rectifying channel, subfamily J, member 15 |
| Innate | Neutrophils | KCNJ2 | potassium inwardly-rectifying channel, subfamily J, member 2 |
| Innate | Neutrophils | KIAA0319 | KIAA0319 |
| Innate | Neutrophils | KIAA1257 | KIAA1257 |
| Innate | Neutrophils | KREMEN1 | kringle containing transmembrane protein 1 |
| Innate | Neutrophils | KRT23 | keratin 23 (histone deacetylase inducible) |
| Innate | Neutrophils | KY | kyphoscoliosis peptidase |
| Innate | Neutrophils | LCN2 | lipocalin 2 |
| Innate | Neutrophils | LGALSL | lectin, galactoside-binding-like |

FIG. 9 (Cont.)

| Class | CellType | GeneSymbol | Description |
|---|---|---|---|
| Innate | Monocytes;Neutrophils | LILRA1 | leukocyte immunoglobulin-like receptor, subfamily A (with TM domain), member 1 |
| Innate | Monocytes;Neutrophils | LILRA2 | leukocyte immunoglobulin-like receptor, subfamily A (with TM domain), member 2 |
| Innate | Monocytes;Neutrophils | LILRA5 | leukocyte immunoglobulin-like receptor, subfamily A (with TM domain), member 5 |
| Innate | Monocytes;Neutrophils | LILRA6 | leukocyte immunoglobulin-like receptor, subfamily A (with TM domain), member 6 |
| Innate | Monocytes;Neutrophils | LILRB2 | leukocyte immunoglobulin-like receptor, subfamily B (with TM and ITIM domains), member 2 |
| Innate | Neutrophils | LILRB3 | leukocyte immunoglobulin-like receptor, subfamily B (with TM and ITIM domains), member 3 |
| Innate | Neutrophils | LIN7A | lin-7 homolog A (C. elegans) |
| Innate | Neutrophils | LINC00211 | long intergenic non-protein coding RNA 211 |
| Innate | Neutrophils | LINC01270 | long intergenic non-protein coding RNA 1270 |
| Innate | Neutrophils | LINC01506 | long intergenic non-protein coding RNA 1506 |
| Innate | Neutrophils | LOC100128770 | uncharacterized LOC100128770 |
| Innate | Neutrophils | LOC100289473 | cytoskeleton associated protein 2-like pseudogene |
| Innate | Neutrophils | LOC101928595 | uncharacterized LOC101928595 |
| Innate | Neutrophils | LOC101928670 | uncharacterized LOC101928670 |
| Innate | Neutrophils | LOC102724231 | uncharacterized LOC102724231 |
| Innate | Neutrophils | LOC643072 | uncharacterized LOC643072 |
| Innate | Neutrophils | LOC93432 | maltase-glucoamylase (alpha-glucosidase) |
| Innate | Neutrophils | LPCAT2 | lysophosphatidylcholine acyltransferase 2 |
| Innate | Neutrophils | LRG1 | leucine-rich alpha-2-glycoprotein 1 |
| Innate | Neutrophils | LRRC25 | leucine rich repeat containing 25 |
| Innate | Neutrophils | LRRC4 | leucine rich repeat containing 4 |
| Innate | Neutrophils | LRRK2 | leucine-rich repeat kinase 2 |
| Innate | Neutrophils | LTF | lactotransferrin |
| Innate | Neutrophils | LUCAT1 | lung cancer associated transcript 1 (non-protein coding) |
| Innate | Neutrophils | MAK | male germ cell-associated kinase |
| Innate | Neutrophils | MANSC1 | MANSC domain containing 1 |
| Innate | Neutrophils | MBOAT2 | membrane bound O-acyltransferase domain containing 2 |
| Innate | Neutrophils | MEFV | Mediterranean fever |
| Innate | Neutrophils | MGAM | maltase-glucoamylase (alpha-glucosidase) |
| Innate | Neutrophils | MIR223 | microRNA 223 |
| Innate | Neutrophils | MME | membrane metallo-endopeptidase |
| Innate | Neutrophils | MMP25 | matrix metallopeptidase 25 |
| Innate | Neutrophils | MMP8 | matrix metallopeptidase 8 (neutrophil collagenase) |
| Innate | Neutrophils | MMP9 | matrix metallopeptidase 9 (gelatinase B, 92kDa gelatinase, 92kDa type IV collagenase) |

FIG. 9 (Cont.)

| Class | CellType | GeneSymbol | Description |
|---|---|---|---|
| Innate | Monocytes;Neutrophils | MNDA | myeloid cell nuclear differentiation antigen |
| Innate | Neutrophils | MRVI1 | murine retrovirus integration site 1 homolog |
| Innate | Neutrophils | NAMPT | nicotinamide phosphoribosyltransferase |
| Innate | Monocytes;Neutrophils | NCF2 | neutrophil cytosolic factor 2 |
| Innate | Neutrophils | NECAB2 | N-terminal EF-hand calcium binding protein 2 |
| Innate | Monocytes;Neutrophils | NFAM1 | NFAT activating protein with ITAM motif 1 |
| Innate | Neutrophils | NFE2 | nuclear factor, erythroid 2 |
| Innate | Neutrophils | NLRP12 | NLR family, pyrin domain containing 12 |
| Innate | Neutrophils | NOV | nephroblastoma overexpressed |
| Innate | Neutrophils | NSUN7 | NOP2/Sun domain family, member 7 |
| Innate | Neutrophils | ORM1 | orosomucoid 1 |
| Innate | Neutrophils | P2RY13 | purinergic receptor P2Y, G-protein coupled, 13 |
| Innate | Neutrophils | PADI2 | peptidyl arginine deiminase, type II |
| Innate | Neutrophils | PADI4 | peptidyl arginine deiminase, type IV |
| Innate | Neutrophils | PANX2 | pannexin 2 |
| Innate | Neutrophils | PGLYRP1 | peptidoglycan recognition protein 1 |
| Innate | Neutrophils | PHOSPHO1 | phosphatase, orphan 1 |
| Innate | Neutrophils | PI3 | peptidase inhibitor 3, skin-derived |
| Innate | Neutrophils | PLB1 | phospholipase B1 |
| Innate | Monocytes;Neutrophils | PLBD1 | phospholipase B domain containing 1 |
| Innate | Neutrophils | PLIN4 | perilipin 4 |
| Innate | Neutrophils | PLIN5 | perilipin 5 |
| Innate | Neutrophils | PPL | periplakin |
| Innate | Neutrophils | PRDM5 | PR domain containing 5 |
| Innate | Neutrophils | PROK2 | prokineticin 2 |
| Innate | Neutrophils | PRRG4 | proline rich Gla (G-carboxyglutamic acid) 4 (transmembrane) |
| Innate | Monocytes;Neutrophils | PTAFR | platelet-activating factor receptor |
| Innate | Monocytes;Neutrophils | PTGS2 | prostaglandin-endoperoxide synthase 2 (prostaglandin G/H synthase and cyclooxygenase) |
| Innate | Monocytes;Neutrophils | PYGL | phosphorylase, glycogen, liver |
| Innate | Neutrophils | QPCT | glutaminyl-peptide cyclotransferase |
| Innate | Neutrophils | RASGRP4 | RAS guanyl releasing protein 4 |
| Innate | Neutrophils | RBM47 | RNA binding motif protein 47 |
| Innate | Neutrophils | RGS18 | regulator of G-protein signaling 18 |
| Innate | Neutrophils | ROPN1L | rhophilin associated tail protein 1-like |

FIG. 9 (Cont.)

| Class | CellType | GeneSymbol | Description |
|---|---|---|---|
| Innate | Monocytes;Neutrophils | S100A12 | S100 calcium binding protein A12 |
| Innate | Monocytes;Neutrophils | S100A8 | S100 calcium binding protein A8 |
| Innate | Monocytes;Neutrophils | S100A9 | S100 calcium binding protein A9 |
| Innate | Neutrophils | S100P | S100 calcium binding protein P |
| Innate | Monocytes;Neutrophils | SECTM1 | secreted and transmembrane 1 |
| Innate | Monocytes;Neutrophils | SERPINA1 | serpin peptidase inhibitor, clade A (alpha-1 antiproteinase, antitrypsin), member 1 |
| Innate | Neutrophils | SERPING1 | serpin peptidase inhibitor, clade G (C1 inhibitor), member 1 |
| Innate | Neutrophils | SIGLEC5 | sialic acid binding Ig-like lectin 5 |
| Innate | Neutrophils | SIPA1L2 | signal-induced proliferation-associated 1 like 2 |
| Innate | Monocytes;Neutrophils | SIRPA | signal-regulatory protein alpha |
| Innate | Neutrophils | SIRPB1 | signal-regulatory protein beta 1 |
| Innate | Monocytes;Neutrophils | SIRPB2 | signal-regulatory protein beta 2 |
| Innate | Monocytes;Neutrophils | SLC11A1 | solute carrier family 11 (proton-coupled divalent metal ion transporter), member 1 |
| Innate | Neutrophils | SLC22A4 | solute carrier family 22 (organic cation/zwitterion transporter), member 4 |
| Innate | Neutrophils | SLC26A8 | solute carrier family 26 (anion exchanger), member 8 |
| Innate | Monocytes;Neutrophils | SLC8A1 | solute carrier family 8 (sodium/calcium exchanger), member 1 |
| Innate | Neutrophils | SLPI | secretory leukocyte peptidase inhibitor |
| Innate | Monocytes;Neutrophils | SPI1 | Spi-1 proto-oncogene |
| Innate | Neutrophils | ST6GALNAC2 | ST6 (alpha-N-acetyl-neuraminyl-2,3-beta-galactosyl-1,3)-N-acetylgalactosaminide alpha-2,6-sialyltransferase 2 |
| Innate | Neutrophils | STEAP4 | STEAP family member 4 |
| Innate | Neutrophils | TGM3 | transglutaminase 3 |
| Innate | Neutrophils | THBD | thrombomodulin |
| Innate | Monocytes;Neutrophils | TLR4 | toll-like receptor 4 |
| Innate | Monocytes;Neutrophils | TLR8 | toll-like receptor 8 |
| Innate | Monocytes;Neutrophils | TNFAIP2 | tumor necrosis factor, alpha-induced protein 2 |
| Innate | Neutrophils | TNFAIP6 | tumor necrosis factor, alpha-induced protein 6 |

FIG. 9 (Cont.)

| Class | CellType | GeneSymbol | Description |
| --- | --- | --- | --- |
| Innate | Neutrophils | TNFRSF10C | tumor necrosis factor receptor superfamily, member 10c, decoy without an intracellular domain |
| Innate | Monocytes;Neutrophils | TREM1 | triggering receptor expressed on myeloid cells 1 |
| Innate | Neutrophils | TREML3P | triggering receptor expressed on myeloid cells-like 3, pseudogene |
| Innate | Neutrophils | TRPM6 | transient receptor potential cation channel, subfamily M, member 6 |
| Innate | Neutrophils | TSPAN16 | tetraspanin 16 |
| Innate | Neutrophils | VNN1 | vanin 1 |
| Innate | Neutrophils | VNN3 | vanin 3 |
| Innate | Neutrophils | WDFY3 | WD repeat and FYVE domain containing 3 |
| Innate | Neutrophils | WLS | wntless Wnt ligand secretion mediator |
| Innate | Monocytes | ABCC3 | ATP-binding cassette, sub-family C (CFTR/MRP), member 3 |
| Innate | Monocytes | ACPP | acid phosphatase, prostate |
| Innate | Monocytes | ADAMTSL4 | ADAMTS-like 4 |
| Innate | Monocytes | ADAP2 | ArfGAP with dual PH domains 2 |
| Innate | Monocytes | AIF1 | allograft inflammatory factor 1 |
| Innate | Monocytes | ALDH1A1 | aldehyde dehydrogenase 1 family, member A1 |
| Innate | Monocytes | ALDH2 | aldehyde dehydrogenase 2 family (mitochondrial) |
| Innate | Monocytes | ALDH3B1 | aldehyde dehydrogenase 3 family, member B1 |
| Innate | Monocytes | ARHGEF10L | Rho guanine nucleotide exchange factor (GEF) 10-like |
| Innate | Monocytes | ASGR1 | asialoglycoprotein receptor 1 |
| Innate | Monocytes | ASGR2 | asialoglycoprotein receptor 2 |
| Innate | Monocytes | ATF3 | activating transcription factor 3 |
| Innate | Monocytes | C19orf38 | chromosome 19 open reading frame 38 |
| Innate | Monocytes | CCDC149 | coiled-coil domain containing 149 |
| Innate | Monocytes | CCL3 | chemokine (C-C motif) ligand 3 |
| Innate | Monocytes | CCR1 | chemokine (C-C motif) receptor 1 |
| Innate | Monocytes | CD14 | CD14 molecule |
| Innate | Monocytes | CD163 | CD163 molecule |
| Innate | Monocytes | CD1D | CD1d molecule |
| Innate | Monocytes | CD300C | CD300c molecule |
| Innate | Monocytes | CD300E | CD300e molecule |
| Innate | Monocytes | CD300LB | CD300 molecule-like family member b |
| Innate | Monocytes | CD300LF | CD300 molecule-like family member f |
| Innate | Monocytes | CD33 | CD33 molecule |
| Innate | Monocytes | CD36 | CD36 molecule (thrombospondin receptor) |
| Innate | Monocytes | CD68 | CD68 molecule |
| Innate | Monocytes | CD86 | CD86 molecule |
| Innate | Monocytes | CD93 | CD93 molecule |
| Innate | Monocytes | CDKN1A | cyclin-dependent kinase inhibitor 1A (p21, Cip1) |

FIG. 9 (Cont.)

| Class | CellType | GeneSymbol | Description |
|---|---|---|---|
| Innate | Monocytes | CFD | complement factor D (adipsin) |
| Innate | Monocytes | CFP | complement factor properdin |
| Innate | Monocytes | CLEC10A | C-type lectin domain family 10, member A |
| Innate | Monocytes | CLEC12A | C-type lectin domain family 12, member A |
| Innate | Monocytes | CPVL | carboxypeptidase, vitellogenic-like |
| Innate | Monocytes | CSF1R | colony stimulating factor 1 receptor |
| Innate | Monocytes | CST3 | cystatin C |
| Innate | Monocytes | CSTA | cystatin A (stefin A) |
| Innate | Monocytes | CTSL | cathepsin L |
| Innate | Monocytes | CXCL2 | chemokine (C-X-C motif) ligand 2 |
| Innate | Monocytes | CYFIP1 | cytoplasmic FMR1 interacting protein 1 |
| Innate | Monocytes | CYP1B1 | cytochrome P450, family 1, subfamily B, polypeptide 1 cytochrome P450, family 27, subfamily A, polypeptide |
| Innate | Monocytes | CYP27A1 | 1 |
| Innate | Monocytes | CYP2S1 | cytochrome P450, family 2, subfamily S, polypeptide 1 |
| Innate | Monocytes | DAPK1 | death-associated protein kinase 1 |
| Innate | Monocytes | DMXL2 | Dmx-like 2 |
| Innate | Monocytes | DUSP6 | dual specificity phosphatase 6 |
| Innate | Monocytes | EGR1 | early growth response 1 |
| Innate | Monocytes | EGR2 | early growth response 2 |
| Innate | Monocytes | EGR3 | early growth response 3 |
| Innate | Monocytes | EMILIN2 | elastin microfibril interfacer 2 |
| Innate | Monocytes | EMP1 | epithelial membrane protein 1 |
| Innate | Monocytes | EPB41L3 | erythrocyte membrane protein band 4.1-like 3 |
| Innate | Monocytes | EPHB2 | EPH receptor B2 |
| Innate | Monocytes | EREG | epiregulin |
| Innate | Monocytes | F13A1 | coagulation factor XIII, A1 polypeptide |
| Innate | Monocytes | FAM129B | family with sequence similarity 129, member B |
| Innate | Monocytes | FAM198B | family with sequence similarity 198, member B |
| Innate | Monocytes | FAM20C | family with sequence similarity 20, member C |
| Innate | Monocytes | FBN2 | fibrillin 2 |
| Innate | Monocytes | FCER1G | Fc fragment of IgE, high affinity I, receptor for; gamma polypeptide |
| Innate | Monocytes | FCN1 | ficolin (collagen/fibrinogen domain containing) 1 |
| Innate | Monocytes | FOSL1 | FOS-like antigen 1 |
| Innate | Monocytes | FZD1 | frizzled class receptor 1 |
| Innate | Monocytes | GAS2L1 | growth arrest-specific 2 like 1 |
| Innate | Monocytes | GPBAR1 | G protein-coupled bile acid receptor 1 |
| Innate | Monocytes | HBEGF | heparin-binding EGF-like growth factor |
| Innate | Monocytes | HK3 | hexokinase 3 (white cell) |
| Innate | Monocytes | HMOX1 | heme oxygenase (decycling) 1 |
| Innate | Monocytes | HNMT | histamine N-methyltransferase |
| Innate | Monocytes | IFI30 | interferon, gamma-inducible protein 30 |

FIG. 9 (Cont.)

| Class | CellType | GeneSymbol | Description |
|---|---|---|---|
| Innate | Monocytes | IL1B | interleukin 1, beta |
| Innate | Monocytes | IQSEC2 | IQ motif and Sec7 domain 2 |
| Innate | Monocytes | IRAK3 | interleukin-1 receptor-associated kinase 3 |
| Innate | Monocytes | KCNMB1 | potassium large conductance calcium-activated channel, subfamily M, beta member 1 |
| Innate | Monocytes | KCTD12 | potassium channel tetramerization domain containing 12 |
| Innate | Monocytes | KIAA1598 | KIAA1598 |
| Innate | Monocytes | KLF4 | Kruppel-like factor 4 (gut) |
| Innate | Monocytes | KYNU | kynureninase |
| Innate | Monocytes | LAMB2 | laminin, beta 2 (laminin S) |
| Innate | Monocytes | LDLRAD3 | low density lipoprotein receptor class A domain containing 3 |
| Innate | Monocytes | LGALS2 | lectin, galactoside-binding, soluble, 2 |
| Innate | Monocytes | LILRA3 | leukocyte immunoglobulin-like receptor, subfamily A (without TM domain), member 3 |
| Innate | Monocytes | LILRB4 | leukocyte immunoglobulin-like receptor, subfamily B (with TM and ITIM domains), member 4 |
| Innate | Monocytes | LINC00877 | long intergenic non-protein coding RNA 877 |
| Innate | Monocytes | LOC101929911 | uncharacterized LOC101929911 |
| Innate | Monocytes | LOC284837 | uncharacterized LOC284837 |
| Innate | Monocytes | LRP1 | low density lipoprotein receptor-related protein 1 |
| Innate | Monocytes | LRP3 | low density lipoprotein receptor-related protein 3 |
| Innate | Monocytes | LTBR | lymphotoxin beta receptor (TNFR superfamily, member 3) |
| Innate | Monocytes | LYZ | lysozyme |
| Innate | Monocytes | MAFB | v-maf avian musculoaponeurotic fibrosarcoma oncogene homolog B |
| Innate | Monocytes | MARCKS | myristoylated alanine-rich protein kinase C substrate |
| Innate | Monocytes | MARCO | macrophage receptor with collagenous structure |
| Innate | Monocytes | MARVELD1 | MARVEL domain containing 1 |
| Innate | Monocytes | MGST1 | microsomal glutathione S-transferase 1 |
| Innate | Monocytes | MITF | microphthalmia-associated transcription factor |
| Innate | Monocytes | MPEG1 | macrophage expressed 1 |
| Innate | Monocytes | MRAS | muscle RAS oncogene homolog |
| Innate | Monocytes | MS4A14 | membrane-spanning 4-domains, subfamily A, member 14 |
| Innate | Monocytes | MS4A6A | membrane-spanning 4-domains, subfamily A, member 6A |
| Innate | Monocytes | MS4A7 | membrane-spanning 4-domains, subfamily A, member 7 |
| Innate | Monocytes | MSR1 | macrophage scavenger receptor 1 |
| Innate | Monocytes | MTMR11 | myotubularin related protein 11 |

FIG. 9 (Cont.)

| Class | CellType | GeneSymbol | Description |
|---|---|---|---|
| Innate | Monocytes | MYCL | v-myc avian myelocytomatosis viral oncogene lung carcinoma derived homolog |
| Innate | Monocytes | MYOF | myoferlin |
| Innate | Monocytes | NID1 | nidogen 1 |
| Innate | Monocytes | NLRP3 | NLR family, pyrin domain containing 3 |
| Innate | Monocytes | NR4A1 | nuclear receptor subfamily 4, group A, member 1 |
| Innate | Monocytes | NRG1 | neuregulin 1 |
| Innate | Monocytes | NRGN | neurogranin (protein kinase C substrate, RC3) |
| Innate | Monocytes | OAF | OAF homolog (Drosophila) |
| Innate | Monocytes | OSCAR | osteoclast associated, immunoglobulin-like receptor |
| Innate | Monocytes | PID1 | phosphotyrosine interaction domain containing 1 |
| Innate | Monocytes | PLA2G7 | phospholipase A2, group VII (platelet-activating factor acetylhydrolase, plasma) |
| Innate | Monocytes | PLAUR | plasminogen activator, urokinase receptor |
| Innate | Monocytes | PLXDC2 | plexin domain containing 2 |
| Innate | Monocytes | PLXNB2 | plexin B2 |
| Innate | Monocytes | PRAM1 | PML-RARA regulated adaptor molecule 1 |
| Innate | Monocytes | PTX3 | pentraxin 3, long |
| Innate | Monocytes | RAB32 | RAB32, member RAS oncogene family |
| Innate | Monocytes | RIN2 | Ras and Rab interactor 2 |
| Innate | Monocytes | RNASE2 | ribonuclease, RNase A family, 2 (liver, eosinophil-derived neurotoxin) |
| Innate | Monocytes | RPH3A | rabphilin 3A |
| Innate | Monocytes | RTN1 | reticulon 1 |
| Innate | Monocytes | RUSC2 | RUN and SH3 domain containing 2 |
| Innate | Monocytes | S1PR3 | sphingosine-1-phosphate receptor 3 |
| Innate | Monocytes | SASH1 | SAM and SH3 domain containing 1 |
| Innate | Monocytes | SERPINB2 | serpin peptidase inhibitor, clade B (ovalbumin), member 2 |
| Innate | Monocytes | SGK1 | serum/glucocorticoid regulated kinase 1 |
| Innate | Monocytes | SGMS2 | sphingomyelin synthase 2 |
| Innate | Monocytes | SIGLEC1 | sialic acid binding Ig-like lectin 1, sialoadhesin |
| Innate | Monocytes | SLC24A4 | solute carrier family 24 (sodium/potassium/calcium exchanger), member 4 |
| Innate | Monocytes | SLC46A2 | solute carrier family 46, member 2 |
| Innate | Monocytes | SLC7A7 | solute carrier family 7 (amino acid transporter light chain, y+L system), member 7 |
| Innate | Monocytes | SLC9A7P1 | solute carrier family 9, subfamily A (NHE7, cation proton antiporter 7), member 7 pseudogene 1 |
| Innate | Monocytes | SNAI1 | snail family zinc finger 1 |
| Innate | Monocytes | SORT1 | sortilin 1 |
| Innate | Monocytes | STAB1 | stabilin 1 |
| Innate | Monocytes | SULF2 | sulfatase 2 |

FIG. 9 (Cont.)

| Class | CellType | GeneSymbol | Description |
|---|---|---|---|
| Innate | Monocytes | TBC1D8 | TBC1 domain family, member 8 (with GRAM domain) |
| Innate | Monocytes | TCN2 | transcobalamin II |
| Innate | Monocytes | TFEC | transcription factor EC |
| Innate | Monocytes | TGFBI | transforming growth factor, beta-induced, 68kDa |
| Innate | Monocytes | THBS1 | thrombospondin 1 |
| Innate | Monocytes | TMEM150B | transmembrane protein 150B |
| Innate | Monocytes | TMEM176A | transmembrane protein 176A |
| Innate | Monocytes | TMEM176B | transmembrane protein 176B |
| Innate | Monocytes | TRIB1 | tribbles pseudokinase 1 |
| Innate | Monocytes | VCAN | versican |
| Innate | Monocytes | VEGFA | vascular endothelial growth factor A |
| Innate | Monocytes | VENTX | VENT homeobox |
| Innate | Monocytes | ZNF385A | zinc finger protein 385A |
| Innate | Monocytes | ZNF503 | zinc finger protein 503 |
| Innate | Monocytes | ZNF703 | zinc finger protein 703 |
| Adaptive | B-cells | ABCB4 | ATP-binding cassette, sub-family B (MDR/TAP), member 4 |
| Adaptive | B-cells | ADAM28 | ADAM metallopeptidase domain 28 |
| Adaptive | B-cells | ADD2 | adducin 2 (beta) |
| Adaptive | B-cells | AFF3 | AF4/FMR2 family, member 3 |
| Adaptive | B-cells | AHNAK2 | AHNAK nucleoprotein 2 |
| Adaptive | B-cells | ARHGAP24 | Rho GTPase activating protein 24 |
| Adaptive | B-cells | BACE2 | beta-site APP-cleaving enzyme 2 |
| Adaptive | B-cells | BACH2 | BTB and CNC homology 1, basic leucine zipper transcription factor 2 |
| Adaptive | B-cells | BANK1 | B-cell scaffold protein with ankyrin repeats 1 |
| Adaptive | B-cells | BCL11A | B-cell CLL/lymphoma 11A (zinc finger protein) |
| Adaptive | B-cells | BCL7A | B-cell CLL/lymphoma 7A |
| Adaptive | B-cells | BEND4 | BEN domain containing 4 |
| Adaptive | B-cells | BEND5 | BEN domain containing 5 |
| Adaptive | B-cells | BHLHE41 | basic helix-loop-helix family, member e41 |
| Adaptive | B-cells | BIRC3 | baculoviral IAP repeat containing 3 |
| Adaptive | B-cells | BLK | BLK proto-oncogene, Src family tyrosine kinase |
| Adaptive | B-cells | BLNK | B-cell linker |
| Adaptive | B-cells | BTK | Bruton agammaglobulinemia tyrosine kinase |
| Adaptive | B-cells | BTLA | B and T lymphocyte associated |
| Adaptive | B-cells | BTNL9 | butyrophilin-like 9 |
| Adaptive | B-cells | C12orf42 | chromosome 12 open reading frame 42 |
| Adaptive | B-cells | CBLN3 | cerebellin 3 precursor |
| Adaptive | B-cells | CCDC50 | coiled-coil domain containing 50 |
| Adaptive | B-cells | CCSER1 | coiled-coil serine-rich protein 1 |
| Adaptive | B-cells | CD180 | CD180 molecule |
| Adaptive | B-cells | CD19 | CD19 molecule |

FIG. 9 (Cont.)

| Class | CellType | GeneSymbol | Description |
|---|---|---|---|
| Adaptive | B-cells | CD1C | CD1c molecule |
| Adaptive | B-cells | CD200 | CD200 molecule |
| Adaptive | B-cells | CD22 | CD22 molecule |
| Adaptive | B-cells | CD40 | CD40 molecule, TNF receptor superfamily member 5 |
| Adaptive | B-cells | CD72 | CD72 molecule |
| Adaptive | B-cells | CD79A | CD79a molecule, immunoglobulin-associated alpha |
| Adaptive | B-cells | CD79B | CD79b molecule, immunoglobulin-associated beta |
| Adaptive | B-cells | CD83 | CD83 molecule |
| Adaptive | B-cells | CDCA7L | cell division cycle associated 7-like |
| Adaptive | B-cells | CDK14 | cyclin-dependent kinase 14 |
| Adaptive | B-cells | CELSR1 | cadherin, EGF LAG seven-pass G-type receptor 1 |
| Adaptive | B-cells | CIITA | class II, major histocompatibility complex, transactivator |
| Adaptive | B-cells | CLCN4 | chloride channel, voltage-sensitive 4 |
| Adaptive | B-cells | CLEC17A | C-type lectin domain family 17, member A |
| Adaptive | B-cells | CLIC4 | chloride intracellular channel 4 |
| Adaptive | B-cells | CNR2 | cannabinoid receptor 2 (macrophage) |
| Adaptive | B-cells | CNTNAP2 | contactin associated protein-like 2 |
| Adaptive | B-cells | COBLL1 | cordon-bleu WH2 repeat protein-like 1 |
| Adaptive | B-cells | COCH | cochlin |
| Adaptive | B-cells | COL19A1 | collagen, type XIX, alpha 1 |
| Adaptive | B-cells | COL4A3 | collagen, type IV, alpha 3 (Goodpasture antigen) |
| Adaptive | B-cells | COL4A4 | collagen, type IV, alpha 4 |
| Adaptive | B-cells | CORO2B | coronin, actin binding protein, 2B |
| Adaptive | B-cells | CPNE5 | copine V |
| Adaptive | B-cells | CR2 | complement component (3d/Epstein Barr virus) receptor 2 |
| Adaptive | B-cells | CXCR5 | chemokine (C-X-C motif) receptor 5 |
| Adaptive | B-cells | CXXC5 | CXXC finger protein 5 |
| Adaptive | B-cells | DBNDD1 | dysbindin (dystrobrevin binding protein 1) domain containing 1 |
| Adaptive | B-cells | DENND5B | DENN/MADD domain containing 5B |
| Adaptive | B-cells | DERL3 | derlin 3 |
| Adaptive | B-cells | DIRAS1 | DIRAS family, GTP-binding RAS-like 1 |
| Adaptive | B-cells | DPF3 | D4, zinc and double PHD fingers, family 3 |
| Adaptive | B-cells | DSP | desmoplakin |
| Adaptive | B-cells | DTX1 | deltex 1, E3 ubiquitin ligase |
| Adaptive | B-cells | DTX4 | deltex 4, E3 ubiquitin ligase |
| Adaptive | B-cells | E2F5 | E2F transcription factor 5, p130-binding |
| Adaptive | B-cells | EBF1 | early B-cell factor 1 |
| Adaptive | B-cells | EML6 | echinoderm microtubule associated protein like 6 |
| Adaptive | B-cells | FADS3 | fatty acid desaturase 3 |
| Adaptive | B-cells | FAM111B | family with sequence similarity 111, member B |

FIG. 9 (Cont.)

| Class | CellType | GeneSymbol | Description |
|---|---|---|---|
| Adaptive | B-cells | FAM129C | family with sequence similarity 129, member C |
| Adaptive | B-cells | FAM167A | family with sequence similarity 167, member A |
| Adaptive | B-cells | FAM69B | family with sequence similarity 69, member B |
| Adaptive | B-cells | FCER2 | Fc fragment of IgE, low affinity II, receptor for (CD23) |
| Adaptive | B-cells | FCGR2B | Fc fragment of IgG, low affinity IIb, receptor (CD32) |
| Adaptive | B-cells | FCRL1 | Fc receptor-like 1 |
| Adaptive | B-cells | FCRL2 | Fc receptor-like 2 |
| Adaptive | B-cells;NK | FCRL3 | Fc receptor-like 3 |
| Adaptive | B-cells | FCRL5 | Fc receptor-like 5 |
| Adaptive | B-cells | FCRLA | Fc receptor-like A |
| Adaptive | B-cells | FFAR1 | free fatty acid receptor 1 |
| Adaptive | B-cells | GNG7 | guanine nucleotide binding protein (G protein), gamma 7 |
| Adaptive | B-cells | GYLTL1B | glycosyltransferase-like 1B |
| Adaptive | B-cells | HES1 | hes family bHLH transcription factor 1 |
| Adaptive | B-cells | HIP1R | huntingtin interacting protein 1 related |
| Adaptive | B-cells | HLA-DMA | major histocompatibility complex, class II, DM alpha |
| Adaptive | B-cells | HLA-DMB | major histocompatibility complex, class II, DM beta |
| Adaptive | B-cells | HLA-DOA | major histocompatibility complex, class II, DO alpha |
| Adaptive | B-cells | HLA-DOB | major histocompatibility complex, class II, DO beta |
| Adaptive | B-cells | HLA-DPA1 | major histocompatibility complex, class II, DP alpha 1 |
| Adaptive | B-cells | HLA-DPB1 | major histocompatibility complex, class II, DP beta 1 |
| Adaptive | B-cells | HLA-DQA2 | major histocompatibility complex, class II, DQ alpha 2 |
| Adaptive | B-cells | HLA-DQB2 | major histocompatibility complex, class II, DQ beta 2 |
| Adaptive | B-cells | HLA-DRB5 | major histocompatibility complex, class II, DR beta 5 |
| Adaptive | B-cells | HS3ST1 | heparan sulfate (glucosamine) 3-O-sulfotransferase 1 |
| Adaptive | B-cells | HVCN1 | hydrogen voltage-gated channel 1 |
| Adaptive | B-cells | ICOSLG | inducible T-cell co-stimulator ligand |
| Adaptive | B-cells | IFNLR1 | interferon, lambda receptor 1 |
| Adaptive | B-cells | IGJ | immunoglobulin J polypeptide, linker protein for immunoglobulin alpha and mu polypeptides |
| Adaptive | B-cells | IGLL5 | immunoglobulin lambda-like polypeptide 5 |
| Adaptive | B-cells | IL6 | interleukin 6 |
| Adaptive | B-cells | IRF8 | interferon regulatory factor 8 |
| Adaptive | B-cells | IRS1 | insulin receptor substrate 1 |
| Adaptive | B-cells | JADE3 | jade family PHD finger 3 |
| Adaptive | B-cells | JUP | junction plakoglobin |
| Adaptive | B-cells | KCNG1 | potassium voltage-gated channel, subfamily G, member 1 |
| Adaptive | B-cells | KCNH8 | potassium voltage-gated channel, subfamily H (eag-related), member 8 |
| Adaptive | B-cells | KCNIP2 | Kv channel interacting protein 2 |

FIG. 9 (Cont.)

| Class | CellType | GeneSymbol | Description |
|---|---|---|---|
| Adaptive | B-cells | KCNN4 | potassium intermediate/small conductance calcium-activated channel, subfamily N, member 4 |
| Adaptive | B-cells | KHDRBS2 | KH domain containing, RNA binding, signal transduction associated 2 |
| Adaptive | B-cells | KIAA0226L | KIAA0226-like |
| Adaptive | B-cells | KLF8 | Kruppel-like factor 8 |
| Adaptive | B-cells | KLHL14 | kelch-like family member 14 |
| Adaptive | B-cells | KMO | kynurenine 3-monooxygenase (kynurenine 3-hydroxylase) |
| Adaptive | B-cells | LAMA5 | laminin, alpha 5 |
| Adaptive | B-cells | LAMC1 | laminin, gamma 1 (formerly LAMB2) |
| Adaptive | B-cells | LARGE | like-glycosyltransferase |
| Adaptive | B-cells | LINC00494 | long intergenic non-protein coding RNA 494 |
| Adaptive | B-cells | LINC00926 | long intergenic non-protein coding RNA 926 |
| Adaptive | B-cells | LOC100293211 | uncharacterized LOC100293211 |
| Adaptive | B-cells | LOC100507616 | uncharacterized LOC100507616 |
| Adaptive | B-cells | LOC101927412 | uncharacterized LOC101927412 |
| Adaptive | B-cells | LOC101929133 | uncharacterized LOC101929133 |
| Adaptive | B-cells | LOC101930405 | uncharacterized LOC101930405 |
| Adaptive | B-cells | MACROD2 | MACRO domain containing 2 |
| Adaptive | B-cells | MAP3K9 | mitogen-activated protein kinase kinase kinase 9 |
| Adaptive | B-cells | 1-Mar | membrane-associated ring finger (C3HC4) 1, E3 ubiquitin protein ligase |
| Adaptive | B-cells | MATN1 | matrilin 1, cartilage matrix protein |
| Adaptive | B-cells | MEF2C | myocyte enhancer factor 2C |
| Adaptive | B-cells | MGAT3 | mannosyl (beta-1,4-)-glycoprotein beta-1,4-N-acetylglucosaminyltransferase |
| Adaptive | B-cells | MMP17 | matrix metallopeptidase 17 (membrane-inserted) |
| Adaptive | B-cells | MOB3B | MOB kinase activator 3B |
| Adaptive | B-cells | MS4A1 | membrane-spanning 4-domains, subfamily A, member 1 |
| Adaptive | B-cells | MYO1B | myosin IB |
| Adaptive | B-cells | MYO1E | myosin IE |
| Adaptive | B-cells | MYO7B | myosin VIIB |
| Adaptive | B-cells | MZB1 | marginal zone B and B1 cell-specific protein |
| Adaptive | B-cells | NETO1 | neuropilin (NRP) and tolloid (TLL)-like 1 |
| Adaptive | B-cells | NIPAL4 | NIPA-like domain containing 4 |
| Adaptive | B-cells | NT5E | 5'-nucleotidase, ecto (CD73) |
| Adaptive | B-cells;CD8 | OSBPL10 | oxysterol binding protein-like 10 |
| Adaptive | B-cells | P2RX5 | purinergic receptor P2X, ligand-gated ion channel, 5 |
| Adaptive | B-cells | PARM1 | prostate androgen-regulated mucin-like protein 1 |
| Adaptive | B-cells | PAWR | PRKC, apoptosis, WT1, regulator |
| Adaptive | B-cells | PAX5 | paired box 5 |

FIG.9 (Cont.)

| Class | CellType | GeneSymbol | Description |
|---|---|---|---|
| Adaptive | B-cells | PCDH9 | protocadherin 9 |
| Adaptive | B-cells | PDLIM1 | PDZ and LIM domain 1 |
| Adaptive | B-cells | PEG10 | paternally expressed 10 |
| Adaptive | B-cells | PIK3C2B | phosphatidylinositol-4-phosphate 3-kinase, catalytic subunit type 2 beta |
| Adaptive | B-cells | PKIG | protein kinase (cAMP-dependent, catalytic) inhibitor gamma |
| Adaptive | B-cells | PLD4 | phospholipase D family, member 4 |
| Adaptive | B-cells | PLEKHG1 | pleckstrin homology domain containing, family G (with RhoGef domain) member 1 |
| Adaptive | B-cells | PMEPA1 | prostate transmembrane protein, androgen induced 1 |
| Adaptive | B-cells | PNOC | prepronociceptin |
| Adaptive | B-cells | PNPLA7 | patatin-like phospholipase domain containing 7 |
| Adaptive | B-cells | PPAPDC1B | phosphatidic acid phosphatase type 2 domain containing 1B |
| Adaptive | B-cells | PTPRK | protein tyrosine phosphatase, receptor type, K |
| Adaptive | B-cells | RAB30 | RAB30, member RAS oncogene family |
| Adaptive | B-cells | RALGPS2 | Ral GEF with PH domain and SH3 binding motif 2 |
| Adaptive | B-cells | RASGRP3 | RAS guanyl releasing protein 3 (calcium and DAG-regulated) |
| Adaptive | B-cells;CD4;CD8 | RIC3 | RIC3 acetylcholine receptor chaperone |
| Adaptive | B-cells | SCN3A | sodium channel, voltage-gated, type III, alpha subunit |
| Adaptive | B-cells | SDK2 | sidekick cell adhesion molecule 2 |
| Adaptive | B-cells | SEL1L3 | sel-1 suppressor of lin-12-like 3 (C. elegans) |
| Adaptive | B-cells | SETBP1 | SET binding protein 1 |
| Adaptive | B-cells | SIGLEC6 | sialic acid binding Ig-like lectin 6 |
| Adaptive | B-cells | SLC2A5 | solute carrier family 2 (facilitated glucose/fructose transporter), member 5 |
| Adaptive | B-cells | SLC38A11 | solute carrier family 38, member 11 |
| Adaptive | B-cells | SLC9A7 | solute carrier family 9, subfamily A (NHE7, cation proton antiporter 7), member 7 |
| Adaptive | B-cells | SNX22 | sorting nexin 22 |
| Adaptive | B-cells | STAP1 | signal transducing adaptor family member 1 |
| Adaptive | B-cells | STRBP | spermatid perinuclear RNA binding protein |
| Adaptive | B-cells | SWAP70 | SWAP switching B-cell complex 70kDa subunit |
| Adaptive | B-cells | SYNPO | synaptopodin |
| Adaptive | B-cells | TCF4 | transcription factor 4 |
| Adaptive | B-cells | TCL1A | T-cell leukemia/lymphoma 1A |
| Adaptive | B-cells | TCL6 | T-cell leukemia/lymphoma 6 (non-protein coding) |
| Adaptive | B-cells | TEAD2 | TEA domain family member 2 |
| Adaptive | B-cells;NK | TLE1 | transducin-like enhancer of split 1 (E(sp1) homolog, Drosophila) |
| Adaptive | B-cells | TLR10 | toll-like receptor 10 |

FIG. 9 (Cont.)

| Class | CellType | GeneSymbol | Description |
|---|---|---|---|
| Adaptive | B-cells | TNFRSF13B | tumor necrosis factor receptor superfamily, member 13B |
| Adaptive | B-cells | TNFRSF13C | tumor necrosis factor receptor superfamily, member 13C |
| Adaptive | B-cells | TPD52 | tumor protein D52 |
| Adaptive | B-cells | TRIO | trio Rho guanine nucleotide exchange factor |
| Adaptive | B-cells | TSPAN13 | tetraspanin 13 |
| Adaptive | B-cells | TSPAN33 | tetraspanin 33 |
| Adaptive | B-cells | TSPYL5 | TSPY-like 5 |
| Adaptive | B-cells | USP6NL | USP6 N-terminal like |
| Adaptive | B-cells | VAV2 | vav 2 guanine nucleotide exchange factor |
| Adaptive | B-cells | VPREB3 | pre-B lymphocyte 3 |
| Adaptive | B-cells | WDFY4 | WDFY family member 4 |
| Adaptive | B-cells | ZBTB32 | zinc finger and BTB domain containing 32 |
| Adaptive | B-cells | ZDHHC23 | zinc finger, DHHC-type containing 23 |
| Adaptive | B-cells | ZNF532 | zinc finger protein 532 |
| Adaptive | B-cells | ZNF608 | zinc finger protein 608 |
| Adaptive | B-cells | ZNF711 | zinc finger protein 711 |
| Adaptive | B-cells | ZNF860 | zinc finger protein 860 |
| Adaptive | CD4;CD8 | ABCD2 | ATP-binding cassette, sub-family D (ALD), member 2 |
| Adaptive | CD4;CD8 | ABLIM1 | actin binding LIM protein 1 |
| Adaptive | CD4 | ACE | angiotensin I converting enzyme |
| Adaptive | CD4 | ADAMTSL5 | ADAMTS-like 5 |
| Adaptive | CD4 | ADTRP | androgen-dependent TFPI-regulating protein |
| Adaptive | CD4 | AK5 | adenylate kinase 5 |
| Adaptive | CD4 | ALS2CL | ALS2 C-terminal like |
| Adaptive | CD4;CD8 | AMIGO1 | adhesion molecule with Ig-like domain 1 |
| Adaptive | CD4 | ANK3 | ankyrin 3, node of Ranvier (ankyrin G) |
| Adaptive | CD4 | ANKRD55 | ankyrin repeat domain 55 |
| Adaptive | CD4;CD8 | ANO9 | anoctamin 9 |
| Adaptive | CD4 | AP3M2 | adaptor-related protein complex 3, mu 2 subunit |
| Adaptive | CD4;CD8;NK | APBA2 | amyloid beta (A4) precursor protein-binding, family A, member 2 |
| Adaptive | CD4 | APBB1 | amyloid beta (A4) precursor protein-binding, family B, member 1 (Fe65) |
| Adaptive | CD4;CD8 | AQP3 | aquaporin 3 (Gill blood group) |
| Adaptive | CD4;NK | ATP10A | ATPase, class V, type 10A |
| Adaptive | CD4;CD8 | ATP8B2 | ATPase, aminophospholipid transporter, class I, type 8B, member 2 |
| Adaptive | CD4 | AXIN2 | axin 2 |
| Adaptive | CD4 | BAG3 | BCL2-associated athanogene 3 |
| Adaptive | CD4;CD8 | BCL11B | B-cell CLL/lymphoma 11B (zinc finger protein) |
| Adaptive | CD4 | BCL2 | B-cell CLL/lymphoma 2 |
| Adaptive | CD4 | C14orf132 | chromosome 14 open reading frame 132 |
| Adaptive | CD4;CD8 | C14orf64 | chromosome 14 open reading frame 64 |

FIG. 9 (Cont.)

| Class | CellType | GeneSymbol | Description |
|---|---|---|---|
| Adaptive | CD4;CD8 | CA6 | carbonic anhydrase VI |
| Adaptive | CD4 | CACNA1H | calcium channel, voltage-dependent, T type, alpha 1H subunit |
| Adaptive | CD4;CD8 | CACNA1I | calcium channel, voltage-dependent, T type, alpha 1I subunit |
| Adaptive | CD4;CD8 | CAMK4 | calcium/calmodulin-dependent protein kinase IV |
| Adaptive | CD4;CD8 | CCDC64 | coiled-coil domain containing 64 |
| Adaptive | CD4 | CCR4 | chemokine (C-C motif) receptor 4 |
| Adaptive | CD4;CD8 | CCR7 | chemokine (C-C motif) receptor 7 |
| Adaptive | CD4;CD8 | CD2 | CD2 molecule |
| Adaptive | CD4;CD8;NK | CD226 | CD226 molecule |
| Adaptive | CD4;CD8;NK | CD247 | CD247 molecule |
| Adaptive | CD4;CD8 | CD27 | CD27 molecule |
| Adaptive | CD4;CD8 | CD28 | CD28 molecule |
| Adaptive | CD4;CD8 | CD3D | CD3d molecule, delta (CD3-TCR complex) |
| Adaptive | CD4;CD8 | CD3E | CD3e molecule, epsilon (CD3-TCR complex) |
| Adaptive | CD4;CD8 | CD3G | CD3g molecule, gamma (CD3-TCR complex) |
| Adaptive | CD4 | CD40LG | CD40 ligand |
| Adaptive | CD4;CD8 | CD5 | CD5 molecule |
| Adaptive | CD4;CD8 | CD6 | CD6 molecule |
| Adaptive | CD4 | CD69 | CD69 molecule |
| Adaptive | CD4;CD8 | CD96 | CD96 molecule |
| Adaptive | CD4 | CEP170B | centrosomal protein 170B |
| Adaptive | CD4;CD8 | CHRM3-AS2 | CHRM3 antisense RNA 2 |
| Adaptive | CD4;CD8 | CLUHP3 | clustered mitochondria (cluA/CLU1) homolog pseudogene 3 |
| Adaptive | CD4 | COL5A3 | collagen, type V, alpha 3 |
| Adaptive | CD4;CD8 | COL6A1 | collagen, type VI, alpha 1 |
| Adaptive | CD4 | CRIP2 | cysteine-rich protein 2 |
| Adaptive | CD4 | CTLA4 | cytotoxic T-lymphocyte-associated protein 4 |
| Adaptive | CD4 | DACT1 | dishevelled-binding antagonist of beta-catenin 1 |
| Adaptive | CD4 | DBH-AS1 | DBH antisense RNA 1 |
| Adaptive | CD4;CD8 | DCHS1 | dachsous cadherin-related 1 |
| Adaptive | CD4;CD8;NK | DHRS3 | dehydrogenase/reductase (SDR family) member 3 |
| Adaptive | CD4;CD8 | DOCK9 | dedicator of cytokinesis 9 |
| Adaptive | CD4;CD8 | DPP4 | dipeptidyl-peptidase 4 |
| Adaptive | CD4 | DUSP16 | dual specificity phosphatase 16 |
| Adaptive | CD4;CD8 | DUSP4 | dual specificity phosphatase 4 |
| Adaptive | CD4;CD8 | EDAR | ectodysplasin A receptor |
| Adaptive | CD4;CD8 | ENO2 | enolase 2 (gamma, neuronal) |
| Adaptive | CD4;CD8 | EPHX2 | epoxide hydrolase 2, cytoplasmic |
| Adaptive | CD4 | ETS1 | v-ets avian erythroblastosis virus E26 oncogene homolog 1 |
| Adaptive | CD4 | FAAH2 | fatty acid amide hydrolase 2 |
| Adaptive | CD4;CD8 | FAM102A | family with sequence similarity 102, member A |
| Adaptive | CD4;CD8 | FAM153A | family with sequence similarity 153, member A |

FIG. 9 (Cont.)

| Class | CellType | GeneSymbol | Description |
|---|---|---|---|
| Adaptive | CD4 | FAM184A | family with sequence similarity 184, member A |
| Adaptive | CD4 | FAM84B | family with sequence similarity 84, member B |
| Adaptive | CD4 | FBLN7 | fibulin 7 |
| Adaptive | CD4 | FBXL16 | F-box and leucine-rich repeat protein 16 |
| Adaptive | CD4 | FHIT | fragile histidine triad |
| Adaptive | CD4 | FHL1 | four and a half LIM domains 1 |
| Adaptive | CD4;CD8 | FLJ45825 | uncharacterized LOC100505530 |
| Adaptive | CD4 | FLT3LG | fms-related tyrosine kinase 3 ligand |
| Adaptive | CD4 | FOXP3 | forkhead box P3 |
| Adaptive | CD4;CD8;NK | GATA3 | GATA binding protein 3 |
| Adaptive | CD4;CD8 | GCNT4 | glucosaminyl (N-acetyl) transferase 4, core 2 |
| Adaptive | CD4;CD8 | GOLGA7B | golgin A7 family, member B |
| Adaptive | CD4;CD8 | GOLGA8A | golgin A8 family, member A |
| Adaptive | CD4 | GP5 | glycoprotein V (platelet) |
| Adaptive | CD4 | GPA33 | glycoprotein A33 (transmembrane) |
| Adaptive | CD4;CD8 | GPRASP1 | G protein-coupled receptor associated sorting protein 1 |
| Adaptive | CD4;CD8 | GPRIN3 | GPRIN family member 3 |
| Adaptive | CD4;CD8 | HAPLN3 | hyaluronan and proteoglycan link protein 3 |
| Adaptive | CD4 | HKDC1 | hexokinase domain containing 1 |
| Adaptive | CD4 | HLF | hepatic leukemia factor |
| Adaptive | CD4;CD8 | HPCAL4 | hippocalcin like 4 |
| Adaptive | CD4;CD8 | ICOS | inducible T-cell co-stimulator |
| Adaptive | CD4 | IGSF9B | immunoglobulin superfamily, member 9B |
| Adaptive | CD4 | IL2RA | interleukin 2 receptor, alpha |
| Adaptive | CD4;CD8 | IL32 | interleukin 32 |
| Adaptive | CD4 | IL6ST | interleukin 6 signal transducer |
| Adaptive | CD4;CD8 | IL7R | interleukin 7 receptor |
| Adaptive | CD4;CD8 | INPP4B | inositol polyphosphate-4-phosphatase, type II, 105kDa |
| Adaptive | CD4 | ISM1 | isthmin 1, angiogenesis inhibitor |
| Adaptive | CD4;CD8 | ITGA6 | integrin, alpha 6 |
| Adaptive | CD4;CD8 | ITK | IL2-inducible T-cell kinase |
| Adaptive | CD4;CD8 | ITM2A | integral membrane protein 2A |
| Adaptive | CD4 | KANK1 | KN motif and ankyrin repeat domains 1 |
| Adaptive | CD4;CD8 | KCNA3 | potassium voltage-gated channel, shaker-related subfamily, member 3 |
| Adaptive | CD4 | KIF5C | kinesin family member 5C |
| Adaptive | CD4 | KLF12 | Kruppel-like factor 12 |
| Adaptive | CD4;CD8;NK | KLRB1 | killer cell lectin-like receptor subfamily B, member 1 |
| Adaptive | CD4 | KRT72 | keratin 72 |
| Adaptive | CD4;CD8 | LCK | LCK proto-oncogene, Src family tyrosine kinase |
| Adaptive | CD4 | LDHB | lactate dehydrogenase B |
| Adaptive | CD4 | LDLRAP1 | low density lipoprotein receptor adaptor protein 1 |

FIG. 9 (Cont.)

| Class | CellType | GeneSymbol | Description |
|---|---|---|---|
| Adaptive | CD4;CD8 | LEF1 | lymphoid enhancer-binding factor 1 |
| Adaptive | CD4;CD8 | LINC00649 | long intergenic non-protein coding RNA 649 |
| Adaptive | CD4;CD8;NK | LINC00861 | long intergenic non-protein coding RNA 861 |
| Adaptive | CD4;CD8 | LMTK3 | lemur tyrosine kinase 3 |
| Adaptive | CD4 | LOC100996286 | uncharacterized LOC100996286 |
| Adaptive | CD4 | LOC101928150 | uncharacterized LOC101928150 |
| Adaptive | CD4;CD8 | LOC101930595 | uncharacterized LOC101930595 |
| Adaptive | CD4;CD8 | LRRN3 | leucine rich repeat neuronal 3 |
| Adaptive | CD4 | LTBP3 | latent transforming growth factor beta binding protein 3 |
| Adaptive | CD4 | MAF | v-maf avian musculoaponeurotic fibrosarcoma oncogene homolog |
| Adaptive | CD4;CD8 | MAL | mal, T-cell differentiation protein |
| Adaptive | CD4 | MAN1C1 | mannosidase, alpha, class 1C, member 1 |
| Adaptive | CD4 | MDFIC | MyoD family inhibitor domain containing |
| Adaptive | CD4 | MDS2 | myelodysplastic syndrome 2 translocation associated |
| Adaptive | CD4 | MFHAS1 | malignant fibrous histiocytoma amplified sequence 1 |
| Adaptive | CD4 | MID2 | midline 2 |
| Adaptive | CD4;CD8 | MLLT3 | myeloid/lymphoid or mixed-lineage leukemia (trithorax homolog, Drosophila); translocated to, 3 |
| Adaptive | CD4;CD8 | NELL2 | NEL-like 2 (chicken) |
| Adaptive | CD4;CD8 | NLGN2 | neuroligin 2 |
| Adaptive | CD4;CD8 | NPDC1 | neural proliferation, differentiation and control, 1 |
| Adaptive | CD4;CD8 | NR3C2 | nuclear receptor subfamily 3, group C, member 2 |
| Adaptive | CD4 | OBSCN | obscurin, cytoskeletal calmodulin and titin-interacting RhoGEF |
| Adaptive | CD4;CD8 | OXNAD1 | oxidoreductase NAD-binding domain containing 1 |
| Adaptive | CD4;CD8 | PBX4 | pre-B-cell leukemia homeobox 4 |
| Adaptive | CD4 | PCED1B | PC-esterase domain containing 1B |
| Adaptive | CD4 | PCED1B-AS1 | PCED1B antisense RNA 1 |
| Adaptive | CD4 | PI16 | peptidase inhibitor 16 |
| Adaptive | CD4 | PKIA | protein kinase (cAMP-dependent, catalytic) inhibitor alpha |
| Adaptive | CD4;CD8 | PLCG1 | phospholipase C, gamma 1 |
| Adaptive | CD4 | PLCL1 | phospholipase C-like 1 |
| Adaptive | CD4;CD8 | PLEKHB1 | pleckstrin homology domain containing, family B (evectins) member 1 |
| Adaptive | CD4;CD8 | PLEKHG4 | pleckstrin homology domain containing, family G (with RhoGef domain) member 4 |
| Adaptive | CD4;CD8 | PLEKHG5 | pleckstrin homology domain containing, family G (with RhoGef domain) member 5 |
| Adaptive | CD4;CD8 | PLXDC1 | plexin domain containing 1 |

FIG. 9 (Cont.)

| Class | CellType | GeneSymbol | Description |
|---|---|---|---|
| Adaptive | CD4 | PRKCA | protein kinase C, alpha |
| Adaptive | CD4;CD8 | PRKCQ | protein kinase C, theta |
| Adaptive | CD4;CD8 | PRKCQ-AS1 | PRKCQ antisense RNA 1 |
| Adaptive | CD4;CD8 | RASGRF2 | Ras protein-specific guanine nucleotide-releasing factor 2 |
| Adaptive | CD4;CD8 | RASGRP1 | RAS guanyl releasing protein 1 (calcium and DAG-regulated) |
| Adaptive | CD4;CD8 | RCAN3 | RCAN family member 3 |
| Adaptive | CD4 | RGMB | repulsive guidance molecule family member b |
| Adaptive | CD4;CD8 | RHPN1 | rhophilin, Rho GTPase binding protein 1 |
| Adaptive | CD4 | RLTPR | RGD motif, leucine rich repeats, tropomodulin domain and proline-rich containing |
| Adaptive | CD4;CD8 | RNF157 | ring finger protein 157 |
| Adaptive | CD4;CD8;NK | RORA | RAR-related orphan receptor A |
| Adaptive | CD4 | RORC | RAR-related orphan receptor C |
| Adaptive | CD4 | RTKN2 | rhotekin 2 |
| Adaptive | CD4;CD8 | S1PR1 | sphingosine-1-phosphate receptor 1 |
| Adaptive | CD4 | SARDH | sarcosine dehydrogenase |
| Adaptive | CD4;CD8 | SEC14L2 | SEC14-like 2 (S. cerevisiae) |
| Adaptive | CD4;CD8 | SIRPG | signal-regulatory protein gamma |
| Adaptive | CD4 | SIT1 | signaling threshold regulating transmembrane adaptor 1 |
| Adaptive | CD4 | SKAP1 | src kinase associated phosphoprotein 1 |
| Adaptive | CD4 | SLAMF1 | signaling lymphocytic activation molecule family member 1 |
| Adaptive | CD4 | SLC22A17 | solute carrier family 22, member 17 |
| Adaptive | CD4 | SLC22A23 | solute carrier family 22, member 23 |
| Adaptive | CD4;CD8;NK | SLFN12L | schlafen family member 12-like |
| Adaptive | CD4;CD8 | SNPH | syntaphilin |
| Adaptive | CD4;NK | SOCS2 | suppressor of cytokine signaling 2 |
| Adaptive | CD4;CD8 | SPOCK2 | sparc/osteonectin, cwcv and kazal-like domains proteoglycan (testican) 2 |
| Adaptive | CD4 | ST6GALNAC1 | ST6 (alpha-N-acetyl-neuraminyl-2,3-beta-galactosyl-1,3)-N-acetylgalactosaminide alpha-2,6-sialyltransferase 1 |
| Adaptive | CD4 | ST8SIA1 | ST8 alpha-N-acetyl-neuraminide alpha-2,8-sialyltransferase 1 |
| Adaptive | CD4;CD8;NK | STAT4 | signal transducer and activator of transcription 4 |
| Adaptive | CD4 | STMN3 | stathmin-like 3 |

FIG. 9 (Cont.)

| Class | CellType | GeneSymbol | Description |
|---|---|---|---|
| Adaptive | CD4 | SUSD4 | sushi domain containing 4 |
| Adaptive | CD4;CD8 | TBC1D4 | TBC1 domain family, member 4 |
| Adaptive | CD4;CD8 | TC2N | tandem C2 domains, nuclear |
| Adaptive | CD4 | TCEA3 | transcription elongation factor A (SII), 3 |
| Adaptive | CD4;CD8 | TCF7 | transcription factor 7 (T-cell specific, HMG-box) |
| Adaptive | CD4;CD8 | TESPA1 | thymocyte expressed, positive selection associated 1 |
| Adaptive | CD4 | THEM4 | thioesterase superfamily member 4 |
| Adaptive | CD4;CD8 | THEMIS | thymocyte selection associated |
| Adaptive | CD4 | TIAM1 | T-cell lymphoma invasion and metastasis 1 |
| Adaptive | CD4;CD8 | TIGIT | T cell immunoreceptor with Ig and ITIM domains |
| Adaptive | CD4 | TJP3 | tight junction protein 3 |
| Adaptive | CD4;CD8 | TLE2 | transducin-like enhancer of split 2 |
| Adaptive | CD4 | TMEM204 | transmembrane protein 204 |
| Adaptive | CD4;CD8 | TMEM30B | transmembrane protein 30B |
| Adaptive | CD4;CD8 | TNFRSF25 | tumor necrosis factor receptor superfamily, member 25 |
| Adaptive | CD4 | TNFRSF4 | tumor necrosis factor receptor superfamily, member 4 |
| Adaptive | CD4;CD8 | TRABD2A | TraB domain containing 2A |
| Adaptive | CD4;CD8 | TRAT1 | T cell receptor associated transmembrane adaptor 1 |
| Adaptive | CD4 | TRIB2 | tribbles pseudokinase 2 |
| Adaptive | CD4 | TSHZ2 | teashirt zinc finger homeobox 2 |
| Adaptive | CD4 | TSPAN18 | tetraspanin 18 |
| Adaptive | CD4;CD8;NK | TXK | TXK tyrosine kinase |
| Adaptive | CD4;CD8 | UBASH3A | ubiquitin associated and SH3 domain containing A |
| Adaptive | CD4 | VIPR1 | vasoactive intestinal peptide receptor 1 |
| Adaptive | CD4 | VSIG1 | V-set and immunoglobulin domain containing 1 |
| Adaptive | CD4 | WNT7A | wingless-type MMTV integration site family, member 7A |
| Adaptive | CD4;CD8;NK | ZAP70 | zeta-chain (TCR) associated protein kinase 70kDa |
| Adaptive | CD4 | ZC3H12D | zinc finger CCCH-type containing 12D |
| Adaptive | CD8;NK | ADAMTS10 | ADAM metallopeptidas with thrombospondin type 1 motif, 10 |
| Adaptive | CD8;NK | AGAP1 | ArfGAP with GTPase domain, ankyrin repeat and PH domain 1 |
| Adaptive | CD8 | ANAPC1P1 | anaphase promoting complex subunit 1 pseudogene 1 |
| Adaptive | CD8;NK | ARL4C | ADP-ribosylation factor-like 4C |
| Adaptive | CD8;NK | B3GAT1 | beta-1,3-glucuronyltransferase 1 |
| Adaptive | CD8;NK | C1orf21 | chromosome 1 open reading frame 21 |
| Adaptive | CD8;NK | CARD11 | caspase recruitment domain family, member 11 |
| Adaptive | CD8 | CCDC184 | coiled-coil domain containing 184 |
| Adaptive | CD8;NK | CCL5 | chemokine (C-C motif) ligand 5 |
| Adaptive | CD8 | CD248 | CD248 molecule, endosialin |
| Adaptive | CD8;NK | CD7 | CD7 molecule |
| Adaptive | CD8 | CD8A | CD8a molecule |

FIG. 9 (Cont.)

| Class | CellType | GeneSymbol | Description |
|---|---|---|---|
| Adaptive | CD8;NK | COL6A2 | collagen, type VI, alpha 2 |
| Adaptive | CD8 | CRTAM | cytotoxic and regulatory T cell molecule |
| Adaptive | CD8;NK | CST7 | cystatin F (leukocystatin) |
| Adaptive | CD8;NK | CTSW | cathepsin W |
| Adaptive | CD8 | CXCR3 | chemokine (C-X-C motif) receptor 3 |
| Adaptive | CD8 | DAB2IP | DAB2 interacting protein |
| Adaptive | CD8 | DBN1 | drebrin 1 |
| Adaptive | CD8 | DKK3 | dickkopf WNT signaling pathway inhibitor 3 |
| Adaptive | CD8 | DOCK3 | dedicator of cytokinesis 3 |
| Adaptive | CD8 | DSEL | dermatan sulfate epimerase-like |
| Adaptive | CD8;NK | DTX3 | deltex 3, E3 ubiquitin ligase |
| Adaptive | CD8;NK | EOMES | eomesodermin |
| Adaptive | CD8 | FBXO32 | F-box protein 32 |
| Adaptive | CD8 | FCGBP | Fc fragment of IgG binding protein |
| Adaptive | CD8;NK | FCRL6 | Fc receptor-like 6 |
| Adaptive | CD8;NK | FGFBP2 | fibroblast growth factor binding protein 2 |
| Adaptive | CD8 | FLT4 | fms-related tyrosine kinase 4 |
| Adaptive | CD8 | GNAO1 | guanine nucleotide binding protein (G protein), alpha activating activity polypeptide O |
| Adaptive | CD8;NK | GNLY | granulysin |
| Adaptive | CD8;NK | GPR56 | G protein-coupled receptor 56 |
| Adaptive | CD8 | GRAP2 | GRB2-related adaptor protein 2 |
| Adaptive | CD8;NK | GZMA | granzyme A (granzyme 1, cytotoxic T-lymphocyte- associated serine esterase 3) |
| Adaptive | CD8;NK | GZMB | granzyme B (granzyme 2, cytotoxic T-lymphocyte- associated serine esterase 1) |
| Adaptive | CD8;NK | GZMH | granzyme H (cathepsin G-like 2, protein h-CCPX) |
| Adaptive | CD8 | GZMK | granzyme K (granzyme 3; tryptase II) |
| Adaptive | CD8;NK | GZMM | granzyme M (lymphocyte met-ase 1) |
| Adaptive | CD8;NK | IKZF2 | IKAROS family zinc finger 2 (Helios) |
| Adaptive | CD8;NK | IL2RB | interleukin 2 receptor, beta |
| Adaptive | CD8 | JAKMIP1 | janus kinase and microtubule interacting protein 1 |
| Adaptive | CD8;NK | KIAA1671 | KIAA1671 |
| Adaptive | CD8 | KIF21A | kinesin family member 21A |
| Adaptive | CD8;NK | KLRD1 | killer cell lectin-like receptor subfamily D, member 1 |
| Adaptive | CD8 | KLRG1 | killer cell lectin-like receptor subfamily G, member 1 |
| Adaptive | CD8 | LAG3 | lymphocyte-activation gene 3 |
| Adaptive | CD8;NK | LGR6 | leucine-rich repeat containing G protein-coupled receptor 6 |
| Adaptive | CD8 | LMNA | lamin A/C |
| Adaptive | CD8;NK | LOC101928100 | uncharacterized LOC101928100 |
| Adaptive | CD8 | LSR | lipolysis stimulated lipoprotein receptor |
| Adaptive | CD8 | LTK | leukocyte receptor tyrosine kinase |

FIG. 9 (Cont.)

| Class | CellType | GeneSymbol | Description |
|---|---|---|---|
| Adaptive | CD8;NK | MATK | megakaryocyte-associated tyrosine kinase |
| Adaptive | CD8 | MIAT | myocardial infarction associated transcript (non-protein coding) |
| Adaptive | CD8;NK | MYBL1 | v-myb avian myeloblastosis viral oncogene homolog-like 1 |
| Adaptive | CD8;NK | NKG7 | natural killer cell granule protein 7 |
| Adaptive | CD8;NK | NLRC3 | NLR family, CARD domain containing 3 |
| Adaptive | CD8 | NPAS2 | neuronal PAS domain protein 2 |
| Adaptive | CD8 | NRCAM | neuronal cell adhesion molecule |
| Adaptive | CD8 | NSG1 | neuron specific gene family member 1 |
| Adaptive | CD8 | PASK | PAS domain containing serine/threonine kinase |
| Adaptive | CD8 | PDE4D | phosphodiesterase 4D, cAMP-specific |
| Adaptive | CD8;NK | PDZD4 | PDZ domain containing 4 |
| Adaptive | CD8;NK | PRF1 | perforin 1 (pore forming protein) |
| Adaptive | CD8;NK | PRKCH | protein kinase C, eta |
| Adaptive | CD8;NK | PTCH1 | patched 1 |
| Adaptive | CD8 | PTK7 | protein tyrosine kinase 7 |
| Adaptive | CD8;NK | PYHIN1 | pyrin and HIN domain family, member 1 |
| Adaptive | CD8 | RGCC | regulator of cell cycle |
| Adaptive | CD8 | RGS1 | regulator of G-protein signaling 1 |
| Adaptive | CD8 | RTP5 | receptor (chemosensory) transporter protein 5 (putative) |
| Adaptive | CD8 | S100B | S100 calcium binding protein B |
| Adaptive | CD8;NK | S1PR5 | sphingosine-1-phosphate receptor 5 |
| Adaptive | CD8;NK | SAMD3 | sterile alpha motif domain containing 3 |
| Adaptive | CD8;NK | SBK1 | SH3 domain binding kinase 1 |
| Adaptive | CD8 | SCART1 | scavenger receptor protein family member |
| Adaptive | CD8 | SFRP5 | secreted frizzled-related protein 5 |
| Adaptive | CD8 | SH2D1A | SH2 domain containing 1A |
| Adaptive | CD8;NK | SH2D2A | SH2 domain containing 2A |
| Adaptive | CD8;NK | SLA2 | Src-like-adaptor 2 |
| Adaptive | CD8 | SLC38A1 | solute carrier family 38, member 1 |
| Adaptive | CD8 | SLC4A10 | solute carrier family 4, sodium bicarbonate transporter, member 10 |
| Adaptive | CD8 | SMAD7 | SMAD family member 7 |
| Adaptive | CD8;NK | SYTL2 | synaptotagmin-like 2 |
| Adaptive | CD8;NK | TARP | TCR gamma alternate reading frame protein |
| Adaptive | CD8;NK | TBX21 | T-box 21 |
| Adaptive | CD8;NK | TGFBR3 | transforming growth factor, beta receptor III |
| Adaptive | CD8 | TNFAIP3 | tumor necrosis factor, alpha-induced protein 3 |
| Adaptive | CD8 | TTC16 | tetratricopeptide repeat domain 16 |
| Adaptive | CD8 | TTC24 | tetratricopeptide repeat domain 24 |
| Adaptive | CD8 | WNT10B | wingless-type MMTV integration site family, member 10B |

FIG. 9 (Cont.)

| Class | CellType | GeneSymbol | Description |
|---|---|---|---|
| Adaptive | CD8;NK | ZNF683 | zinc finger protein 683 |
| Adaptive | CD8 | ZNF827 | zinc finger protein 827 |
| Adaptive | CD8 | ZNF831 | zinc finger protein 831 |
| Adaptive | NK | ABCB1 | ATP-binding cassette, sub-family B (MDR/TAP), member 1 |
| Adaptive | NK | ADAMTS1 | ADAM metallopeptidase with thrombospondin type 1 motif, 1 |
| Adaptive | NK | AKAP5 | A kinase (PRKA) anchor protein 5 |
| Adaptive | NK | AKR1C3 | aldo-keto reductase family 1, member C3 |
| Adaptive | NK | ARVCF | armadillo repeat gene deleted in velocardiofacial syndrome |
| Adaptive | NK | AUTS2 | autism susceptibility candidate 2 |
| Adaptive | NK | B3GNT7 | UDP-GlcNAc:betaGal beta-1,3-N-acetylglucosaminyltransferase 7 |
| Adaptive | NK | B4GALT6 | UDP-Gal:betaGlcNAc beta 1,4- galactosyltransferase, polypeptide 6 |
| Adaptive | NK | BAI2 | brain-specific angiogenesis inhibitor 2 |
| Adaptive | NK | BNC2 | basonuclin 2 |
| Adaptive | NK | BOK | BCL2-related ovarian killer |
| Adaptive | NK | BZRAP1 | benzodiazepine receptor (peripheral) associated protein 1 |
| Adaptive | NK | C12orf75 | chromosome 12 open reading frame 75 |
| Adaptive | NK | C9orf172 | chromosome 9 open reading frame 172 |
| Adaptive | NK | CACNA2D2 | calcium channel, voltage-dependent, alpha 2/delta subunit 2 |
| Adaptive | NK | CAPN5 | calpain 5 |
| Adaptive | NK | CCL4 | chemokine (C-C motif) ligand 4 |
| Adaptive | NK | CD160 | CD160 molecule |
| Adaptive | NK | CD244 | CD244 molecule, natural killer cell receptor 2B4 |
| Adaptive | NK | CD38 | CD38 molecule |
| Adaptive | NK | CDHR1 | cadherin-related family member 1 |
| Adaptive | NK | CEP78 | centrosomal protein 78kDa |
| Adaptive | NK | CERCAM | cerebral endothelial cell adhesion molecule |
| Adaptive | NK | CHST2 | carbohydrate (N-acetylglucosamine-6-O) sulfotransferase 2 |
| Adaptive | NK | CLDND2 | claudin domain containing 2 |
| Adaptive | NK | CLIC3 | chloride intracellular channel 3 |
| Adaptive | NK | CMKLR1 | chemokine-like receptor 1 |
| Adaptive | NK | COL13A1 | collagen, type XIII, alpha 1 |
| Adaptive | NK | COLGALT2 | collagen beta(1-O)galactosyltransferase 2 |
| Adaptive | NK | COLQ | collagen-like tail subunit (single strand of homotrimer) of asymmetric acetylcholinesterase |
| Adaptive | NK | CTBP2 | C-terminal binding protein 2 |
| Adaptive | NK | DLG5 | discs, large homolog 5 (Drosophila) |

FIG. 9 (Cont.)

| Class | CellType | GeneSymbol | Description |
|---|---|---|---|
| Adaptive | NK | DTHD1 | death domain containing 1 |
| Adaptive | NK | EBF4 | early B-cell factor 4 |
| Adaptive | NK | ELOVL6 | ELOVL fatty acid elongase 6 |
| Adaptive | NK | ENPP5 | ectonucleotide pyrophosphatase/phosphodiesterase 5 (putative) |
| Adaptive | NK | ERBB2 | v-erb-b2 avian erythroblastic leukemia viral oncogene homolog 2 |
| Adaptive | NK | F2R | coagulation factor II (thrombin) receptor |
| Adaptive | NK | FAM179A | family with sequence similarity 179, member A |
| Adaptive | NK | FASLG | Fas ligand (TNF superfamily, member 6) |
| Adaptive | NK | FAT4 | FAT atypical cadherin 4 |
| Adaptive | NK | FCGR3A | Fc fragment of IgG, low affinity IIIa, receptor (CD16a) |
| Adaptive | NK | FEZ1 | fasciculation and elongation protein zeta 1 (zygin I) |
| Adaptive | NK | FSD1 | fibronectin type III and SPRY domain containing 1 |
| Adaptive | NK | GATA2 | GATA binding protein 2 |
| Adaptive | NK | GCSAML | germinal center-associated, signaling and motility-like |
| Adaptive | NK | GFI1 | growth factor independent 1 transcription repressor |
| Adaptive | NK | GFOD1 | glucose-fructose oxidoreductase domain containing 1 |
| Adaptive | NK | GK5 | glycerol kinase 5 (putative) |
| Adaptive | NK | GPR114 | G protein-coupled receptor 114 |
| Adaptive | NK | GPR153 | G protein-coupled receptor 153 |
| Adaptive | NK | GRIK4 | glutamate receptor, ionotropic, kainate 4 |
| Adaptive | NK | HAVCR2 | hepatitis A virus cellular receptor 2 |
| Adaptive | NK | HDC | histidine decarboxylase |
| Adaptive | NK | HEATR9 | HEAT repeat containing 9 |
| Adaptive | NK | HEG1 | heart development protein with EGF-like domains 1 |
| Adaptive | NK | HOPX | HOP homeobox |
| Adaptive | NK | IFNG | interferon, gamma |
| Adaptive | NK | IGFBP7 | insulin-like growth factor binding protein 7 |
| Adaptive | NK | IL12RB2 | interleukin 12 receptor, beta 2 |
| Adaptive | NK | IL18RAP | interleukin 18 receptor accessory protein |
| Adaptive | NK | JAKMIP2 | janus kinase and microtubule interacting protein 2 |
| Adaptive | NK | KIFC3 | kinesin family member C3 |
| Adaptive | NK | KIR2DL1 | killer cell immunoglobulin-like receptor, two domains, long cytoplasmic tail, 1 |
| Adaptive | NK | KIR2DL3 | killer cell immunoglobulin-like receptor, two domains, long cytoplasmic tail, 3 |
| Adaptive | NK | KIR2DS4 | killer cell immunoglobulin-like receptor, two domains, short cytoplasmic tail, 4 |
| Adaptive | NK | KIR3DL2 | killer cell immunoglobulin-like receptor, three domains, long cytoplasmic tail, 2 |
| Adaptive | NK | KIR3DX1 | killer cell immunoglobulin-like receptor, three domains, X1 |

FIG. 9 (Cont.)

| Class | CellType | GeneSymbol | Description |
|---|---|---|---|
| Adaptive | NK | KLRC1 | killer cell lectin-like receptor subfamily C, member 1 |
| Adaptive | NK | KLRC2 | killer cell lectin-like receptor subfamily C, member 2 |
| Adaptive | NK | KLRF1 | killer cell lectin-like receptor subfamily F, member 1 |
| Adaptive | NK | LCNL1 | lipocalin-like 1 |
| Adaptive | NK | LDB2 | LIM domain binding 2 |
| Adaptive | NK | LGALS9B | lectin, galactoside-binding, soluble, 9B |
| Adaptive | NK | LIM2 | lens intrinsic membrane protein 2, 19kDa |
| Adaptive | NK | LINC00299 | long intergenic non-protein coding RNA 299 |
| Adaptive | NK | LINGO2 | leucine rich repeat and Ig domain containing 2 |
| Adaptive | NK | LLGL2 | lethal giant larvae homolog 2 (Drosophila) |
| Adaptive | NK | LPAL2 | lipoprotein, Lp(a)-like 2, pseudogene |
| Adaptive | NK | LRRC16B | leucine rich repeat containing 16B |
| Adaptive | NK | LRRC43 | leucine rich repeat containing 43 |
| Adaptive | NK | MAFF | v-maf avian musculoaponeurotic fibrosarcoma oncogene homolog F |
| Adaptive | NK | MLC1 | megalencephalic leukoencephalopathy with subcortical cysts 1 |
| Adaptive | NK | MMP23B | matrix metallopeptidase 23B |
| Adaptive | NK | MYOM2 | myomesin 2 |
| Adaptive | NK | MYRF | myelin regulatory factor |
| Adaptive | NK | NCALD | neurocalcin delta |
| Adaptive | NK | NCAM1 | neural cell adhesion molecule 1 |
| Adaptive | NK | NCR1 | natural cytotoxicity triggering receptor 1 |
| Adaptive | NK | NCR3 | natural cytotoxicity triggering receptor 3 |
| Adaptive | NK | NFATC2 | nuclear factor of activated T-cells, cytoplasmic, calcineurin-dependent 2 |
| Adaptive | NK | NMUR1 | neuromedin U receptor 1 |
| Adaptive | NK | OSBPL5 | oxysterol binding protein-like 5 |
| Adaptive | NK | PCDH1 | protocadherin 1 |
| Adaptive | NK | PDGFD | platelet derived growth factor D |
| Adaptive | NK | PDGFRB | platelet-derived growth factor receptor, beta polypeptide |
| Adaptive | NK | PHLDB2 | pleckstrin homology-like domain, family B, member 2 |
| Adaptive | NK | PLCH2 | phospholipase C, eta 2 |
| Adaptive | NK | PLEKHF1 | pleckstrin homology domain containing, family F (with FYVE domain) member 1 |
| Adaptive | NK | PODN | podocan |
| Adaptive | NK | PPM1L | protein phosphatase, Mg2+/Mn2+ dependent, 1L |
| Adaptive | NK | PPP2R2B | protein phosphatase 2, regulatory subunit B, beta |
| Adaptive | NK | PRR5L | proline rich 5 like |
| Adaptive | NK | PRSS23 | protease, serine, 23 |

FIG. 9 (Cont.)

| Class | CellType | GeneSymbol | Description |
|---|---|---|---|
| Adaptive | NK | PRSS30P | protease, serine, 30, pseudogene |
| Adaptive | NK | PRSS57 | protease, serine, 57 |
| Adaptive | NK | PTGDR | prostaglandin D2 receptor (DP) |
| Adaptive | NK | PTGDS | prostaglandin D2 synthase 21kDa (brain) |
| Adaptive | NK | PTGER3 | prostaglandin E receptor 3 (subtype EP3) |
| Adaptive | NK | RAB27B | RAB27B, member RAS oncogene family |
| Adaptive | NK | RGS9 | regulator of G-protein signaling 9 |
| Adaptive | NK | RHOBTB3 | Rho-related BTB domain containing 3 |
| Adaptive | NK | RNF165 | ring finger protein 165 |
| Adaptive | NK | RTKN | rhotekin |
| Adaptive | NK | SGSM1 | small G protein signaling modulator 1 |
| Adaptive | NK | SH2D1B | SH2 domain containing 1B |
| Adaptive | NK | SIGLEC17P | sialic acid binding Ig-like lectin 17, pseudogene |
| Adaptive | NK | SLAMF7 | SLAM family member 7 |
| Adaptive | NK | SLC1A7 | solute carrier family 1 (glutamate transporter), member 7 |
| Adaptive | NK | SLC4A4 | solute carrier family 4 (sodium bicarbonate cotransporter), member 4 |
| Adaptive | NK | SLCO4C1 | solute carrier organic anion transporter family, member 4C1 |
| Adaptive | NK | SLFN13 | schlafen family member 13 |
| Adaptive | NK | SOX13 | SRY (sex determining region Y)-box 13 |
| Adaptive | NK | ST8SIA6 | ST8 alpha-N-acetyl-neuraminide alpha-2,8-sialyltransferase 6 |
| Adaptive | NK | TIE1 | tyrosine kinase with immunoglobulin-like and EGF-like domains 1 |
| Adaptive | NK | TKTL1 | transketolase-like 1 |
| Adaptive | NK | TMIGD2 | transmembrane and immunoglobulin domain containing 2 |
| Adaptive | NK | TNFRSF18 | tumor necrosis factor receptor superfamily, member 18 |
| Adaptive | NK | TOX | thymocyte selection-associated high mobility group box |
| Adaptive | NK | TRPV3 | transient receptor potential cation channel, subfamily V, member 3 |
| Adaptive | NK | TSEN54 | TSEN54 tRNA splicing endonuclease subunit |
| Adaptive | NK | TTC38 | tetratricopeptide repeat domain 38 |
| Adaptive | NK | XCL2 | chemokine (C motif) ligand 2 |
| Adaptive | NK | YES1 | YES proto-oncogene 1, Src family tyrosine kinase |
| Adaptive | NK | YPEL1 | yippee-like 1 (Drosophila) |
| Adaptive | NK | ZBTB16 | zinc finger and BTB domain containing 16 |
| Adaptive | NK | ZFYVE28 | zinc finger, FYVE domain containing 28 |

FIG. 9 (Cont.)

METHODS FOR PREDICTING RESPONSE TO TREATMENT

CLAIM OF PRIORITY

This application is a continuation of U.S. application Ser. No. 16/648,955, filed Mar. 19, 2020, which is a national stage of PCT Application No. PCT/2018/051606, filed Sep. 18, 2018, which claims priority to U.S. Provisional Application No. 62/560,628, filed Sep. 19, 2017, each of which are hereby incorporated by reference in their entireties.

TECHNICAL FIELD

Described herein are methods for treating rheumatoid arthritis by determining whether a subject having rheumatoid arthritis will respond to an anti-TNF-alpha therapy based on the number of innate and adaptive immune cells in a sample from the subject.

BACKGROUND

Most patients initiating biologic therapy for rheumatoid arthritis are put on anti-TNF-alpha treatment as the first line treatment. However, approximately 30% of patients do not respond to anti-TNF-alpha treatment, and their disease often progresses before their non-response can be clinically determined. Although studies have been focused on understanding the biology underlying non-response in these patients, this remains an area of active investigation. As a result, new methods are needed for determining ahead of time whether a particular rheumatoid arthritis patient will respond to anti-TNF-alpha therapy, so that an effective drug that the patient is likely to respond to can be administered. This will help drive better treatment outcomes and reduce the burden on the healthcare system.

SUMMARY

The methods described herein enable the prediction of whether a subject having rheumatoid arthritis (RA) will respond to treatment using an anti-TNF-alpha therapy, e.g., treatment with an anti-TNF-alpha therapeutic biologic. The methods are based on observations made in comprehensive molecular profiling studies that identified differences in the innate and adaptive immune cell signatures of rheumatoid arthritis patients at a baseline time point prior to treatment with an anti-TNF-alpha therapy. These differences in immune cell signature profiles indicate that there are differences in the immune systems of patients that may influence whether the patients will respond to anti-TNF-alpha treatment within the first 3 months following therapy. In particular, the relative numbers of innate immune cells (e.g., neutrophils and monocytes) to adaptive immune cells (e.g., B cells and T cells) can be used predict whether a subject with rheumatoid arthritis is likely to respond to an anti-TNF-alpha therapy, and consequently aid in the development, of an effective treatment plan for the subject, i.e., whether to administer an anti-TNF-alpha therapy based on whether the subject is likely to respond well. In some cases, the relative levels of innate immune cell signatures and/or adaptive immune cell signatures can be used to predict whether a subject with rheumatoid arthritis is likely to respond to an anti-TNF-alpha therapy. Thus, the methods described herein provide an improved approach for selecting rheumatoid arthritis patients for anti-TNF-alpha therapy or an alternative treatment other than an anti-TNF-alpha therapy (i.e., not an anti-TNF therapy), resulting in improved treatment outcomes for rheumatoid arthritis patients.

Described herein is a method for treating a patient with rheumatoid arthritis, comprising: determining whether the patient has a high ratio of innate immune cells to adaptive immune cells by: obtaining or having obtained a biological sample from the patient; and performing or having performed an assay on the biological sample to determine if the patient has a high ratio of innate immune cells to adaptive immune cells; and if the patient has a high ratio of innate immune cells to adaptive immune cells, then administering to the patient an anti-TNF therapeutic, and if the patient has a low ratio of innate immune cells to adaptive immune cells, then administering an rheumatoid arthritis treatment other than an anti-TNF therapeutic, thereby treating the patient.

Also described is a method for treating a patient with rheumatoid arthritis, comprising: detecting a ratio of innate immune cells to adaptive immune cells in a biological sample from a patient suffering from rheumatoid arthritis; and if the biological sample has a high ratio of innate immune cells to adaptive immune cells, then administering to the patient an anti-TNF therapeutic; and if the biological sample has a low ratio of innate immune cells to adaptive immune cells, then administering to the patient a rheumatoid arthritis treatment other than an anti-TNF therapeutic, thereby treating the patient.

Also described is a method of advising a treatment for rheumatoid arthritis, comprising: measuring a ratio of innate immune cells to adaptive immune cells in a biological sample from a patient suffering from rheumatoid arthritis; and advising a treatment comprising administration of an anti-TNF therapeutic if the ratio of innate immune cells to adaptive immune cells in the biological sample is high; and advising a treatment comprising administration of a rheumatoid arthritis treatment other than anti-TNF therapeutic if the ratio of innate immune cells to adaptive immune cells in the biological sample is low.

Also described is a method of advising a treatment of rheumatoid arthritis, comprising: selecting two or more patients suffering from rheumatoid arthritis who have not previously been treated with an anti-TNF therapeutic; measuring a ratio of innate immune cells to adaptive immune cells in biological samples collected from the two or more patients suffering from rheumatoid arthritis; advising a treatment of rheumatoid arthritis comprising administration of an anti-MT therapeutic if the ratio of innate immune cells to adaptive immune cells in the biological sample is high; and advising a treatment of rheumatoid arthritis comprising administration of a rheumatoid arthritis treatment other than anti-TNF therapeutic if the ratio of innate immune cells to adaptive immune cells in the biological sample is low; wherein at least one of the two or more patients suffering from rheumatoid arthritis has a ratio of innate immune cells to adaptive immune cells that is low.

Also described A method of identifying a population of subjects with rheumatoid arthritis for treatment with an anti-TNF, comprising: selecting a population of subjects with rheumatoid arthritis who have not previously been treated with an anti-TNF; and identifying a subset of the population having a high ratio of innate immune cells to adaptive immune cells for treatment with an anti-TNF.

In various cases of all of the methods: a high ratio is a ratio above that found in rheumatoid arthritis patients in the lowest 25% of innate immune cell to adaptive immune cell ratios; a high ratio is a ratio above that found in rheumatoid arthritis patients in the lowest 20% of innate immune cell to adaptive immune cell ratios; a high ratio is a ratio above that found in rheumatoid arthritis patients in the lowest 15% of innate immune cell to adaptive immune cell ratios; a high ratio is a ratio above that found in rheumatoid arthritis patients in the lowest 10% of innate immune cell to adaptive immune cell ratios.

Also described is a method of treating patient suffering from rheumatoid arthritis, comprising: administering an anti-TNF therapeutic to a patient having a high ratio of innate immune cells to adaptive immune cells in a biological sample collected from the patient, thereby treating the patient.

Also described is a method of treating a patient suffering from rheumatoid arthritis, comprising: administering a therapeutic other than an anti-TNF therapeutic to a patient having a low ratio of innate immune cells to adaptive immune cells in a biological sample collected from the patient, thereby treating the patient.

S Also described is a method for selecting a therapeutic for the treatment of rheumatoid arthritis in a subject, comprising: determining a ratio of innate immune cells to adaptive immune cells in a sample from a subject and if the proportion of innate immune cells is higher than the proportion of adaptive immune cells then selecting an anti-TNF therapeutic for the treatment of rheumatoid arthritis in the subject; or if the proportion of innate immune cells is lower than the proportion of adaptive immune cells then selecting an non-anti-TNF therapeutic for the treatment of rheumatoid arthritis in the subject; and memorializing the selection.

Also described is a method comprising selecting a therapeutic from the group consisting of an anti-TNF therapeutic and a non-anti-TNF therapeutic for the treatment of rheumatoid arthritis in a subject by determining a ratio of innate immune cells to adaptive immune cells in a sample from a subject, wherein if the proportion of innate immune cells is higher than the proportion of adaptive immune cells then selecting the anti-TNF therapeutic and if the proportion of innate immune cells is lower than the proportion of adaptive immune cells then selecting the non-anti-TNF therapeutic Also described is a method of treating rheumatoid arthritis in a subject comprising: determining that a ratio of innate immune cells to adaptive immune cells in a sample from a subject is high; and administering an anti-TNF therapeutic.

Also described is a method of treating rheumatoid arthritis in a subject comprising: determining that a ratio of innate immune cells to adaptive immune cells in a sample from a subject is low; and administering a non-anti-TNF therapeutic to the subject.

In various embodiments of all of the methods: a low ratio is a ratio below that found in rheumatoid arthritis patients in the highest 75% of innate immune cell to adaptive immune cell ratios; a low ratio is a ratio above that found in rheumatoid arthritis patients in the highest 80% of innate immune cell to adaptive immune cell ratios; a low ratio is a ratio above that found in rheumatoid arthritis patients in the highest 85% of innate immune cell to adaptive immune cell ratios and a low ratio is a ratio above t found in rheumatoid arthritis patients in the highest 90% of innate immune cell to adaptive immune cell ratios.

In various embodiment of all of the methods: the step of determining whether the patient has a high ratio of innate immune cells to adaptive immune cells comprises determining one or more of: the ratio of neutrophils to white blood cells in the biological sample, the ratio of lymphocytes to white blood cells in the biological sample, and the ratio of neutrophils to lymphocytes in the biological sample; the anti-TNF therapeutic is an anti-TNF antibody; the anti-TNF therapeutic is selected from: infliximab, adalimumab, golimumab, certolizumab pegol and etanercept; the rheumatoid arthritis treatment other than an anti-TNF therapeutic is selected from the group consisting of: an anti-CD20 antibody, and anti-IL-6R antibody and a CLTA-4-Ig fusion protein; the rheumatoid arthritis treatment other than an anti-TNF therapeutic is selected from the group consisting of: abatacept, rituximab and tocilizumab; the step of determining whether the patient has a high ratio of innate immune cells to adaptive immune cells comprises determining the expression in the biological sample of one or more of: CD14, CD36, CD46, CD47, CD163, CD164, CD52, CD48, CD3D, CD8A, CD79D, and CD22; the patient is also administered methotrexate; the patient is administered the anti-TNF therapeutic and is not administered methotrexate; the innate immune cells comprise neutrophils and monocytes and the adaptive immune cells comprise B cells and T cells; the step of determining one or more of: the ratio of neutrophils to white blood cells in the biological sample, the ratio of lymphocytes to white blood cells in the biological sample, and the ratio of neutrophils to lymphocytes in the biological sample comprises performing a blood cell count; the step of determining the expression in the biological sample of one or more of: CD14, CD36, CD46, CD47, CD163, CD164, CD52, CD48, CD3D, CD8A, CD79D, and CD22 comprises FACS analysis; step of determining the expression in the biological sample of one or more of: CD14, CD36, CD46, CD47, CD163, CD164, CD52, CD48, CD3D, CD8A, CD79D, and CD22; the step of determining whether the patient has a high ratio of innate immune cells to adaptive immune cells comprises determining the expression in the biological sample of two or more of: CD14, CD36, CD46, CD47, CD163, CD164, CD52, CD48, CD3D, CD8A, CD79D, and CD22.

In various embodiment of all of the methods: the step of determining whether the patient has a high ratio of innate immune cells to adaptive immune cells comprises determining the expression in the biological sample of three or more of: CD14, CD36, CD46, CD47, CD163, CD164, CD52, CD48, CD3D, CD8A, CD79D, and CD22; the step of determining whether the patient has a high ratio of innate immune cells to adaptive immune cells comprises determining the expression in the biological sample of four or more of: CD14, CD36; CD46, CD47, CD163, CD164, CD52, ratio of innate immune cells to adaptive immune cells comprises determining the log of the ratio of neutrophils to lymphocytes (Ln(NRL)) in the biological sample, and administering an anti-TNF therapeutic if the value of Ln(NLR) is greater than about 0.5, 0.6, 0.7, 0.8, 0.9, 1.0, 1.1, 1.2, 1.3, 1.4, 1.5, 1.6; or 1.7.

In various embodiment of all of the methods: the step of determining whether the patient has a high ratio of innate immune cells to adaptive immune cells comprises determining the expression in the biological sample of one (e.g., 2, 3, 4, 5; 6, 7, 8, 9 or 10 or more of the genes in any of FIGS. 6, 7 and 8 associated with an innate immune response and determining the expression in the biological sample of one or more of the genes in FIGS. 6; 7 and 8 associated with an adaptive immune response.

Also described is a method for treating a patient with rheumatoid arthritis, comprising: determining whether the patient has a high ratio of innate immune cells to adaptive immune cells by: obtaining or having obtained a biological sample from the patient; and performing or having performed an assay on the biological sample to determine if the patient has a high ratio of innate immune cells to adaptive immune cells; and if the patient has a high ratio of innate immune cells to adaptive immune cells, then administering to the patient an anti-innate immune cell therapeutic agent, and if the patient has a low ratio of innate immune cells to adaptive immune cells, then administering an rheumatoid arthritis treatment other than an anti-innate immune cell therapeutic agent, thereby treating the patient.

Also described is a method treating a patient with rheumatoid arthritis, comprising: detecting a ratio of innate immune cells to adaptive immune cells in a biological sample from a patient suffering from rheumatoid arthritis; and if the biological sample has a high ratio of innate immune cells to adaptive immune cells, then administering to the patient an anti-innate immune cell therapeutic agent; and if the biological sample has a low ratio of innate immune cells to adaptive immune cells, then administering to the patient a rheumatoid arthritis treatment other than an anti-innate immune cell therapeutic agent, thereby treating the patient.

Also described is a method advising a treatment for rheumatoid arthritis, comprising: measuring a ratio of innate immune cells to adaptive immune cells in a biological sample from a patient suffering from rheumatoid arthritis; and advising a treatment comprising administration of an anti-innate immune cell therapeutic agent if the ratio of innate immune cells to adaptive immune cells in the biological sample is high; and advising a treatment comprising administration of a rheumatoid arthritis treatment other than anti-innate immune cell therapeutic agent if the ratio of innate immune cells to adaptive immune cells in the biological sample is low.

Also described is a method advising a treatment of rheumatoid arthritis, comprising: selecting two or more patients suffering from rheumatoid arthritis who have not previously been treated with an anti-TNF therapeutic; measuring a ratio of innate immune cells to adaptive immune cells in biological samples collected from the two or ✓iron; patients suffering from rheumatoid arthritis; advising a treatment of rheumatoid arthritis comprising administration of an anti-innate immune cell therapeutic agent if the ratio of innate immune cells to adaptive immune cells in the biological sample is high; and advising a treatment of rheumatoid arthritis comprising administration of a rheumatoid arthritis treatment other than anti-innate immune cell therapeutic agent if the ratio of innate immune cells to adaptive immune cells in the biological sample is low; wherein at least one of the two or more patients suffering from rheumatoid arthritis has a ratio of innate immune cells to adaptive immune cells that is low.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1E is a bar graph showing changes in protein expression after 3 months of anti-TNF treatment (MO3) relative to baseline (BL) for Cohort 1 (C1) and Cohort 2 (C2), plotted according to statistical significance (distribution of p-values).

FIG. 1F is a graph showing changes in protein expression in plasma after 3 months of anti-TNF treatment (MO3) relative to baseline (BL), with acute phase proteins highlighted, plotted for Cohort 1 (C1) versus Cohort 2 (C2).

FIG. 4B is a graph showing the average baseline expression of subsets of genes (subsets of the top 10 genes, top 50 genes, or top 250 genes) that are predominantly expressed in particular cell types (neutrophils, CD4 cells, CD8 cells, monocytes, and NK cells) in good responders compared to poor responders in five rheumatoid arthritis datasets (GSE12051, GSE33377, GSE42296, GSE58795, and GSE15258).

Figure 5:
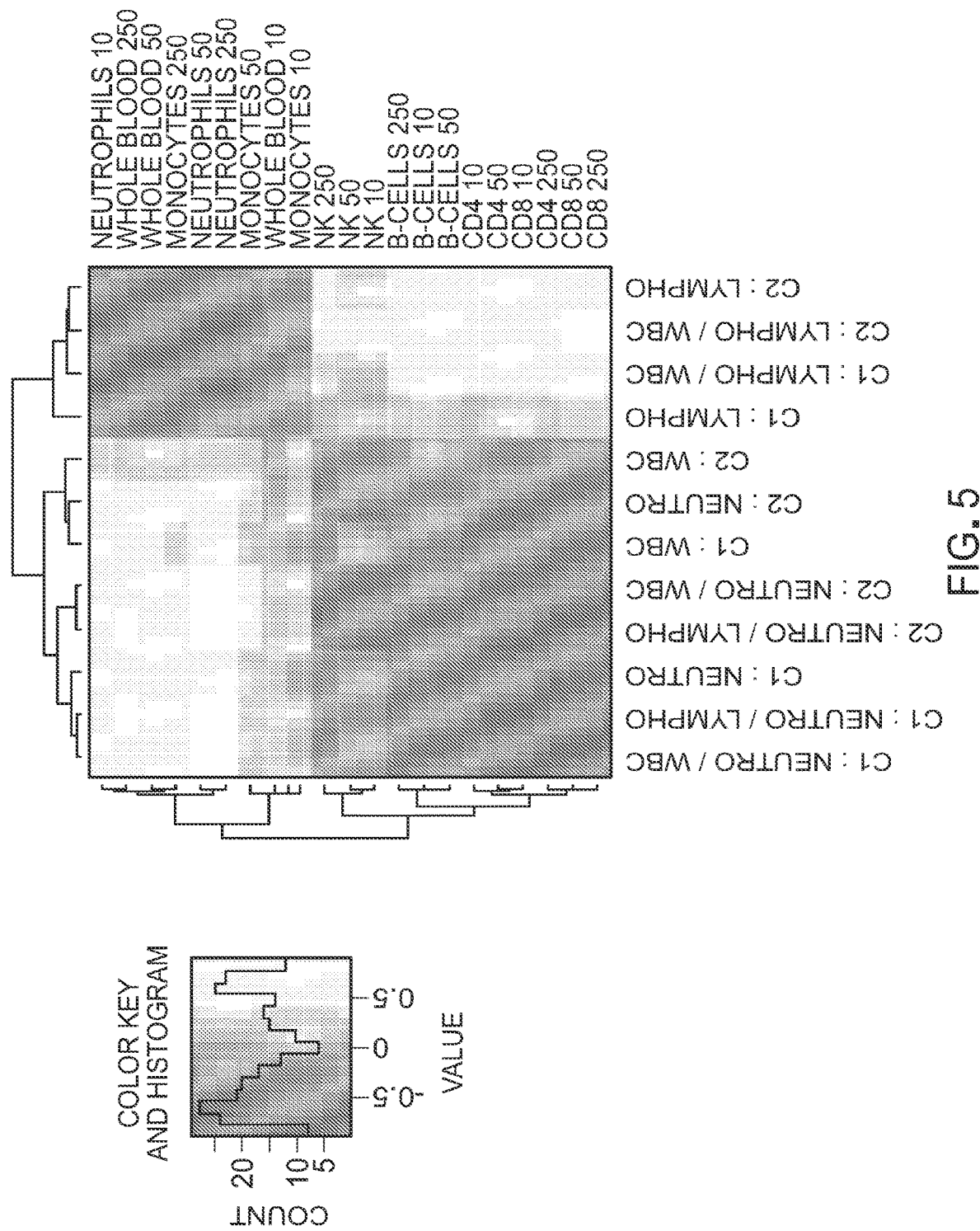

FIG. 5 is a graph showing the correlation between average baseline expression profiles of subsets of genes that are predominantly expressed in particular cell types (neutrophils. B-cells, CD4 cells, CD8 cells, monocytes, and NK cells) in Cohort 1 (C1) and Cohort 2 (C2), compared to corresponding cell counts and their ratios.

FIG. 6 is a list of genes that can be used as markers of innate immune cells (higher expression in neutrophils and monocytes versus T cells and B cells) and genes that can be used as markers of adaptive immune cells (higher expression in T cells and B cells versus neutrophils and monocytes).

FIG. 7 is a list of top 10 genes associated with innate immune response cells (10 from neutrophils and 10 from monocytes) and top 10 genes associated with adaptive immune response cells (10 from B cells, 10 from CD4 cells, 10 from CD8+ cells and 10 from NK cells).

FIG. 8 is a list of top 50 genes associated with innate immune response cells (50 from neutrophils and 50 from monocytes) and top 50 genes associated with adaptive immune response cells (50 from B cells, 50 from CD41 cells, 50 from CD8+ cells and 50 from NK cells).

FIG. 9 is a list of top 200 genes associated with innate immune response cells (50 from neutrophils and 200 from monocytes) and top 20 genes associated with adaptive immune response cells (200 from B cells, 200 from CD4-+ ±cells, 200 from CD8+ cells and 200 from NK cells).

DETAILED DESCRIPTION

Although anti-TNF therapies have provided significant benefits to rheumatoid arthritis (RA) patients, an absence of response in 30% of patients to anti-TNF therapy and an inability to prospectively identify those RA patients that fail to respond to treatment (i.e., non-responders or poor responders) prior to administering an anti-TNF therapy, represents a key unmet medical need. The methods disclosed herein can be used to determine whether a subject with rheumatoid arthritis is likely to respond to treatment with an anti-TNF-alpha therapy. In some embodiments, this determination is used to select a rheumatoid arthritis subject for treatment with an anti-TNF-alpha therapy, e.g., an anti-TNF-alpha therapeutic biologic (e.g., adalimumab, golimumab, certolizumab pegol and/or etanercept). In some embodiments, this determination is used to select a rheumatoid arthritis subject for treatment with an innate immune cell targeting agent (e.g., an anti-TNF-alpha therapeutic biologic), In some embodiments, this determination is used to select a rheumatoid arthritis subject for treatment with a therapy that is not an anti-TNF-alpha therapeutic agent (i.e., is other than an anti-TNF-alpha therapeutic, e.g., a second-line biologic with efficacy in RA patients who fail to respond to anti-TNF therapy, such as biologics that target B and/or T cell responses (e.g., eta rituximab (anti-CD20), abatacept (CTLA-4-Ig), or tocilizumab (anti-IL-6R)). In some embodiments, this determination is used to select a rheumatoid arthritis subject for treatment with a therapy that is any adaptive immune cell targeting agent (e.g., not an anti-TNF-alpha therapeutic biologic).

The methods disclosed herein are based in part on the observation that innate immune cells are present in larger numbers (in comparison to adaptive immune cells) and/or their molecular signatures are present at higher levels in samples collected from rheumatoid arthritis patients who are more likely to respond to treatment with anti-TNF-alpha therapy prior to the administration of the anti-TNF-alpha therapy. By contrast, adaptive immune cells are present in larger numbers (in comparison to innate immune cells) and/or their molecular signatures are present at higher levels in samples collected from rheumatoid arthritis patients who are less likely to respond to treatment with anti-TNF-alpha therapy prior to the administration of the anti-TNF-alpha therapy. The relative numbers and/or signature levels of innate immune cells versus adaptive immune cells in a sample collected from a subject with rheumatoid arthritis can be used to determine whether the subject is likely to respond to an anti-TNF-alpha therapy before a therapy for the disease is selected and administered to the subject.

In some implementations, the disclosure relates to methods for treating a subject with rheumatoid arthritis (e.g., a patient suffering from RA) with an anti-TNF therapeutic that includes determining the ratio of innate immune cells to adaptive immune cells in a sample from the subject, and then determining what treatment to administer based on ratio value. In some embodiments, the ratio is innate immune cells to adaptive immune cells ratio. In some embodiments, the ratio is neutrophils to lymphocytes ratio (NLR). In some embodiments, the ratio is neutrophils to white blood cells ratio (NWR). In some embodiments, the ratio is lymphocytes to white blood cells ratio (LWR). In some embodiments, if the ratio of innate immune cells to adaptive immune cells in a sample from the subject is high, then an anti-TNF; therapeutic is administered to the subject. In some embodiments, if the ratio of innate immune cells to adaptive immune cells in a sample from the subject is not high, then an rheumatoid arthritis treatment other than an anti-TNF therapeutic is administered to the subject.

In some cases, the innate immune cells are neutrophils and monocytes, such that the number of neutrophils and/or monocytes is determined in an RA patient sample prior to selection of an RA therapy. In some cases, the adaptive immune cells are B cells, T cells (e.g., CD4 cells, CD8 cells), such that the number of B cells and/or T cells is determined in an RA patient prior to selection of an RA therapy. In some embodiments, a ratio of any one or more innate immune cell type (e.g., neutrophils and/or monocytes) to any one or more adaptive cell type (e.g., B cells or cells) is determined in an RA patient sample to predict responsiveness to anti-TNF therapy. In some embodiments, if the ratio of neutrophils and/or monocytes to B cells and/or T cells is above a pre-defined threshold (e.g., is high relative to a reference ratio), then one can consider treating the RA patient with an anti-TNF therapeutic or an innate immune cell targeting agent. In some embodiments, the ratio of neutrophils to lymphocytes (NLR) can be determined. If the NLR is above a pre-defined threshold (e.g., is high relative to a reference ratio), then one can consider treating the RA patient with an anti-TNF therapeutic or an innate immune cell targeting agent.

In some embodiments, the ratio of neutrophils to white blood cells (NWR) can be determined. If the NWR is above a pre-defined threshold, then one can consider treating the PA patient with an anti-TNF therapeutic or an innate immune cell targeting agent. In some embodiments, the ratio of lymphocytes to white blood cells (LWR) can be determined. If the LWR is above a pre-defined threshold, then one can consider treating the RA patient with a therapeutic other than an anti-TNF therapeutic or an adaptive immune cell targeting agent. In some embodiments, "white blood cells"

can include a mixture of innate and adaptive immune cells. In some embodiments, white blood cells can include any two or more of neutrophils, lymphocytes, monocytes, eosinophils, and/or basophils. In some embodiments, white blood cells can include neutrophils, lymphocytes, monocytes, eosinophils, and/or basophils. In some embodiments, over 20% of the cells in white blood cells can be neutrophils and lymphocytes, e.g., 20%, 30%, 40%, 50%, 60%, 70%, 80%, 90%, or 95% or more of the cells are neutrophils and lymphocytes.

In some embodiments, determining the ratio of innate immune cells to adaptive immune cells in a sample from the subject with RA can include determining the ratio of neutrophils to white blood cells in the biological sample, the ratio of lymphocytes (B cells and/or T cells) to white blood cells in the biological sample, and/or the ratio of neutrophils to lymphocytes in the biological sample. In some embodiments, determining the ratio of innate immune cells to adaptive immune cells in a sample from the subject with RA includes determining the ratio of neutrophils to white blood cells in the biological sample, the ratio of lymphocytes (B cells and/or T cells) to white blood cells in the biological sample, or the ratio of neutrophils to lymphocytes in the biological sample.

In some embodiments, determining the ratio of innate immune cells to adaptive immune cells in a sample from the subject with RA includes one or more of determining the ratio of neutrophils to white blood cells in the biological sample, the ratio of lymphocytes (B cells and/or cells) to white blood cells in the biological sample, and/or the ratio of neutrophils to lymphocytes in the biological sample.

In some embodiments, the ratio of innate immune cells to adaptive immune cells is determined in a sample from the subject with RA before an anti-TNF therapeutic is administered to the subject. In some embodiments, the ratio of innate immune cells to adaptive immune cells is determined in a sample from the subject with RA shortly before or at the same time that an anti-TNF therapeutic is administered to the subject. In some embodiments, the ratio of innate immune cells to adaptive immune cells is determined in a sample from the subject with RA before an RA therapeutic is administered to the subject, e.g., an RA therapeutic other than an anti-TNF therapeutic. In some embodiments, the ratio of innate immune cells to adaptive immune cells is determined in a sample from the subject with RA shortly before or at the same time that an RA therapeutic is administered to the subject, e.g., an RA therapeutic other than an anti-TNF therapeutic.

In some embodiments, the ratio of innate immune cells (e.g., neutrophils) to adaptive immune cells (e.g., adaptive immune cells) is compared to a reference ratio of innate immune cells to adaptive immune cells. The reference ratio can be based on the ratio of innate immune cells to adaptive immune cells in a sample from a population of subjects with RA that yields a certain likelihood of response to anti-TNF therapeutic (e.g., and anti-TNF antibody). When the ratio of innate immune cells to adaptive immune cells in the subject sample is considered moderate or high relative to the reference ratio, then the subject is considered more likely to respond to an anti-TNF therapeutic, i.e., the anti-TNF therapeutic will cause a reduction in RA symptoms in the subject. When the ratio of innate immune cells to adaptive immune cells in the subject sample is considered low relative to the reference ratio, then the subject is considered less likely to respond to an anti-TNF therapeutic. In some embodiments, the reference ratio is the lowest 25% of the ratios of innate immune cells to adaptive, immune cells in a population of RA patients. In some embodiments, a reference ratio can be the ratio above which there is at least an 60%, 65%, 70%, 75% or greater chance that a patient will respond the therapy.

In some embodiments, the ratio of innate, immune cells to adaptive immune cells in a sample from a subject with RA is compared to the ratios of innate immune cells to adaptive immune cells in a population of subjects with RA. In some embodiments, if the ratio of innate immune cells to adaptive immune cells in sample from a subject with RA is higher than the lowest 25% of the ratios of innate immune cells to adaptive immune cells in the population of subjects with RA, then the subject is likely or more likely to respond to an anti-TNF therapeutic and the subject should be considered treatment with anti-TNF therapeutic. In some embodiments, if the ratio of innate immune cells to adaptive immune cells in sample from a subject with RA is lower than the lowest 25% of the ratios of innate immune cells to adaptive immune cells in the population of subjects with RA, then the subject is unlikely or less likely to respond to an anti-TNF therapeutic and the subject should be considered treatment with a therapeutic other than an anti-TNF therapeutic (i.e., a therapeutic that is not an anti-TNF therapeutic).

In some embodiments, the ratio of neutrophils and/or monocytes to B cells and/or T cells in a sample from a subject with RA is compared to the ratios of neutrophils and/or monocytes to B cells and/or T cells in a population of subjects with RA. In some embodiments, if the ratio of neutrophils and/or monocytes to B cells and/or T cells in sample from a subject with RA is higher than the lowest 25% of the ratios of neutrophils and/or monocytes to B cells and/or T cells in the population of subjects with RA, then the subject is likely or more likely to respond to an anti-TNF therapeutic and the subject should be considered treatment with anti-TNF therapeutic. In some embodiments, if the ratio of neutrophils and/or monocytes to B cells and/or T cells in sample from a subject with RA is lower than the lowest 25% of the ratios of neutrophils and/or monocytes to B cells and/or T cells in the population of subjects with RA, then the subject is unlikely or less likely to respond to an anti-TNF therapeutic and the subject should be considered treatment with a therapeutic other than an anti-TNF therapeutic (i.e., a therapeutic that is not an anti-TNF therapeutic).

In some embodiments, the NLR in a sample from a subject with BA is compared to the NLRs in a population of subjects with RA. In some embodiments, if the NLR in sample from a subject with RA is higher than the lowest 25% of the NLRB in the population of subjects with RA, then the subject is likely or more likely to respond to an anti-TNF therapeutic and the subject should be considered treatment with anti-TNF therapeutic. In some embodiments, if the NLR in sample from a subject with RA is lower than the lowest 25% of the NLRs in the population of subjects with RA, then the subject is unlikely or less likely to respond to an anti-TNF therapeutic and the subject should be considered treatment with a therapeutic other than an anti-TNF therapeutic (i.e., a therapeutic that is not an anti-TNF therapeutic).

In some embodiments, the ratio of neutrophils to white blood cells in a sample from a subject with BA is compared to the ratios of neutrophils to white blood cells in a population of subjects with RA. In some embodiments, if the ratio of neutrophils to white blood cells in sample from a subject with RA is higher than the lowest 25% of the ratios of neutrophils to white blood cells in the population of subjects with RA, then the subject is likely or more likely to respond to an anti-TNF therapeutic and the subject should be considered treatment with anti-TNF therapeutic. In some embodiments, if the ratio of neutrophils to white blood cells in sample from a subject with RA is lower than the lowest 25% of the ratios of neutrophils to white blood cells in the population of subjects with RA, then the subject is unlikely or less likely to respond to an anti-TNF therapeutic and the subject should be considered treatment with a therapeutic other than an anti-TNF therapeutic (i.e., a therapeutic that is not an anti-TNF therapeutic).

In some embodiments, the NWR in a sample from a subject with RA is compared to the NWRs in a population of subjects with RA. In some embodiments, if the NWR in sample from a subject with RA is higher than the lowest 25% of the NWRs in the population of subjects with RA, then the subject is likely or more likely to respond to an anti-TNF therapeutic and the subject should be considered treatment with anti-TNF therapeutic. In some embodiments, if the NWR in sample from a subject with RA is lower than the lowest 25% of the NWRs in the population of subjects with RA, then the subject is unlikely or less likely to respond to an anti-TNF therapeutic and the subject should be considered treatment with a therapeutic other than an anti-TNF therapeutic (i.e., a therapeutic that is not an anti-TNF therapeutic). In some embodiments, the ratio of innate immune cells to adaptive immune cells is determined as the log of the ratio of neutrophils to lymphocytes in a sample from a subject with RA (Ln(NLR). In some embodiments, a subject with RA is administered an anti-TNF therapeutic when the Ln(NLR) is greater than 0.6 e.g., the Ln(NLR) is 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 or more. In some embodiments, a subject with RA is administered an anti-TNF therapeutic when the Ln(NLR) is between 0.6 and 3.0. e.g., 0.6 to 2.0, 1.0 to 2.0, 1.3 to 1.6, 1.2 to 1.8, 1.2 to 2.2, 1.5 to 2.5, 1.3 to 2.3, 1.5 to 2.5, or 2.0 to 3.0.

In some embodiments, a subject with RA is administered a therapeutic other than anti-TNF (i.e., a therapeutic that is not anti-TNF) when the Ln(NLR) is less than 0.6, e.g., the Ln(NLR) is 0.55, 0.5, 0.45, 0.4, 0.35, 0.3, 0.25, 0.2, 0.15, 0.1, or 0.05 or less. In some embodiments, a subject with RA is administered a therapeutic other than anti-TNF when the Ln(NLR) is between 0.1 and 0.59. e.g., 0.1 to 0.5, 0.2 to 0.59, or 0.2 to 0.4.

In some embodiments, a subject with HA can be selected for anti-TNF treatment based on an assessment of the number of innate immune cells and/or adaptive immune cells in a sample, e.g., a blood sample, collected from the subject prior to anti-TNF treatment. Any methods known in the art for identifying and counting immune cells in a sample, e.g., a clinical blood sample, can be used to determine the number of innate and/or adaptive immune cells in the sample collected from the subject with RA. The number of innate and/or adaptive immune cells can be counted in the sample by any suitable clinical cell counting methodology known in the art. In some embodiments, the types and numbers of immune cells in the sample is determined by a blood cell count, e.g., a complete blood count (CBC) or differential blood cell count, using methods known in the art. In some embodiments, the types and numbers of immune cells in the sample can be determined by FACS analysis of cells in the sample, e.g., a blood sample.

In some embodiments, a subject with RA can be selected for anti-TNF treatment based on an assessment of the levels of molecular signatures for innate immune cells types and/or adaptive immune cell types in a sample, e.g., a blood sample, collected from the subject prior to anti-TNF treatment. In some embodiments, the molecular signature can be the gene expression level of one or more genes whose expression is closely associated with an innate or adaptive immune cell type. In some embodiments, the molecular signature can be the protein expression level of one or more proteins whose expression is closely associated with an innate or adaptive immune cell type. Any methods known in the art for measuring and analyzing gene or protein expression can be used to assess the molecular signature of innate and adaptive immune cells, including, but not limited to, FACS analysis, polymerase chain reaction e.g., RT-PCR of mRNA), microarrays, mass spectrometry, proteomics, etc.

In some embodiments, determining the ratio of innate immune cells to adaptive immune cells in a sample from the subject with RA (e.g., in determining whether the subject has a high ratio of innate immune cells to adaptive immune cells) can include determining the expression in the sample of one or more genes in FIG. 6, e.g., one or more genes in FIG. 6 associated with an innate immune response and/or an adaptive immune response. In some embodiments, determining the ratio of innate immune cells to adaptive immune cells in a sample from the subject with RA (e.g., in determining whether the subject has a high ratio of innate immune cells to adaptive immune cells) can include determining the expression in the sample of one or more genes in FIG. 6 associated with an innate immune response and/or one or more genes in FIG. 6 associated with an adaptive immune response, e.g., 1, 2, 3, 4, 5, 6, 7, 8, 9, 10, 11, 1.2, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 300, 35, 400, or 420 or more genes in FIG. 6.

In some embodiments, determining the ratio of innate immune cells to adaptive immune cells in a sample (e.g., a blood sample) from the subject with RA (e.g., in determining whether the subject has a high ratio of innate immune cells to adaptive immune cells) can include determining the expression of one or more of CD14, CD36, CD46, CD47, CD163, CD164, CD52, CD48, CD3D, CD8A, CD79D, and CD22 in the sample, e.g., determining the expression of 1, 2, 3, 4, 5, 6, 7, 8, 9, 10, 11, or 12 of CD14, CD36, CD46, CD47, CD163, CD164, CD52, CD48, CD3D, CD8A, CD79D, and CD22 in the sample. In some embodiments, the gene expression of CD14, CD36, CD46, CD47, CD163, CD164, CD52, CD48, CD3D, CD8A, CD79D, and/or CD22 is determined. In some embodiments, the protein expression of CD14, CD36, CD46, CD47, CD163, CD164, CD52, CD48, CD3D, CD8A, CD79D, and CD22 is determined. In some embodiments, the anti-TNF therapeutic can be an anti-TNF antibody. In some embodiments, the anti-TNF therapeutic is infliximab, adalimumab, golimumab, certolizumab pegol or etanercept. In some embodiments, the subject is administered methotrexate with an anti-TNF therapeutic. In some embodiments, the subject is not administered methotrexate with an anti-TNF therapeutic.

In some embodiments, the rheumatoid arthritis treatment other than an anti-TNF therapeutic (i.e., the therapeutic that is not anti-TNF) is an anti-CD20 antibody, an anti-IL-6R antibody or a CLTA-4-Ig fusion protein. In some embodiments, the rheumatoid arthritis treatment other than an anti-TNF therapeutic (i.e., the therapeutic that is not anti-TNF) is abatacept, rituximab or tocilizumab.

As used herein, the term "biological sample" or "sample" refers to a sample obtained, collected, or derived from a subject. The sample can include any bodily fluid (e.g., blood, whole blood, plasma, serum, mucus secretions, urine, sputum, lymph fluids, gynecological fluids, cystic fluid, cerebrospinal fluid, fluids collected from bronchial lavage, or saliva), cell, tissue, feces, or cell extracts from a subject.

EXAMPLES

The invention is further described in the following examples, which do not limit the scope of the invention described in the claims.

Example 1: Materials and Methods

Study Design and Sample Selection Criteria

A comprehensive molecular profiling study of rheumatoid arthritis (RA) patients starting anti-TNF-alpha therapy (or "anti-FNF" therapy or treatment) was conducted. Samples were collected and profiled from biologic naïve RA patients being treated with anti-TNF-alpha therapy in combination with methotrexate (MTX) at two time points: first at a time point prior to initiating anti-TNF-alpha therapy (the "baseline" time point) and then again 3 months after treatment with anti-TNF-alpha therapy. The aim of the study was to understand the molecular mechanisms (other than drug neutralization) that affect clinical response to anti-TNF-alpha, and to identify markers that could be used to predict, prior to administering anti-TNF treatment (at baseline), which RA patients will likely exhibit a good or moderate response to anti-TNF treatment ("responders", "good responders", or "moderate responders") versus those RA patients that will likely exhibit no response or a poor response to anti-TNF treatment ("poor responders" or "non-responders").

Rheumatoid arthritis (RA) patient samples were obtained, and samples (whole blood and plasma) from RA patients that were biologic naïve (i.e., received no prior treatment with a biologic agent), were initiating treatment with an anti-TNF therapeutic (either adalimumab or infliximab) in conjunction with methotrexate (MTX), and had no or stable low dose prednisone (<5 mg) were selected. Response of each RA patient to anti-TNF therapy at 3 months was evaluated using European League Against Rheumatism (EULAR) criteria. Patients were included in the study cohorts only if a minimum level of anti-TNF therapeutic (Humira® (adalimumab) or Remicade® (infliximab)) was detected in the 3 month plasma sample by a drug specific ELISA to assure drug exposure. Patients with drug levels of less than 800 ng/mL were excluded.

Patients Characteristics

Samples from RA patients were selected and split in two independent cohorts of 40 RA patients (Cohort 1 (C1)) and 36 RA patients (Cohort 2 (C2)) for the molecular profiling study. All patients in both cohorts were biologic-naïve and undergoing treatment with methotrexate (MTX). Table 1 provides the demographic and clinical information for good and poor responders in Cohorts 1 and 2. Based on assessment of EULAR improvement criteria, 52.5% of patients (21 patients) from C1 were determined to be non-responders [NR] (or "poor" responders) and 47.5% of patients (19 patients) were moderate/good responders [R], while 41.7% of patients (15 patients) from C2 were determined to be non-responders and 58.3 moderate/good responders (21 patients). Poor responders exhibited higher levels of tender joint counts, Disease Activity Score 28-joint count C reactive protein (DAS28-CRP) at baseline, and, as a group, exhibited a lower percentage of CCP- and RF-positive subjects. Although samples were selected from both cohorts to match clinical and demographic measures across multiple covariates, a difference in significant smoking status was observed, due to a higher frequency of smokers in good responders in C1, compared to C2. Good responders in C2 exhibited higher swollen 28-joint count (SJC28) and tender joint counts at baseline, DAS28-CRP at baseline, and poor responders from C2 showed higher ln(CRP) at baseline and longer RA duration than poor responders from C1. Although these differences between the cohorts may affect the comparability of the two cohorts at the molecular level, none of these results reached statistical significance (see Table 1).

TABLE 1

Demographic and clinical information for good and poor responders in Cohorts 1 and 2.

| | Cohort 1 | | | Cohort 2 | | |
|---|---|---|---|---|---|---|
| | Good | Poor | p | Good | Poor | p |
| N | 19 | 21 | N/A | 21 | 15 | N/A |
| Female, N (%)‡ | 15 (79) | 19 (90) | 0.4 | 16 (76) | 12 (80) | 1 |
| Age, mean (SD) | 54 (13) | 56 (13) | 0.58 | 55 (12) | 51 (9.9) | 0.31 |
| White, N (%) | 17 (89) | 14 (67) | 0.13 | 19 (90) | 13 (87) | 1 |
| Non-smoker, N (%) | 8 (42) | 14 (67) | 0.2 | 14 (67) | 6 (40) | 0.18 |
| Current or previous smoker, N (%) | 11 (58) | 7 (33) | 0.2 | 7 (33) | 6 (40) | 0.74 |
| Remicade, N (%) | 8 (42) | 9 (43) | 1 | 6 (29) | 8 (53) | 0.18 |
| Humira, N (%) | 11 (58) | 12 (57) | 1 | 15 (71) | 7 (47) | 0.18 |
| SJC28 [BL], mean (SD) | 6.7 (3.7) | 9.1 (5.5) | 0.12 | 9.6 (5.5) | 8.7 (4.9) | 0.62 |
| TJC28 [BL], mean (SD)* | 9 (6.2) | 15 (8.3) | 0.015 | 11 (6.7) | 14 (5.7) | 0.31 |
| ln(CRP) [BL], mean (SD) | 1.6 (1.6) | 1.2 (1.8) | 0.49 | 1.5 (1.4) | 1.8 (1.1) | 0.54 |
| DAS28CRP [BL], mean (SD)* | 4.5 (0.78) | 5.2 (0.94) | 0.014 | 4.8 (0.83) | 5.2 (0.66) | 0.094 |
| DAS28CRP [BL-MO3], mean (SD)§ | 2.7 (0.8) | 0.095 (0.33) | 4.7e−16 | 2.9 (0.86) | 0.0073 (0.67) | 2.2e−12 |
| RA duration, mean (SD)* | 5.4 (7.5) | 1.9 (1.7) | 0.043 | 5 (6.5) | 7.2 (8.3) | 0.39 |
| RF+, N (%) | 16 (84) | 12 (57) | 0.089 | 16 (76) | 8 (53) | 0.18 |
| CCP+, N (%)* | 16 (84) | 8 (38) | 0.0041 | 16 (76) | 6 (40) | 0.032 |

‡Numbers in brackets after each attribute represent percentages or standard deviation (SD) of that attribute, as indicated.
*Difference between good and poor responders at baseline for this attribute is statistically significant (p < 0.05) in at least one of the cohorts.
§DAS28CRP [BL-MO3] reflects the change in DAS28CRP score from baseline to month 3. Therefore, this attribute is a metric of response, and is expected to be different between good and poor responders.

Sample Handling, Processing; and Analysis

Whole-blood RNA samples (PAXgene) and plasma samples collected prior to initiating anti-TNF therapy (baseline) and following 3 months of anti-TNF treatment from the patients selected in each cohort were profiled using different technologies (RNAseq, proteomics and targeted glycopeptide analysis). Samples from each cohort were randomized with respect to study factors related to sample handling, processing and data acquisition (e.g. shotgun proteomics run order, RNA extraction, NGS sequencing batches, etc.). Cohort 2 samples were analyzed independently from Cohort 1 samples, and around 12 months after the Cohort 1 samples were analyzed.

Plasma Sample Processing

De-identified plasma samples were obtained for shotgun proteomic analysis. Plasma ID numbers were assigned at random to all plasma samples. Samples were then processed in the order of plasma ID numbers to insure minimal bias due to run order. Samples were processed and run as sets of 20 samples. A normal human plasma control (obtained from Sigma-Aldrich) was included with each set. Plasma samples were first depleted of the top 14 most abundant proteins using Multiple Affinity Removal System 14 (MARS-14), an immunoaffinity, HPLC-based methodology. Removal of high abundant proteins allows for the detection of medium to low abundant proteins by shotgun proteomics. A bicinchoninic acid (BCA) assay was then performed to determine protein concentration.

Proteomics Analysis by LC-MS/MS

For each sample, 50 μs of total protein was aliquoted for digestion using trypsin/Lys-C. The resulting peptide mixtures were separated using an Ultimate 3000 RSLC nano system. Peptides were loaded onto an Acclaim Pep Map RSLC Nano trap column (5 μm particle size, 20 mm×100 urn at 5 $\mu L min^{-1}$ flow rate and resolved on the basis of hydrophobicity using an EASY-Spray Acclaim PepMap RSLC C18 column. MS analyses were performed on Orbitrap Velos Pro in the positive-ion mode using an EASY-Spray nano-source. RAW files from the mass spectrometer were searched using Sequest HT as part of Proteome Discoverer 1.4 mass informatics software package. Files were searched against the human Uniprot database (including protein isoforms) and then opened as a multiconsensus report (5% peptide-level false discovery rate). Results were then exported into Microsoft Excel for further data analysis and normalized to total PSM for each sample to account for sample-to-sample variation.

Targeted Glycopeptide Analysis of Shed Fc Receptors in Plasma by LC-MS/MS Analysis Soluble FcγRs were isolated from 50 μL of plasma. Proteins were immunoprecipitated using biotinylated goat polyclonal antibodies against human FcγRIII (R&D Systems BAF1597) and human FcγRII (R&D Systems BAF1330). Marker peptides for polymorphic variants of both FcγRIIIb and FcγRIIa, as well as glycosylation of FcγRIII N45, were characterized using a chymotryptic digestion (Sequencing Grade Promega V1061). The peptides and glycopeptides were analyzed by nano LC-MS/MS on a Dionex Ultimate 3000 nano RSLC coupled to a QExactive mass spectrometer (ThermoFisher Scientific) equipped with and EasySpray nano-LC source (ThermoFisher Scientific). Peptides were separated on an EasySpray C18 column (0.75×250 mm 2 μm particle size). A targeted nLC-MS/MS method was applied for the quantitation of site specific glycosylation as well as assignment of allelic variants based on peptide sequence information. The quadrapole isolation width was set to +1 Da for the isolation of the parent ion of each of the species. Targeted species were quantified based on the extracted ion abundance for the peptide+GlcNAc fragment. The abundance was determined for each species relative to the summed extracted ion area for each site of glycosylation.

RNA Preparation and NGS Sequencing (RNA-seq)

RNA was extracted from human whole blood samples preserved in PAXgene tubes (Qiagen). RNA extraction was performed according to the PAXGene Blood miRNA kit protocol (C1) or PAXGene Blood RNA kit protocol (C2) using the QIAcube instrument (Qiagen). RNA concentration was measured by absorbance at 260 nm, and RNA quality was measured by the Agilent TapeStation and Agilent Bioanalyzer. Libraries were prepared for RNAseq analysis with the Apollo 324 system from WaferGen Biosystems using the WaferGen Prep-X Directional RNA-Seq kit (CD or Illumina's TruSeq Stranded mRNA Library Preparation Kit (C2) according to manufacturer's protocols. Libraries were sequenced on an Illumina HiSeq 2500 for 40×40 bases (C1), and 75×75 bases (C2), in paired end, high output mode.

FASTQ files were mapped to human reference (UCSC hg19) genome using two pass STAR alignment. QC metrics of resulting BAM files were obtained using RNAseQC. Gene counts were generated by featureCounts software program.

Data Analysis

All analyses of differential gene and protein expression were performed using limma-voom methodology. Multiple test correction for genome-wide assays (RNA-seq, shotgun proteomics) were performed using the Benjamini-Hochberg procedure. Non-parametric (Spearman's) rank correlation was used for assessing global concordance of gene/protein-level differences throughout. The statistical significance of correlations and counts of genes or proteins passing significance cutoffs where applicable was estimated by permutation. The results of such tests were deemed statistically significant if more extreme (by absolute value) statistic (e.g. correlation coefficient, protein count, etc.) was obtained in fewer than 5% of permutations. Adjustment for confounding factors, such as between subject variability, sample processing order in shotgun proteomics or systematic biases as revealed by RNA-SeQC metrics was accomplished by including corresponding terms into statistical model using limma-voom methodology.

The association between baseline neutrophils and lymphocytes and EULAR response was further evaluated among biologic initiators that were not included in the initial cohorts studied (C1 and C2). These initiators were categorized into one of the four following groups based on the characteristics of their biologic initiation and line of therapy (naïve vs experienced biologic use): 1) biologic-naïve TNF initiator, 2) biologic-experienced TNF initiator, 3) biologic-naïve non-TNF initiator, or 4) biologic-experienced non-TNF initiator. EULAR response at 3 month follow-up visit was evaluated and patients were further categorized as moderate to good EULAR response or poor EULAR response. Baseline (at time of initiation) neutrophils, lymphocytes and white blood counts (WBC) were available and from these baseline measures, the following ratios were calculated: 1) Neutrophil:lymphocyte log ratio=ln(neutrophils/lymphocytes), 2) Neutrophil:WBC log ratio=ln(neutrophils/WBC) and 3) Lymphocyte:WBC log ratio=ln(lymphocytes/WBC). Logistic regression was used to evaluate the association between baseline neutrophil:lymphocyte log ratio and EULAR response without covariate adjustment and adjusted by drug group and a priori selected variables (age at drug initiation, smoking status, years of disease duration at initiation, modified HAQ at initiation, concomitant MTX use at time of initiation of drug, number of prior biologics used at time of initiation). In a similar fashion, the association between baseline neutrophil:WBC log ratios and EULAR response, and lymphocyte:WBC log ratios and FULA response, were estimated.

Example 2: Molecular Signature of Anti-TNF Treatment

The genome-wide gene expression levels obtained prior to initiating anti-TNF therapy and the genome-wide expression levels obtained after 3 months of anti-TNF treatment were compared among patients in each cohort (C1 and C2), irrespective of the EULAR response status of the patients.

Figure 1B:
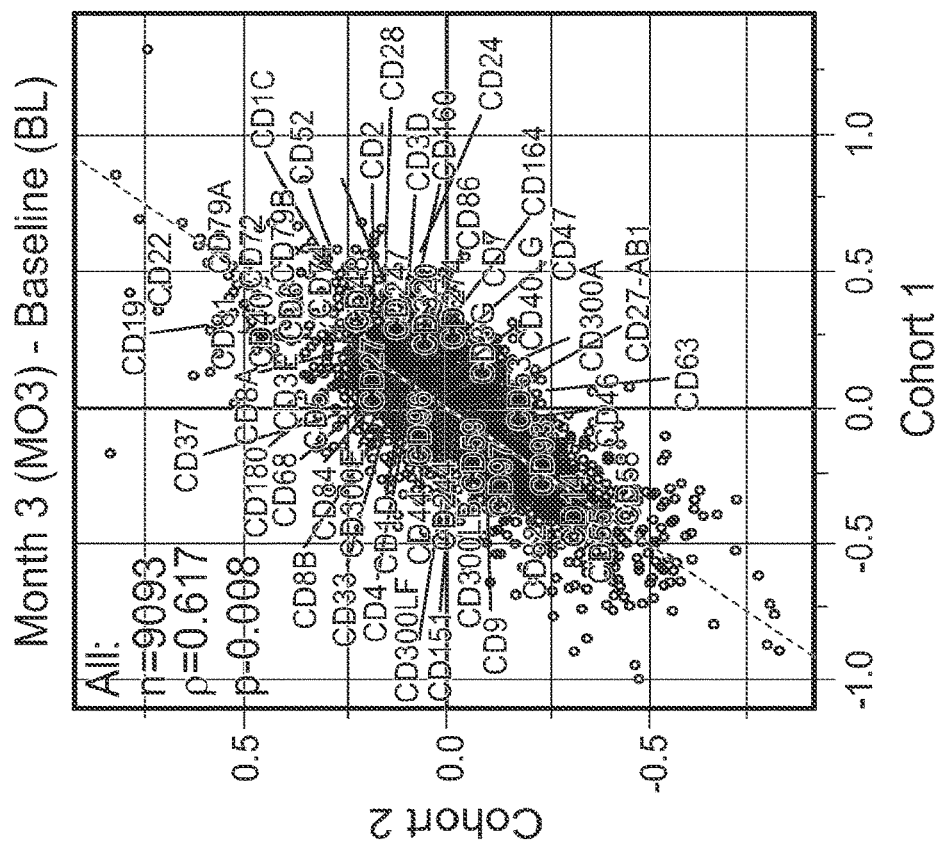
FIG. 1B is a graph showing changes in gene expression after 3 months of anti-TNF treatment (MO3) relative to baseline (BL), with gene sets related to particular cell types (myeloid cells, B cells, and T cells) highlighted, plotted for Cohort 1 (C1) versus Cohort 2 (C2).
Figure 1A:
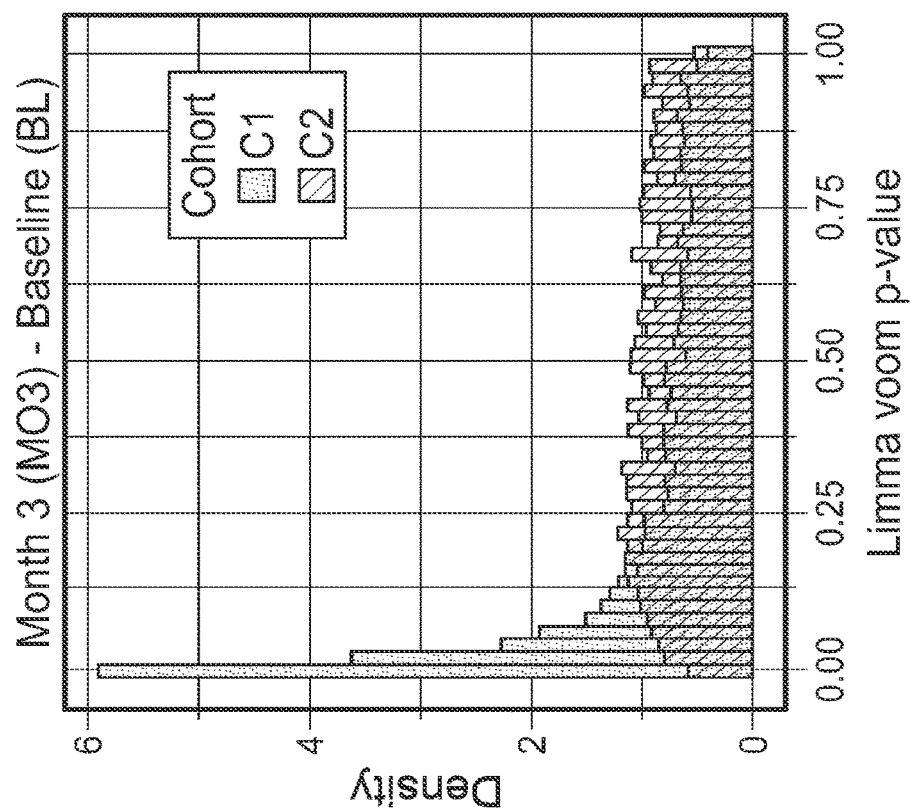
FIG. 1A is a bar graph showing changes in whole-blood gene expression after 3 months of anti-TNF treatment (MO3) relative to baseline (BL) for Cohort 1 (C1) and Cohort 2 (C2), plotted according to statistical significance (distribution of p-values).

FIG. 1A shows the distribution of p-values for the differences in gene expression after 3 months of treatment relative to baseline for C1 and C2. Substantial numbers of genes achieved low False Discovery Rate (FDR) levels (775 genes at B-H FDR<0.05) in C1, but not in C2 (3 genes at BH-FDR<0.05). This result could possibly be explained by a lower power because of a smaller number of paired samples in C2 (n32 in C1 vs. n=20 in C2).

FIG. 1B shows the mean differences in gene expression levels between the baseline and 3 month expression levels for C1 and C2, with certain genes highlighted (e.g., markers for myeloid, B, and T cells). A consistent anti-TNF treatment effect is manifested as a strong positive correlation in the mean differences of gene expression levels (at baseline vs. 3 months after treatment) observed for C1 and C2. A high level of correlation in the changes in gene expression between the baseline and 3 month expression levels was observed for both cohorts. The majority of genes exhibiting the largest differences between their month 3 and baseline levels in both cohorts were down-regulated and related to myeloid cells (see, Table 2). Granulocyte functions appeared to be prominently modulated with, in particular, functions related to degranulation, chemotaxis and migration. Platelet-related genes were also significantly down-regulated. The majority of the up-regulated genes were involved in protein synthesis, including transcription, translation and ribosome-related genes (see, Table 2). This result was confirmed by the analysis of the most significantly modulated cell surface markers (see, FIG. 1B). T and B cell marker (i.e. CD3, CD4, CD8, CD79, CD22 and CD52) were significantly up-regulated in both cohorts, while myeloid markers (CD14, CD55, CD46) were down-regulated

TABLE 2

Gene ontology analysis of the genes modulated between baseline and 3-month following anti-TNF treatment

| GO ID | Term | Number of genes | Direction | p-value | FDR |
|---|---|---|---|---|---|
| GO:0042581 | Specific granule | 123 | Down | 0 | 0 |
| GO:0035580 | Specific granule lumen | 43 | Down | 0 | 0 |
| GO:0019730 | Antimicrobial humoral response | 37 | Down | 0 | 0 |
| GO:0051852 | Disruption by host of symbiont cells | 9 | Down | 0 | 0 |
| GO:0030667 | Secretory granule membrane | 215 | Down | 0 | 1E−07 |
| GO:0051818 | Disruption of cells of other organism Involved in symbiotic interaction | 10 | Down | 0 | 1E−07 |
| GO:0070820 | Tertiary granule | 129 | Down | 0 | 2E−07 |
| GO:0101003 | Ficolin-1-rich granule membrane | 50 | Down | 0 | 2E−07 |
| GO:0004875 | Complement receptor activity | 6 | Down | 0 | 3E−07 |
| GO:0002251 | Organ or tissue specific immune response | 11 | Down | 0 | 4E−07 |
| GO:0002385 | Mucosal immune response | 10 | Down | 0 | 0.000001 |
| GO:0002227 | Innate immune response in mucosa | 9 | Down | 0 | 1.8E−06 |
| GO:0051873 | Killing by host of symbiont cells | 7 | Down | 0 | 5.6E−06 |
| GO:0051883 | Killing of cells in other organism involved in symbiotic interaction | 8 | Down | 0 | 8.1E−06 |
| GO:1904724 | Tertiary granule lumen | 43 | Down | 0 | 8.7E−06 |
| GO:0042119 | Neutrophil activation | 412 | Down | 0 | 0.000009 |
| GO:0002446 | Neutrophil mediated immunity | 413 | Down | 0 | 9.1E−06 |
| GO:0002283 | Neutrophil activation involved in immune response | 406 | Down | 0 | 9.1E−06 |
| GO:0043312 | Neutrophil degranulation | 405 | Down | 0 | 1.03E−05 |
| GO:1990266 | Neutrophil migration | 47 | Down | 0 | 1.04E−05 |
| GO:0030141 | Secretory granule | 514 | Down | 1E−07 | 1.39E−05 |
| GO:0036230 | Granulocyte activation | 416 | Down | 1E−07 | 1.43E−05 |
| GO:0019731 | Antibacterial humoral response | 14 | Down | 1E−07 | 1.47E−05 |
| GO:0030593 | Neutrophil chemotaxis | 40 | Down | 1E−07 | 1.47E−05 |
| GO:0043299 | Leukocyte degranulation | 433 | Down | 1E−07 | 1.55E−05 |
| GO:0019229 | Regulation of vasoconstriction | 11 | Down | 1E−07 | 2.13E−05 |
| GO:0002444 | Myeloid leukocyte mediated immunity | 439 | Down | 1E−07 | 2.16E−05 |
| GO:0002275 | Myeloid cell activation involved in immune response | 436 | Down | 1E−07 | 2.55E−05 |
| GO:0045055 | Regulated exocytosis | 527 | Down | 2E−07 | 0.000029 |
| GO:0097530 | Granulocyte migration | 58 | Down | 2E−07 | 3.26E−05 |
| GO:0071621 | Granulocyte chemotaxis | 49 | Down | 2E−07 | 3.26E−05 |
| GO:0099503 | Secretory vesicle | 562 | Down | 2E−07 | 3.48E−05 |
| GO:1902622 | Regulation of neutrophil migration | 19 | Down | 3E−07 | 4.21E−05 |
| GO:0031091 | Platelet alpha granule | 46 | Down | 4E−07 | 6.71E−05 |
| GO:0005161 | Platelet-derived growth factor receptor binding | 8 | Down | 6E−07 | 8.59E−05 |
| GO:0002274 | Myeloid leukocyte activation | 492 | Down | 7E−07 | 0.0001 |
| GO:0006023 | Aminoglycan biosynthetic process | 43 | Down | 7E−07 | 0.0001 |
| GO:0031424 | Keratinization | 19 | Down | 1.3E−06 | 0.000182 |
| GO:0008146 | Sulfotransferase activity | 16 | Down | 2.1E−06 | 0.000276 |
| GO:0035579 | Specific granule membrane | 73 | Down | 2.1E−06 | 0.000276 |

TABLE 2-continued

Gene ontology analysis of the genes modulated between
baseline and 3-month following anti-TNF treatment

| GO ID | Term | Number of genes | Direction | p-value | FDR |
|---|---|---|---|---|---|
| GO:0051923 | Sulfation | 6 | Down | 2.2E−06 | 0.000281 |
| GO:0006887 | Exocytosis | 600 | Down | 2.3E−06 | 0.000297 |
| GO:0006024 | Glycosaminoglycan biosynthetic process | 42 | Down | 2.9E−06 | 0.000363 |
| GO:0097756 | Negative regulation of blood vessel diameter | 18 | Down | 0.000003 | 0.000363 |
| GO:0050832 | Defense response to fungus | 16 | Down | 0.000003 | 0.000363 |
| GO:0019915 | Lipid storage | 36 | Down | 3.4E−06 | 0.000406 |
| GO:0070821 | Tertiary granule membrane | 59 | Down | 3.4E−06 | 0.000408 |
| GO:0006022 | Aminoglycan metabolic process | 71 | Down | 4.1E−06 | 0.000478 |
| GO:0006527 | Arginine catabolic process | 5 | Down | 4.8E−06 | 0.00056 |
| GO:0010745 | Negative regulation of macrophage derived foam cell differentiation | 7 | Down | 5.1E−06 | 0.000587 |
| GO:0010888 | Negative regulation of lipid storage | 11 | Down | 5.5E−06 | 0.000626 |
| GO:0010743 | Regulation of macrophage derived foam cell differentiation | 13 | Down | 5.7E−06 | 0.000645 |
| GO:0005520 | Insulin-like growth factor binding | 6 | Down | 7.2E−06 | 0.000773 |
| GO:0072672 | Neutrophil extravasation | 6 | Down | 7.5E−06 | 0.000795 |
| GO:1905953 | Negative regulation of lipid localization | 18 | Down | 7.6E−06 | 0.000809 |
| GO:0097529 | Myeloid leukocyte migration | 79 | Down | 7.9E−06 | 0.000825 |
| GO:0042310 | Vasoconstriction | 17 | Down | 8.9E−06 | 0.000917 |
| GO:1902624 | Positive regulation of neutrophil migration | 16 | Down | 8.9E−06 | 0.000917 |
| GO:0070268 | Cornification | 15 | Down | 9.7E−06 | 0.000997 |
| GO:0061844 | Antimicrobial humoral immune response mediated by antimicrobial peptide | 21 | Down | 1.04E−05 | 0.001029 |
| GO:0030203 | Glycosaminoglycan metabolic process | 67 | Down | 1.04E−05 | 0.001029 |
| GO:0002576 | Platelet degranulation | 70 | Down | 1.15E−05 | 0.001111 |
| GO:0019233 | Sensory perception of pain | 23 | Down | 1.44E−05 | 0.001379 |
| GO:1903510 | Mucopolysaccharide metabolic process | 55 | Down | 1.71E−05 | 0.001634 |
| GO:0002263 | Cell activation involved in immune response | 530 | Down | 1.85E−05 | 0.001758 |
| GO:0002366 | Leukocyte activation involved in immune response | 527 | Down | 1.88E−05 | 0.00176 |
| GO:0030730 | Sequestering of triglyceride | 8 | Down | 0.000021 | 0.001941 |
| GO:0031225 | Anchored component of membrane | 34 | Down | 2.12E−05 | 0.001942 |
| GO:0050542 | Icosanoid binding | 5 | Down | 2.47E−05 | 0.002253 |
| GO:0031092 | Platelet alpha granule membrane | 13 | Down | 2.91E−05 | 0.002577 |
| GO:0031640 | Killing of cells of other organism | 25 | Down | 2.99E−05 | 0.002603 |
| GO:0090022 | Regulation of neutrophil chemotaxis | 17 | Down | 0.00003 | 0.002603 |
| GO:0043691 | Reverse cholesterol transport | 6 | Down | 3.33E−05 | 0.002863 |
| GO:0031093 | Platelet alpha granule lumen | 32 | Down | 3.41E−05 | 0.002902 |
| GO:0051931 | Regulation of sensory perception | 8 | Down | 3.63E−05 | 0.002945 |
| GO:0006954 | Inflammatory response | 345 | Down | 3.91E−05 | 0.003129 |
| GO:0016755 | Transferase activity, transferring amino-acyl groups | 7 | Down | 4.05E−05 | 0.003208 |
| GO:0046903 | Secretion | 875 | Down | 4.73E−05 | 0.0037 |
| GO:0050996 | Positive regulation of lipid catabolic process | 9 | Down | 5.66E−05 | 0.004355 |
| GO:0006940 | Regulation of smooth muscle contraction | 12 | Down | 5.74E−05 | 0.004394 |
| GO:0018149 | Peptide cross-linking | 11 | Down | 5.83E−05 | 0.00445 |
| GO:0032637 | Interleukin-8 production | 49 | Down | 6.14E−05 | 0.004667 |
| GO:0050786 | RAGE receptor binding | 8 | Down | 7.33E−05 | 0.005498 |
| GO:0032940 | Secretion by cell | 833 | Down | 7.38E−05 | 0.005515 |
| GO:0030335 | Positive regulation of cell migration | 204 | Down | 7.58E−05 | 0.005638 |
| GO:0010883 | Regulation of lipid storage | 25 | Down | 8.29E−05 | 0.00612 |
| GO:0010742 | Macrophage derived foam cell differentiation | 17 | Down | 8.94E−05 | 0.006498 |
| GO:0040017 | Positive regulation of locomotion | 222 | Down | 0.000092 | 0.006607 |
| GO:0042742 | Defense response to bacterium | 100 | Down | 9.43E−05 | 0.006741 |
| GO:0030198 | Extracellular matrix organization | 96 | Down | 9.69E−05 | 0.006828 |
| GO:0000272 | Polysaccharide catabolic process | 18 | Down | 0.000103 | 0.007088 |
| GO:0045907 | Positive regulation of vasoconstriction | 5 | Down | 0.000105 | 0.007107 |
| GO:0015721 | Bile acid and bile salt transport | 9 | Down | 0.000106 | 0.007202 |
| GO:2000147 | Positive regulation of cell motility | 206 | Down | 0.000116 | 0.007858 |
| GO:0032496 | Response to lipopolysaccharide | 182 | Down | 0.000123 | 0.008212 |
| GO:0035994 | Response to muscle stretch | 10 | Down | 0.000129 | 0.008445 |
| GO:0034774 | Secretory granule lumen | 225 | Down | 0.000132 | 0.008571 |
| GO:1903524 | Positive regulation of blood circulation | 16 | Down | 0.000137 | 0.008649 |
| GO:0032677 | Regulation of interleukin-8 production | 45 | Down | 0.000139 | 0.008777 |
| GO:0006805 | Xenobiotic metabolic process | 33 | Down | 0.000141 | 0.008879 |

TABLE 2-continued

Gene ontology analysis of the genes modulated between
baseline and 3-month following anti-TNF treatment

| GO ID | Term | Number of genes | Direction | p-value | FDR |
|---|---|---|---|---|---|
| GO:0001533 | Cornified envelope | 9 | Down | 0.000147 | 0.008905 |
| GO:0045408 | Regulation of interleukin-6 biosynthetic process | 10 | Down | 0.000157 | 0.009389 |
| GO:0071622 | Regulation of granulocyte chemotaxis | 25 | Down | 0.00016 | 0.009533 |
| GO:0090136 | Epithelial cell-cell adhesion | 10 | Down | 0.00016 | 0.009533 |
| GO:0009617 | Response to bacterium | 270 | Down | 0.000166 | 0.009841 |
| GO:0006614 | SRP-dependent cotranslational protein targeting to membrane | 88 | Up | 0 | 0 |
| GO:0006613 | Cotranslational protein targeting to membrane | 93 | Up | 0 | 0 |
| GO:0022626 | Cytosolic ribosome | 95 | Up | 0 | 0 |
| GO:0045047 | Protein targeting to ER | 97 | Up | 0 | 0 |
| GO:0072599 | Establishment of protein localization to endoplasmic reticulum | 100 | Up | 0 | 0 |
| GO:0003735 | Structural constituent of ribosome | 141 | Up | 0 | 0 |
| GO:0044391 | Ribosomal subunit | 163 | Up | 0 | 0 |
| GO:0022625 | Cytosolic large ribosomal subunit | 54 | Up | 0 | 0 |
| GO:0070972 | Protein localization to endoplasmic reticulum | 116 | Up | 0 | 0 |
| GO:0000184 | Nuclear-transcribed mRNA catabolic process, nonsense-mediated decay | 114 | Up | 0 | 0 |
| GO:0042613 | MHC class II protein complex | 14 | Up | 0 | 0 |
| GO:0005840 | Ribosome | 200 | Up | 0 | 0 |
| GO:0015934 | Large ribosomal subunit | 103 | Up | 0 | 0 |
| GO:0006612 | Protein targeting to membrane | 137 | Up | 0 | 0 |
| GO:0022627 | Cytosolic small ribosomal subunit | 38 | Up | 0 | 0 |
| GO:0006413 | Translational initiation | 172 | Up | 0 | 0 |
| GO:0015935 | Small ribosomal subunit | 62 | Up | 0 | 0 |
| GO:0006364 | rRNA processing | 223 | Up | 0 | 0 |
| GO:0019083 | Viral transcription | 167 | Up | 0 | 0 |
| GO:0019080 | Viral gene expression | 181 | Up | 0 | 0 |
| GO:0042254 | Ribosome biogenesis | 276 | Up | 0 | 0 |
| GO:0032395 | MHC class II receptor activity | 8 | Up | 0 | 0 |
| GO:0016072 | rRNA metabolic process | 249 | Up | 0 | 0 |
| GO:0042611 | MHC protein complex | 23 | Up | 0 | 0 |
| GO:0044445 | Cytosolic part | 189 | Up | 0 | 0 |
| GO:0000956 | Nuclear-transcribed mRNA catabolic process | 189 | Up | 0 | 0 |
| GO:0002181 | Cytoplasmic translation | 53 | Up | 0 | 0 |
| GO:0090150 | Establishment of protein localization to membrane | 219 | Up | 0 | 0 |
| GO:0034470 | ncRNA processing | 323 | Up | 0 | 0 |
| GO:0023026 | MHC class II protein complex binding | 15 | Up | 0 | 0 |
| GO:0023023 | MHC protein complex binding | 17 | Up | 0 | 0 |
| GO:0022613 | Ribonucleoprotein complex biogenesis | 396 | Up | 0 | 0 |
| GO:0042255 | Ribosome assembly | 49 | Up | 0 | 0 |
| GO:0042273 | Ribosomal large subunit biogenesis | 58 | Up | 0 | 0 |
| GO:0019843 | rRNA binding | 51 | Up | 0 | 1E−07 |
| GO:0034660 | ncRNA metabolic process | 444 | Up | 0 | 1E−07 |
| GO:0006402 | mRNA catabolic process | 297 | Up | 0 | 8E−07 |
| GO:0002396 | MHC protein complex assembly | 5 | Up | 0 | 0.000001 |
| GO:0006401 | RNA catabolic process | 318 | Up | 0 | 1.3E−06 |
| GO:1990904 | Ribonucleoprotein complex | 663 | Up | 0 | 2.5E−06 |
| GO:0030529 | Intracellular ribonucleoprotein complex | 660 | Up | 0 | 2.7E−06 |
| GO:0000027 | Ribosomal large subunit assembly | 24 | Up | 0 | 3.7E−06 |
| GO:0006414 | Translational elongation | 105 | Up | 0 | 3.8E−06 |
| GO:0006412 | Translation | 531 | Up | 0 | 3.8E−06 |
| GO:0006605 | Protein targeting | 298 | Up | 0 | 0.000004 |
| GO:0043043 | Peptide biosynthetic process | 543 | Up | 0 | 4.2E−06 |
| GO:0042274 | Ribosomal small subunit biogenesis | 60 | Up | 0 | 0.000009 |
| GO:0098553 | Lumenal side of endoplasmic reticulum membrane | 25 | Up | 1E−07 | 1.47E−05 |
| GO:0070125 | Mitochondrial translational elongation | 79 | Up | 1E−07 | 2.29E−05 |
| GO:0000028 | Ribosomal small subunit assembly | 15 | Up | 1E−07 | 2.73E−05 |
| GO:0070126 | Mitochondrial translational termination | 80 | Up | 2E−07 | 0.000029 |
| GO:0032543 | Mitochondrial translation | 110 | Up | 2E−07 | 3.26E−05 |
| GO:0043604 | Amide biosynthetic process | 589 | Up | 2E−07 | 0.000042 |
| GO:0140053 | Mitochondrial gene expression | 116 | Up | 3E−07 | 4.55E−05 |
| GO:0005761 | Mitochondrial ribosome | 76 | Up | 4E−07 | 6.34E−05 |
| GO:0006518 | Peptide metabolic process | 612 | Up | 4E−07 | 6.39E−05 |
| GO:0006415 | Translational termination | 90 | Up | 6E−07 | 8.88E−05 |
| GO:0005198 | Structural molecule activity | 318 | Up | 6E−07 | 9.45E−05 |
| GO:0034655 | Nucleobase-containing compound catabolic process | 391 | Up | 7E−07 | 0.000105 |

TABLE 2-continued

Gene ontology analysis of the genes modulated between baseline and 3-month following anti-TNF treatment

| GO ID | Term | Number of genes | Direction | p-value | FDR |
|---|---|---|---|---|---|
| GO:0031294 | Lymphocyte costimulation | 55 | Up | 1.3E−06 | 0.000178 |
| GO:0046700 | Heterocycle catabolic process | 405 | Up | 1.4E−06 | 0.000187 |
| GO:0031295 | T cell costimulation | 54 | Up | 1.5E−06 | 0.0002 |
| GO:0019439 | Aromatic compound catabolic process | 410 | Up | 1.5E−06 | 0.0002 |
| GO:0044270 | Cellular nitrogen compound catabolic process | 407 | Up | 2.2E−06 | 0.000281 |
| GO:0003823 | Antigen binding | 37 | Up | 2.7E−06 | 0.000337 |
| GO:1901361 | Organic cyclic compound catabolic process | 417 | Up | 2.8E−06 | 0.000352 |
| GO:0005743 | Mitochondrial inner membrane | 361 | Up | 2.9E−06 | 0.000363 |
| GO:0072657 | Protein localization to membrane | 349 | Up | 3.3E−06 | 0.000393 |
| GO:0030669 | Clathrin-coated endocytic vesicle membrane | 31 | Up | 3.6E−06 | 0.000423 |
| GO:0042605 | Peptide antigen binding | 18 | Up | 5.2E−06 | 0.000597 |
| GO:0006396 | RNA processing | 752 | Up | 6.3E−06 | 0.000701 |
| GO:0098800 | Inner mitochondrial membrane protein complex | 100 | Up | 9.9E−06 | 0.001004 |
| GO:0022618 | Ribonucleoprotein complex assembly | 176 | Up | 1.01E−05 | 0.001026 |
| GO:0005762 | Mitochondrial large ribosomal subunit | 47 | Up | 1.88E−05 | 0.00176 |
| GO:0050851 | Antigen receptor-mediated signaling pathway | 187 | Up | 2.06E−05 | 0.001917 |
| GO:0019866 | Organelle inner membrane | 393 | Up | 2.12E−05 | 0.001942 |
| GO:0071826 | Ribonucleoprotein complex subunit organization | 186 | Up | 2.56E−05 | 0.002314 |
| GO:0043603 | Cellular amide metabolic process | 706 | Up | 2.56E−05 | 0.002314 |
| GO:0000462 | maturation of SSU-rRNA from Tricistronic rRNA transcript (SSU-rRNA, 5.8S rRNA, LSU-rRNA) | 33 | Up | 3.32E−05 | 0.002863 |
| GO:0098798 | Mitochondrial protein complex | 119 | Up | 3.37E−05 | 0.002881 |
| GO:0070469 | Respiratory chain | 75 | Up | 4.04E−05 | 0.003208 |
| GO:0019886 | Antigen processing and presentation of Exogenous peptide antigen via MHC class II | 72 | Up | 4.51E−05 | 0.003559 |
| GO:0002495 | Antigen processing and presentation of peptide antigen via MHC class II | 74 | Up | 4.57E−05 | 0.003593 |
| GO:0071346 | Cellular response to interferon-gamma | 91 | Up | 5.17E−05 | 0.004031 |
| GO:0030490 | Maturation of SSU-rRNA | 46 | Up | 6.55E−05 | 0.004937 |
| GO:0005746 | Mitochondrial respiratory chain | 69 | Up | 8.37E−05 | 0.006151 |
| GO:1904667 | Negative regulation of ubiquitin protein ligase activity | 67 | Up | 8.87E−05 | 0.006497 |
| GO:0048027 | mRNA 5'-UTR binding | 19 | Up | 9.03E−05 | 0.006535 |
| GO:0050852 | T cell receptor signaling pathway | 152 | Up | 9.07E−05 | 0.006535 |
| GO:0060333 | Interferon-gamma-mediated signaling pathway | 75 | Up | 0.000097 | 0.006828 |
| GO:0030684 | Preribosome | 63 | Up | 9.87E−05 | 0.006909 |
| GO:0000470 | Maturation of LSU-rRNA | 19 | Up | 9.89E−05 | 0.006909 |
| GO:0016071 | mRNA metabolic process | 673 | Up | 0.000101 | 0.00703 |
| GO:0002504 | Antigen processing and presentation of Peptide or polysaccharide antigen via MHC class II | 75 | Up | 0.00012 | 0.008046 |
| GO:0008135 | Translation factor activity, RNA binding | 65 | Up | 0.000142 | 0.008884 |
| GO:0034663 | Endoplasmic reticulum chaperone complex | 10 | Up | 0.000147 | 0.008902 |
| GO:0005759 | Mitochondrial matrix | 317 | Up | 0.000148 | 0.008956 |

Figure 1C:
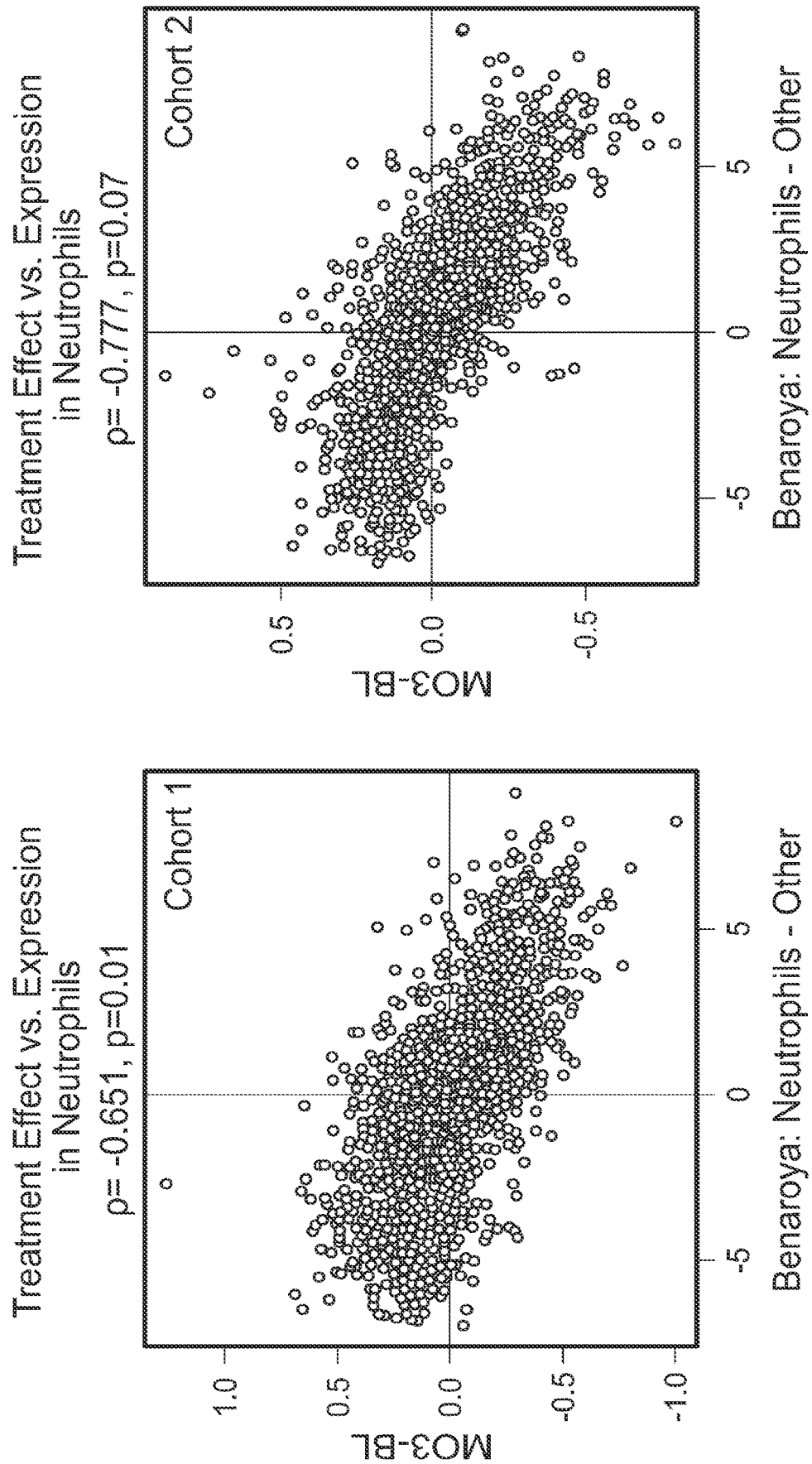
FIG. 1C is a graph showing changes in gene expression after 3 months of anti-TNF treatment relative to baseline (MO3-BL) for genes related to neutrophils for C1 (left graph) and C2 (right graph).
Figure 1D:
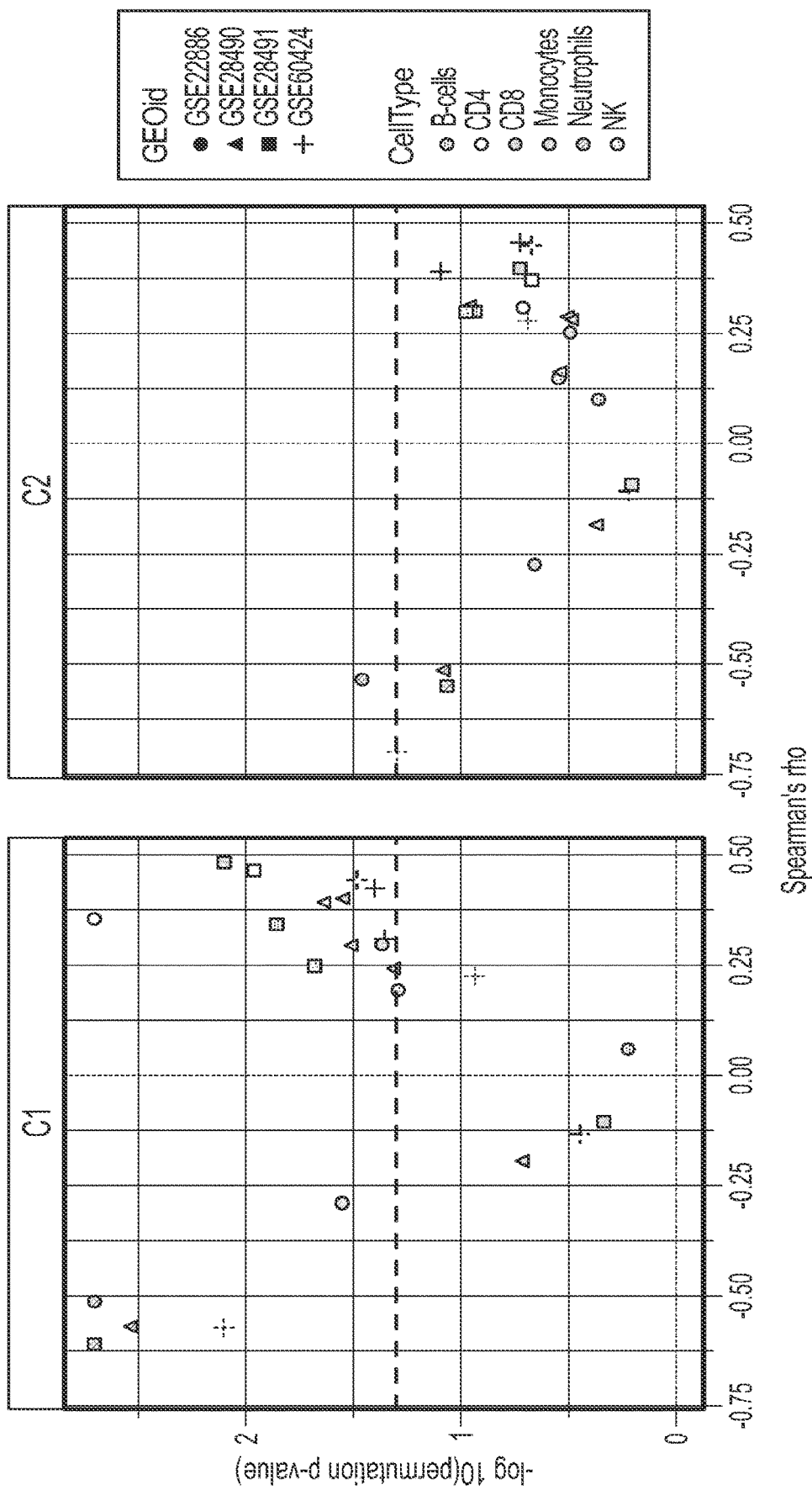
FIG. 1D is a graph showing the changes in gene expression after 3 months of anti-TNF treatment relative to baseline for genes related to different cell types (neutrophils, B-cells, CD4 cells, CD8 cells, monocytes, and NK cells) using four publicly-available cell-type-specific datasets as a reference (GSE22886, GSE28490, GSE28491, and GSE60424) for C1 (left panel) and C2 (right panel).

Cell type-specific RNA-seq data was used to further investigate the cell types that were modulated by anti-TNF treatment. See, Linsley et al., PLoS ONE, 2014, 9(10): e109760, which is herein incorporated by reference in its entirety. FIG. 1C shows that neutrophil-related genes exhibited the largest (by absolute value) and most significant reduction in expression after 3 months of anti-TNF treatment in both cohorts (negative correlation with the effect of anti-TNF treatment). Conversely, genes specific to B cells, CD4 cells, and CD8 cells exhibited increased expression after 3 months of anti-TNF treatment in both cohorts (i.e., were positively correlated with the effect of anti-TNF treatment). The consistency of these results was validated using three other publicly-available cell type-specific datasets as a reference that were generated using microarrays. See, Abbase et al., Genes and Immunity, 2005, 6:319-331; and Allantaz et al., PLoS ONE, 2012, 7(1):e29979, which are herein incorporated by reference in their entirety. FIG. 1D shows that genes related to neutrophils were down-regulated, and genes related to B, CD4, and CD8 cells were up-regulated, after treatment in these cell type-specific datasets. In addition, complete blood count (CBC) analysis showed that, on average, the neutrophils/WBC ratio at month 3 is 87% of that at baseline (95% CI=83-91%; p=1.2*10-6) for C1 and 91% (95% CI=85-97%; p=0,004) for C2, across all patients studied (data not shown), further validating these results.

Protein expression levels in plasma samples was analyzed using shotgun proteomics. FIG. 1E shows the distribution of p-values for the differences in protein expression after 3 months of treatment relative to baseline for C1 and C2. Statistically significant differences between 3-month and baseline samples was detected in both cohorts (14 and 9 proteins at BH-FDR<0.05 in each cohort, permutation p<0.001 in both cohorts). FIG. 1F shows the average differences in protein expression levels between the baseline and 3 month expression levels for C1 and C2, with certain acute phase proteins highlighted. The average differences of protein expression levels between the baseline levels and 3-month follow-up levels showed a positive correlation across all proteins included in the analysis between the two cohorts, which was infrequently observed upon permutation ($\rho$=0.27, p=0.04). Similar to the gene expression results, analysis of gene ontology (GO) categories of the proteins modulated after anti-TNF treatment revealed a down-regulation of inflammatory pathways, although without discriminating between innate and adaptive immune processes (see, Table 3). Conversely, proteins mostly synthesized in the liver, including fibronectin (FN), plasminogen (PLG), apolipoprotein E (APOE) as well as proteins that are not involved in immune functions (i.e. SERPINF1/PEDF, HSPA5/BiP) were increased. Inclusion of less abundant proteins in the analysis resulted in the detection of haptoglobin and C-reactive protein (CRP), both well recognized positive acute phase proteins, which decrease by more than 50% (p 0.01) in each cohort.

Proteomics analysis also showed a reduction pro-inflammatory markers, including complement and acute-phase proteins (See, Table 3). CRP also appeared to be down-regulated. Neutrophil functions, including degranulation, migration/chemotaxis and chemokine production were significantly down-regulated, as well as monocyte-specific pathways and platelet functions (see, Table 2). Conversely, markers of adaptive immune functions, including T cell markers and protein synthesis, were increased, which may be related to the overall decrease in myeloid transcripts.

Figure 2A:
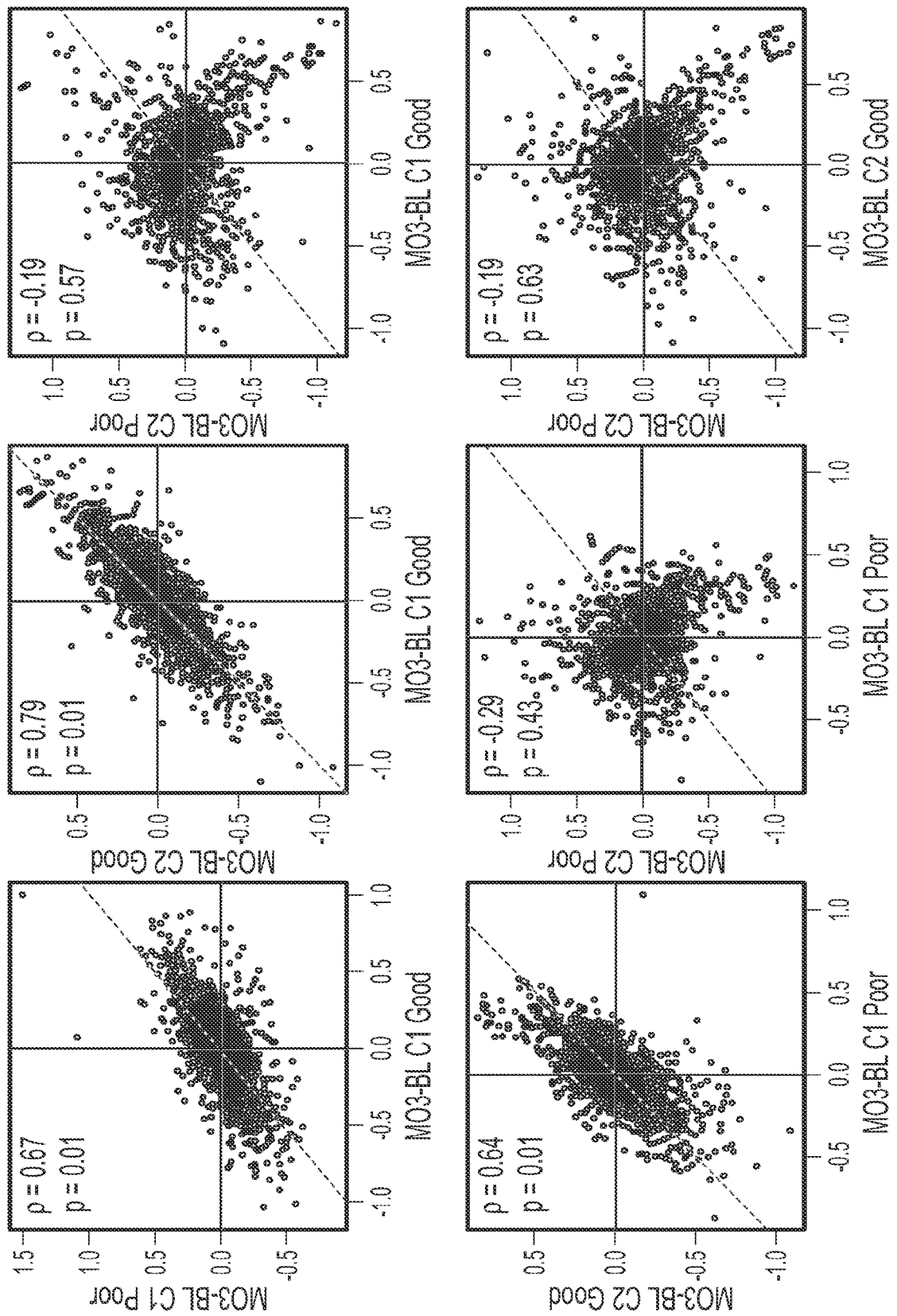
FIG. 2A includes graphs showing pair-wise comparisons of the changes in gene expression after 3 months of anti-TNF treatment (MO3) relative to baseline (BL) between good and poor responders to anti-TNF treatment in C1 and C2.

Example 3. Assessing Association Between the Molecular Signature of Anti-TNF Treatment and Response to Anti-TNF Treatment To determine whether the molecular signature of anti-TNF is reflective of the clinical response of RA patients, and can therefore be used to predict the probability and/or degree to which a patient will respond to anti-TNF therapy, differences in gene expression levels between 3 months and baseline (MO3-BL) were estimated separately for the good responders and the poor responders in each cohort (C1 and C2). The significance of Spearman correlation coefficients for differences in gene expression for each set of subjects was estimated by permutation. FIG. 2A shows the comparison of the differences in gene expression levels (MO3-BL)

TABLE 3

Gene ontology analysis of the proteins modulated between baseline and 3-month of anti-TNF treatment

| GO ID | Term | Number of genes | Direction | p-value | FDR |
|---|---|---|---|---|---|
| GO:0006955 | Immune response | 61 | Down | 0.000576919 | 0.197346629 |
| GO:0002252 | Immune effector process | 51 | Down | 0.00125068 | 0.197346629 |
| GO:0002253 | Activation of immune response | 39 | Down | 0.001743467 | 0.197346629 |
| GO:0050778 | Positive regulation of immune response | 42 | Down | 0.002776652 | 0.197346629 |
| GO:0002920 | Regulation of humoral immune response | 30 | Down | 0.003821307 | 0.197346629 |
| GO:0030449 | Regulation of complement activation | 29 | Down | 0.004224724 | 0.197346629 |
| GO:0002376 | Immune system process | 65 | Down | 0.004342794 | 0.197346629 |
| GO:0002684 | Positive regulation of immune system process | 46 | Down | 0.004881326 | 0.197346629 |
| GO:0006959 | Humoral immune response | 37 | Down | 0.005334188 | 0.197346629 |
| GO:2000257 | Regulation of protein activation cascade | 30 | Down | 0.006739644 | 0.197346629 |
| GO:0002673 | Regulation of acute inflammatory response | 31 | Down | 0.007416631 | 0.197346629 |
| GO:0002250 | Adaptive immune response | 21 | Down | 0.008777251 | 0.197346629 |
| GO:0002443 | Leukocyte mediated immunity | 33 | Down | 0.009034413 | 0.197346629 |
| GO:0050776 | Regulation of immune response | 47 | Down | 0.009143455 | 0.197346629 |
| GO:0006956 | Complement activation | 33 | Down | 0.010827034 | 0.197346629 |
| GO:0044437 | Vacuolar part | 8 | Down | 0.014156612 | 0.197346629 |
| GO:0002020 | Protease binding | 7 | Up | 0.00195389 | 0.197346629 |
| GO:0048589 | Developmental growth | 7 | Up | 0.005823682 | 0.197346629 |
| GO:0033002 | Muscle cell proliferation | 5 | Up | 0.006239685 | 0.197346629 |
| GO:0030182 | Neuron differentiation | 7 | Up | 0.007519171 | 0.197346629 |
| GO:0030030 | Cell projection organization | 9 | Up | 0.009212066 | 0.197346629 |
| GO:0051345 | Positive regulation of hydrolase activity | 7 | Up | 0.010586761 | 0.197346629 |
| GO:0072359 | Circulatory system development | 18 | Up | 0.011941309 | 0.197346629 |
| GO:1901362 | Organic cyclic compound biosynthetic process | 10 | Up | 0.014384575 | 0.197346629 |
| GO:0019218 | Regulation of steroid metabolic process | 5 | Up | 0.015171103 | 0.197346629 |

Thus, transcriptional and proteomics analyses after initiation of anti-TNF treatment confirmed a reduction of inflammatory pathways, with a marked reduction of myeloid-specific functions in both cohorts (C1 and C2). between pairs of each of the groups of patients (comparing C1 good and C1 poor responders; C1 good and C2 good responders; C1 good and C2 poor responders; C2 good and C1 poor responders; C2 good and C2 poor responders, and C1 poor and C2 poor responders). Except for the poor responders from the C2 cohort, the remaining three groups of subjects (the good and poor responders in C1, and the good responders in C2) displayed a significant correlation in MO3-BL differences in each of the comparisons. These results suggested that there were similar changes in gene expression (MO3-BL) of individual genes in the good and poor responders of the cohorts. The low discrepancy in MO3-BL differences in gene expression between responders and poor responders was further confirmed by analyzing pathways modulated in response to anti-TNF treatment, using gene ontology (GO) categories (see, Table 2; data not shown).

Figure 2B:
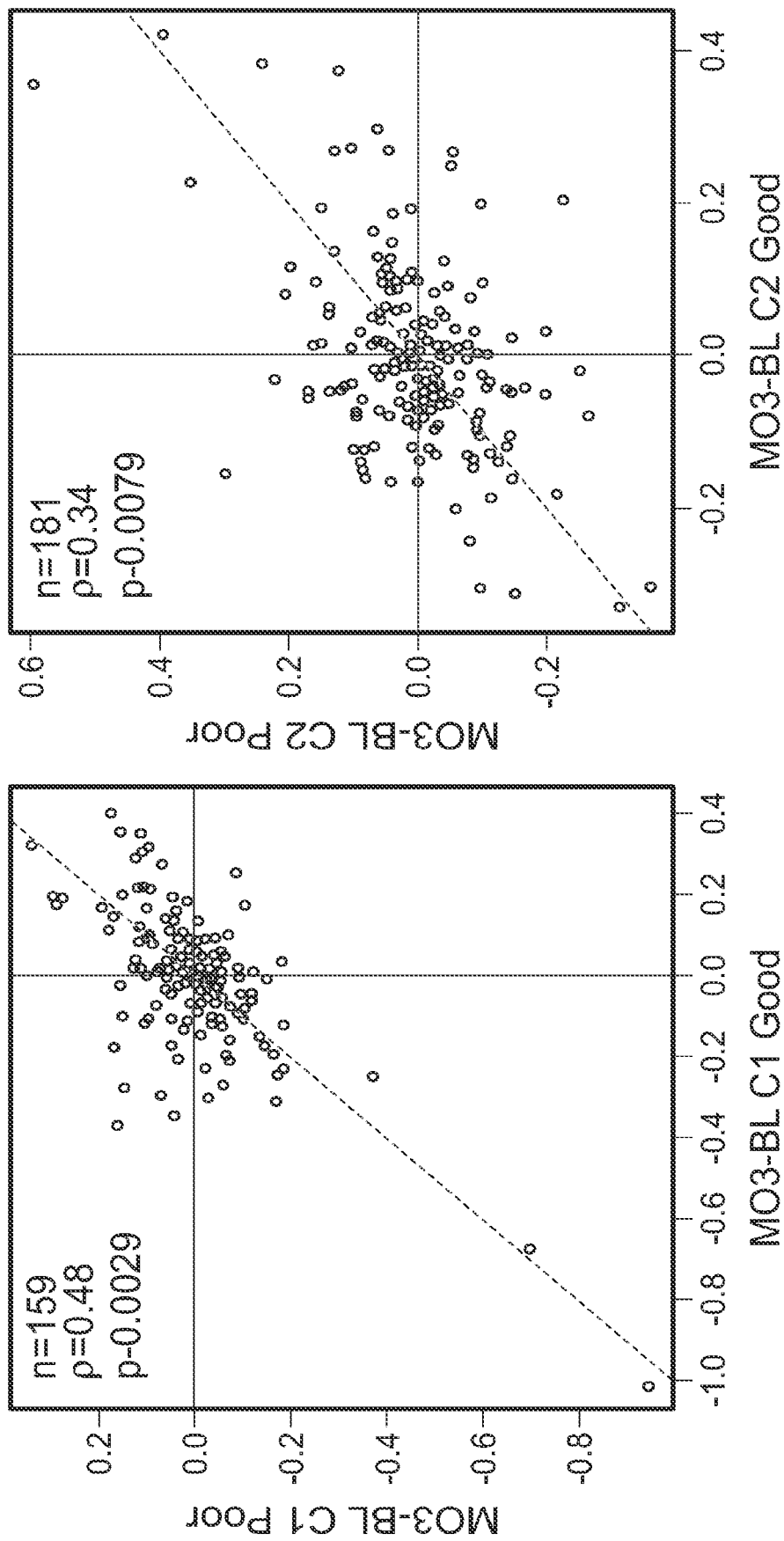
FIG. 2B includes graphs showing comparisons in the differences in protein expression levels after 3 months of anti-TNF treatment relative to baseline (MO3-BL) between the good and poor responders in C1 (Jell panel), and the good and poor responders in C2 (right panel).
Figure 2C:
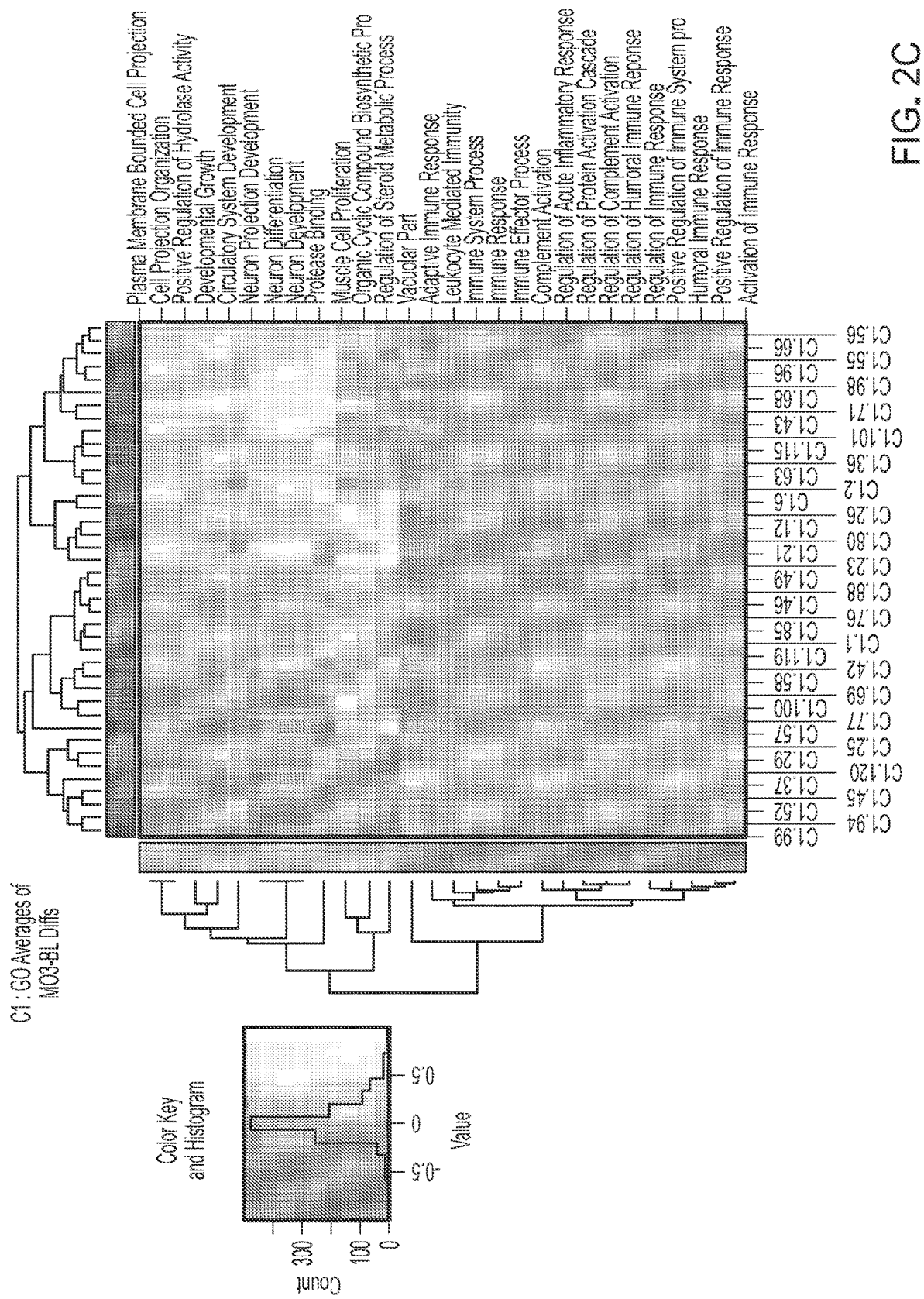
FIG. 2C includes graphs showing differences in the protein expression levels after 3 months of anti-TNF treatment relative to baseline (MO3-BL) for biological pathways (according to gene ontology (GO) categories) that are modulated after anti-TNF expression in the good and in the poor responders in C1 (left panel) and C2 (right panel).
Figure 2C:
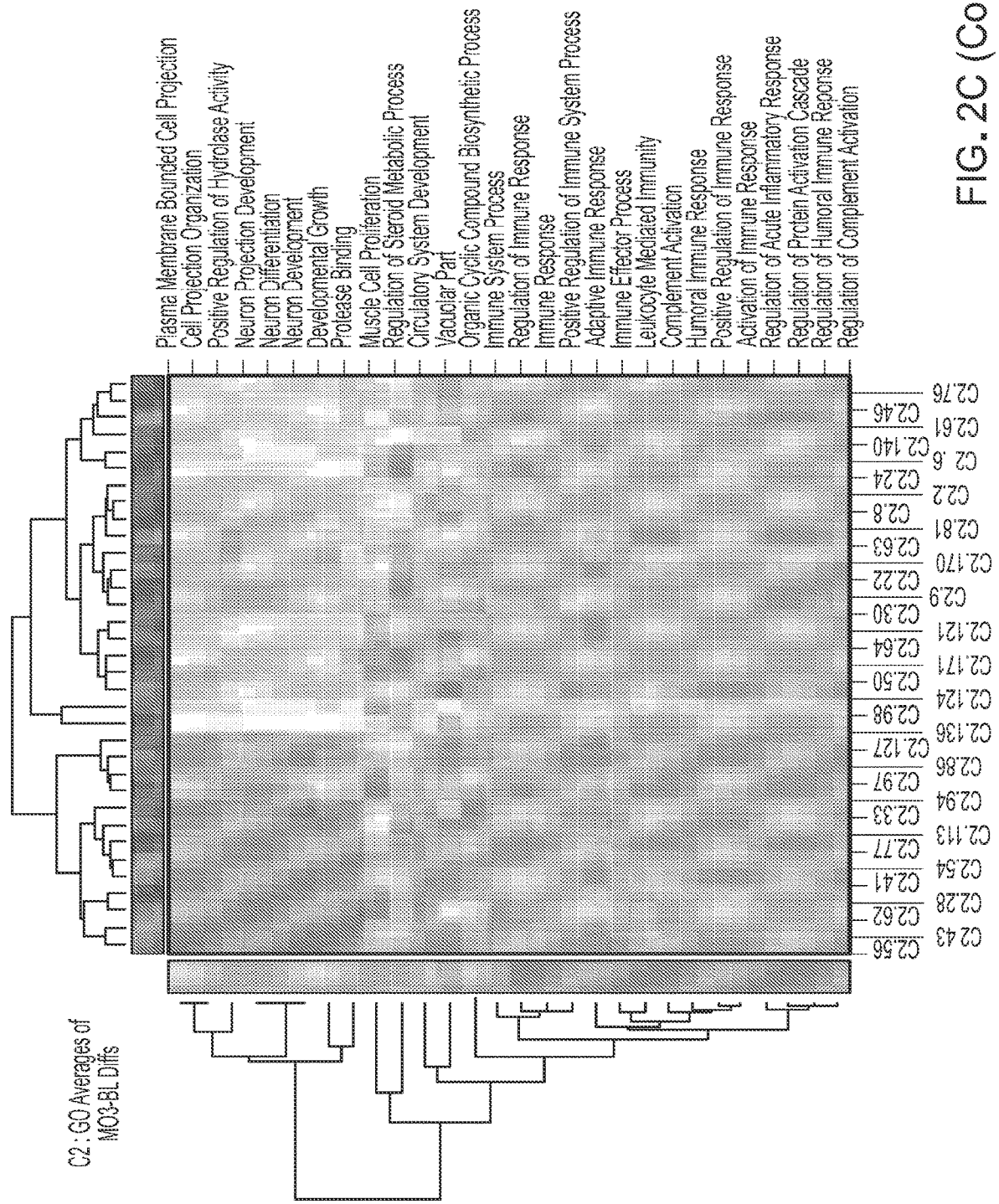

Analysis of 3 months and baseline differences (MO3-BL) using shotgun plasma proteomics corroborated the gene expression findings. FIG. 2B shows comparisons in the differences in protein expression levels (MO3-BL) between the good and poor responders in C1, and the good and poor responders in C2, respectively. Changes in protein expression after anti-TNF treatment were positively correlated ($\rho=0.48$, $p=0.0029$ for C1; $p=0.34$, $p=0.0079$) between good and poor responders in both cohorts. FIG. 2C shows differences in the protein expression levels (Mo3-BL) in pathways that are modulated after anti-TNF expression, using gene ontology categories (see, Table 3); in the good and in the poor responders in C1 and C2. It was not possible to discriminate between good and poor responders based on the expression of proteins in these pathways. Changes in cell populations by complete blood count (CBC) analysis showed a greater decrease in the neutrophils/WBC ratio from baseline to 3-month in good responders than in poor responders in both cohorts (by 10% and 6% in the C1 and C2 cohorts, respectively). These results were only statistically significant for C ($\rho=0.03$; 95% CI=[$-19\%,-1.6\%$]), and not for C2 ($\rho=0.30$; 95% CI=[$-18\%, 5.9\%$]).

Overall, the results indicated that the molecular signature of anti-TNF was not closely correlated with whether the RA patients in C1 and C2 were good or poor responders. Additional factors are probably involved in the development of demonstrable clinical responses to anti-TNF treatment.

Example 4. Analysis of Gene Expression Prior to Anti-TNF Treatment (at Baseline)

Figure 3A:
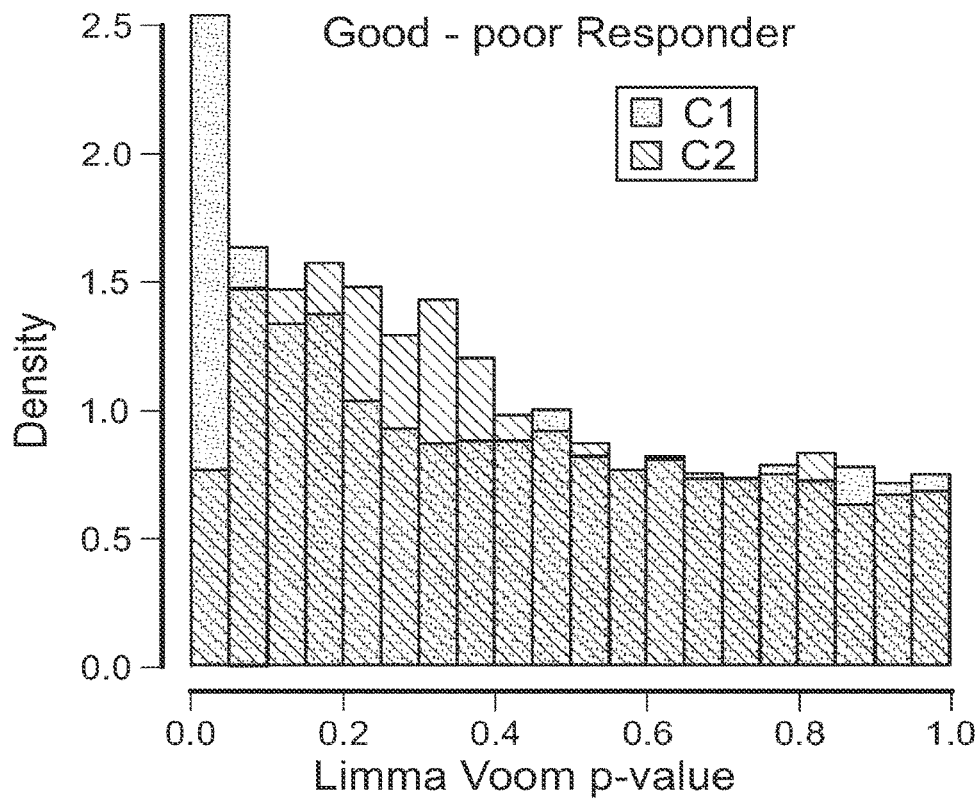
FIG. 3A is a graph showing the differences in gene expression between the good responders and poor responders prior to anti-TNF treatment, plotted according to statistical significance (distribution of p-values).
Figure 3B:
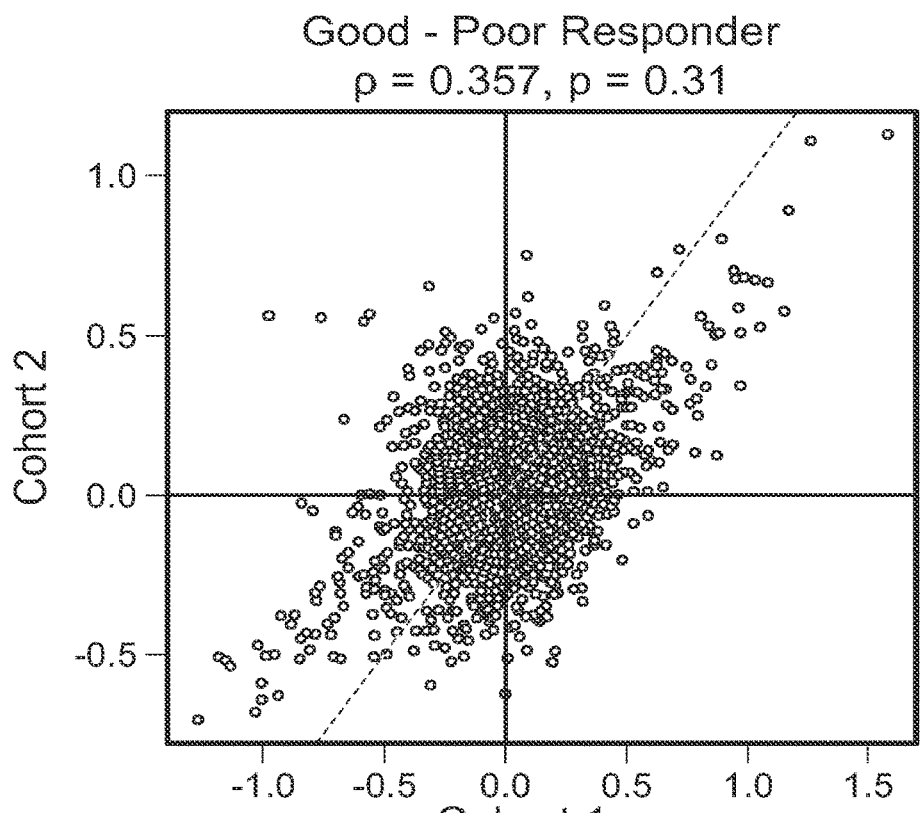
FIG. 3B is a graph showing the differences in baseline gene expression levels between the good responders and poor responders to anti-TNF treatment, plotted for Cohort 1 (C1) versus Cohort 2 (C2).

Gene expression in the good and poor responders of C1 and C2 prior to anti-TNF treatment (at baseline) was compared to determine whether baseline gene expression levels could be used to predict whether a patient would respond well (or poorly) to anti-TNF treatment. FIG. 3A shows the distribution of p-values for the differences in gene expression between good responders and poor responders prior to anti-TNF treatment (at baseline) in C1 and C2. Only modest differences in gene expression between the good and poor responders were demonstrated. Differences between gene expression levels achieved statistical significance in C1 (77 and 536 genes at BH-FDR cutoffs of 0.1 and 0.2 respectively) but not in C2 (lowest BH-MR of 0.73). FIG. 3B shows the differences in baseline gene expression levels between the good and poor responders in C1 and C2. The gene expression levels correlated positively between the two cohorts, but no statistical significance was achieved by permutation control ($\rho=0.21$; $p=0.45$).

Figure 3C:
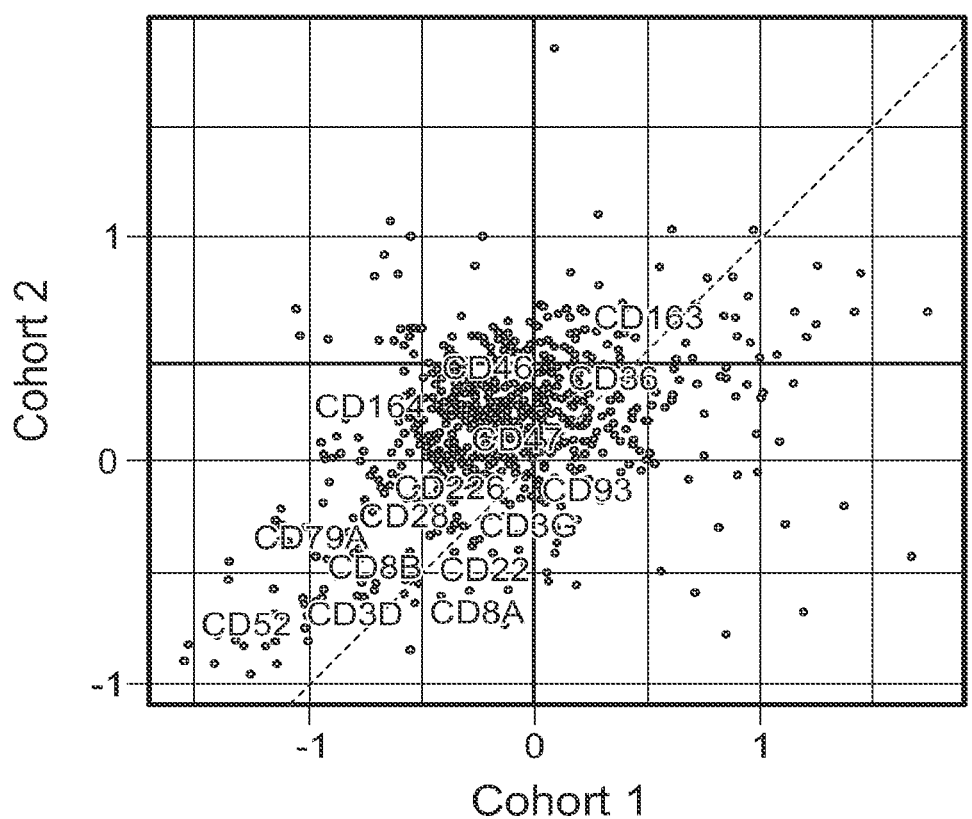
FIG. 3C is a graph showing the differences in baseline gene expression levels between the good responders and poor responders to anti-TNF treatment for a subset of genes that exhibited the greatest expression variability between the good and poor responders, plotted for Cohort 1 (C1) versus Cohort 2 (C2).

FIG. 3C shows a comparison of the baseline gene expression differences between the good and poor responders for the 10% most variable genes (i.e., those genes whose expression varied the most across baseline samples on average between C1 and C2) in C1 and the 10% most variable genes in C2, with certain genes highlighted (e.g., cell surface markers fix myeloid cells and lymphocytes). Comparing the 10% most variable genes between good and poor responders in each cohort resulted in a higher correlation between the cohorts, Genes for cell surface markers that are associated with myeloid cells (CD14, CD36, CD46, CD47, CD163, and CD164) were expressed at higher levels on average in good responders in both cohorts prior to anti-TNF treatment (at baseline), while genes for surface markers for lymphocytes, including T cells (CD52, CD48, CD3D, CD8A) and B-cells (CD79B, CD22), were expressed at higher levels on average in poor responders in both cohorts prior to anti-TNF treatment (at baseline). This result suggested that good and poor responders exhibited differences in their immune systems prior to anti-TNF treatment (i.e., at baseline), including in the number or characteristics of their myeloid and lymphocyte cells.

Figure 4A:
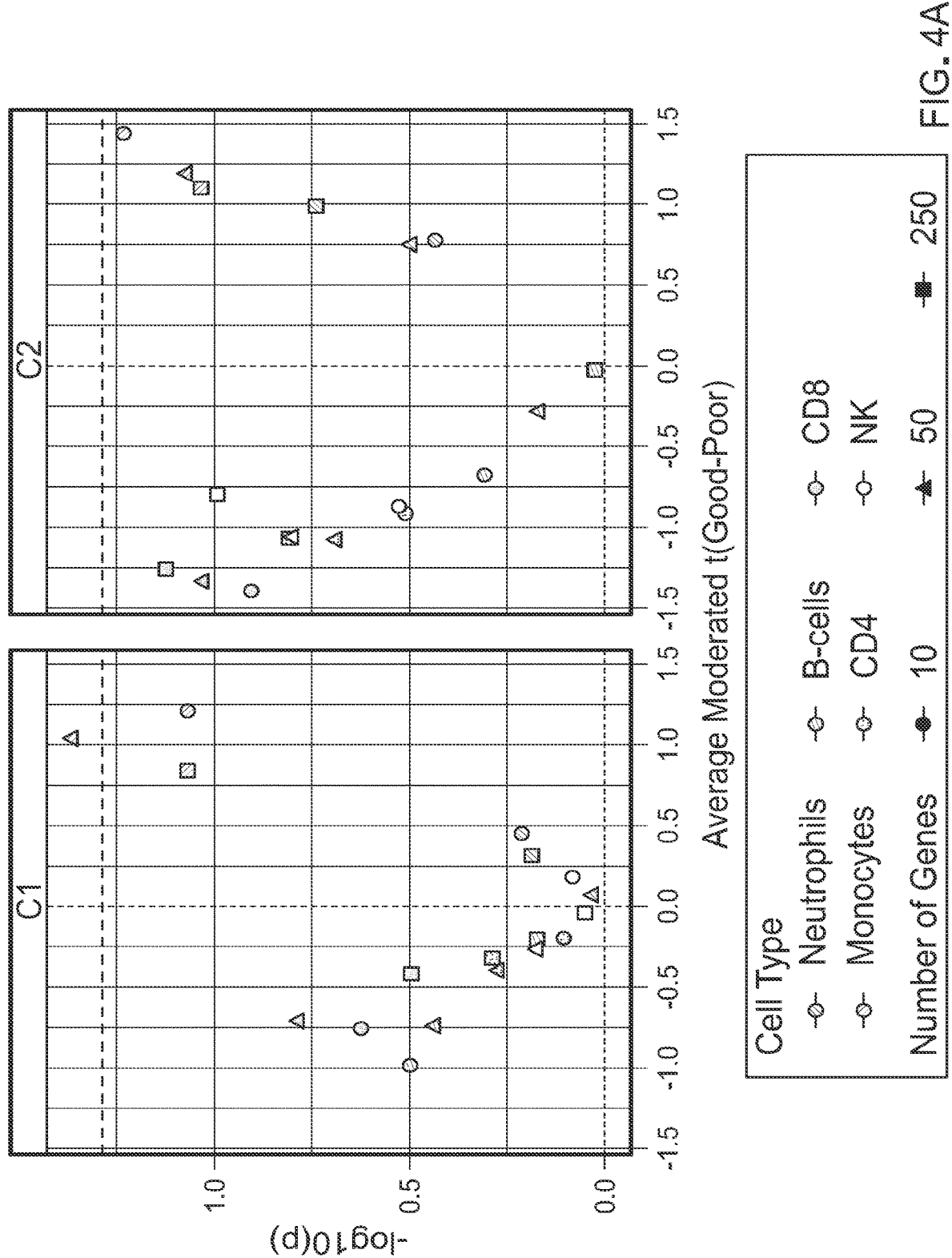
FIG. 4A is a graph showing the average baseline expression of subsets of genes (subsets of the top 10 genes, top 50 genes, or top 250 genes) that are predominantly expressed in particular cell types (neutrophils, B-cells, CD4 cells, CD8 cells, monocytes, and NK cells) in good responders compared to poor responders in C1 (left panel) and C2 (right panel).
Figure 4B:
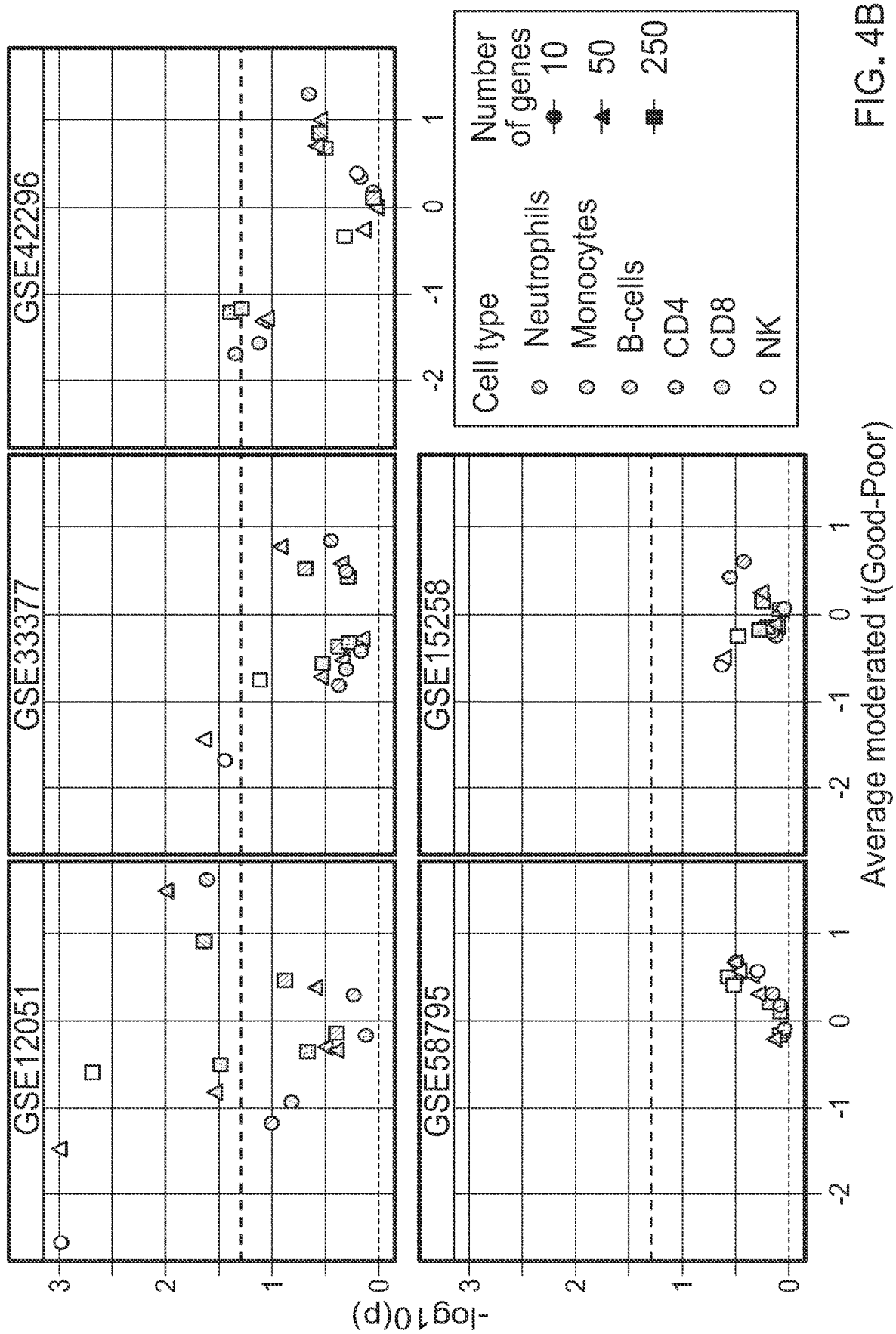

The cell type-specific RNA-seq methodology (described with FIG. 1C) was used to further understand the immune system differences between good and poor responders at baseline. FIG. 4A shows the average gene expression at baseline for subsets of genes associated with particular cell types (neutrophils, monocytes, CD4 cells, CD8 cells, and NK cells) in good responders compared to poor responders in C1 and C2. Subsets of the top 10 genes (FIG. 7), top 50 genes (FIG. 8), or top 250 genes (FIG. 9), based on their expression levels in the particular cell types, were used, as determined using a reference cell-type specific data set. See, Linsley et al., PLoS ONE, 9(10):e109760. Genes that are most expressed in innate immune cells (neutrophils and monocytes) were, on average, found to be expressed at higher levels in good responders, while genes predominantly expressed in the adaptive compartment (CD4/CD8/NK/B-cells) were on average expressed at higher levels in poor responders. Thus, RA patients that will exhibit good response to anti-TNF treatment appear to likely have more innate immune cells (including neutrophils and monocytes) prior to anti-TNF treatment, while RA patients that will exhibit poor response to anti-TNF treatment likely have more adaptive immune cells prior to anti-TNF treatment. This observation was statistically significant as estimated by permutation and assessed across both cohorts ($\rho=0.03$), and interesting given the limited conservation observed between C1 and C2 in the broader transcriptional analysis of FIG. 3A. The results were further confirmed by performing a similar analysis using five publicly available RA datasets containing gene expression data at baseline for responders and non-responders to anti-TNF therapy. See, Julia et al., PLoS ONE, 2009, 4(10):e7556; Bienkowska et al., Genomics, 2009, 94:423-432 Toonen et al., PLoS ONE, 2012, 7(3):e33199; Mesko et al., Genome Medicine, 2013, 5:59 and MacIsaac et al., PLoS ONE, 2014, 9(12):e113937, which are herein incorporated by reference in their entirety. FIG. 4B shows that despite differences in study designs, three datasets display qualitatively similar results wherein, on average, genes elevated in the innate compartment were expressed at higher levels in good responders and genes elevated in adaptive compartment were expressed at higher levels in poor responders.

Thus, at baseline, innate immune cell types were on average expressed at higher level in good responders from both cohorts, while the adaptive immune cell types were on average expressed at a higher level in poor responders (see, FIG. 3C and FIG. 4A). This observation was confirmed in three publicly available datasets after applying cell-type specific gene expression analysis (see, FIG. 4B). The reproducibility of the Observation, despite the differences in the underlying studies that produced the datasets (including in patient selection and sample processing), shows that the make-up of the immune cells in subjects with RA is an important feature in determining response to anti-TNF therapies.

Example 5. Baseline Immune Cells as Predictors of Anti-TNF Tre n Ent Response

Since the subset of genes evaluated in the above examples represent immune cell types present in blood, clinical information on blood cell types (neutrophil, lymphocyte and WBC counts) present in 2011 patients were analyzed to determine whether it can be predictive of RA patient response to anti-TNF therapy. Logistic regression models were set up to evaluate the probability that RA patients would exhibit a good or moderate EULAR response 3 months after starting anti-TNF therapy, as a function of their baseline neutrophil to lymphocyte log ratio [NLR], neutrophil to white blood cell (WBC) log ratio [NWR], or lymphocyte to WBC log ratio [LWR]. Three separate models (NLR, NVR, and LWR) were established for 2011 patients for whom the number of neutrophils, lymphocytes and WBCs were determined prior to anti-TNF treatment (at baseline) by complete blood count (CBC), and whose EULAR response was determined at a follow-up visit 3 month after anti-TNF treatment. The patients were evaluated, either without adjustment, or by adjusting for multiple variables, including the type of biologic received (Humira®/Remicade®, other anti-TNF biologic, or other non-anti-TNF biologic), patient experience with biologics (biologic naïve vs. experienced), and other covariates age, disease duration, smoking status, disability index, erosions, methotrexate treatment and number of prior biologics).

Readouts from linear regression models depict the probability of an RA patient exhibiting a good response as a function of neutrophil to lymphocyte ratio, neutrophil to WBC ratio, or lymphocyte to WBC ratio. The results of the first model showed that a one-unit increase in baseline NLR, log ratio resulted in approximately a 20% increased probability of moderate to good EULAR response (1.23 increased probability) (unadjusted OR=1.23, 95% CI=1.06, 1.42; adjusted OR=1.20, 95% C1=1.03, 1.41). The effect is equivalent to concomitant methotrexate (MTX) treatment (odds ratio of MTX to good/moderate response=1.23 [95% CI=1.02-1.49; p=0.03]), which is used as a first-line therapy. The importance of neutrophils to anti-TNF response was confirmed by the second model, where a one-unit increase in baseline NWR log ratio resulted in a 1.9 increased probability of moderate or good EULAR response (unadjusted OR=1.91, 95% CI=1.14, 3.18; adjusted OR=1.72, 95% CI=1.01, 2.96). Conversely, the association between increased lymphocytes at baseline and non-response to anti-TNF therapy was emphasized by a 24% decreased probability of moderate or good EULAR response, following a one-unit increase in baseline LWR log ratio (unadjusted OR=0.76, 95% CI=0.62, 0.93; adjusted OR=0.77, 95% CI=0.62, 0.95). Thus, significant associations between NLR, NWR and LWR log ratios and EULAR response were observed.

The results of these models are consistent with the gene and protein expression observations described in the above examples. FIG. 5 shows a correlation between average baseline expression profiles of genes that are predominantly expressed in neutrophils, B cells, CD4 cells. CD8 cells, monocytes and NK cells in C1 and C2, compared to the corresponding counts of the cells and their ratios. Good responders have on average a higher fraction of innate immune cells at baseline, while poor responders have on average a higher fraction of adaptive immune cells at baseline. FIG. 5 thus shows that cell-type specific genes correlate with corresponding cell counts. Thus, clinical laboratory metrics at baseline can be useful readouts to assess predictability of response to anti-TNF treatment in RA patients. Determining the neutrophil to lymphocyte ratio, or normalized lymphocyte or neutrophil counts (i.e., lymphocyte/WBC or neutrophil/WBC ratios), in a subject with RA prior to anti-TNF treatment (baseline) using CBC can be used to predict whether that subject will respond to anti-TNF treatment.

What is claimed is:

1. A method for treating rheumatoid arthritis in a subject in need thereof, the method comprising:
    detecting, in a biological sample from the subject, a value of a neutrophil to lymphocyte log ratio (ln[NLR]) of greater than 1.3, and
    administering to the subject an anti-TNF therapeutic, thereby treating the subject.

2. The method of claim 1, wherein the anti-TNF therapeutic is selected from the group consisting of infliximab, adalimumab, golimumab, certolizumab pegol and etanercept.

3. The method of claim 1, wherein the ln[NLR] is greater than 1.4.

4. The method of claim 1, wherein the ln[NLR] is greater than 1.5.

5. The method of claim 1, wherein the ln[NLR] is greater than 1.6.

6. A method for treating rheumatoid arthritis in a subject in need thereof, the method comprising:
    detecting, in a biological sample from the subject, a value of a ln[NLR] of 1.3 or below, and
    administering to the subject a rheumatoid arthritis therapeutic other than an anti-TNF therapeutic, thereby treating the subject.

7. The method of claim 6, wherein the rheumatoid arthritis therapeutic is selected from the group consisting of an anti-CD20 antibody, an anti-IL-6R antibody, and a CTLA-4-Ig fusion protein.

8. The method of claim 6, wherein the ln[NLR] is 1.2 or below.

9. The method of claim 6, wherein the ln[NLR] is 1.1 or below.

10. The method of claim 6, wherein the ln[NLR] is 1.0 or below.

* * * * *